US010916711B2

United States Patent
Adachi et al.

(10) Patent No.: US 10,916,711 B2
(45) Date of Patent: Feb. 9, 2021

(54) SPIRO COMPOUND HAVING AZAFLUORENE RING STRUCTURE, LIGHT-EMITTING MATERIAL, AND ORGANIC ELECTROLUMINESCENT DEVICE

(71) Applicants: Hodogaya Chemical Co., Ltd., Tokyo (JP); Kyushu University, National University Corporation, Fukuoka (JP)

(72) Inventors: Chihaya Adachi, Fukuoka (JP); Takuma Yasuda, Fukuoka (JP); Tetsuya Nakagawa, Fukuoka (JP); Katsuyuki Shizu, Fukuoka (JP); Hiroshi Ookuma, Tokyo (JP)

(73) Assignees: Hodogaya Chemical Co., Ltd., Tokyo (JP); Kyulux, Inc., Fukuoka (JP)

( * ) Notice: Subject to any disclaimer, the term of this patent is extended or adjusted under 35 U.S.C. 154(b) by 117 days.

(21) Appl. No.: 15/124,840

(22) PCT Filed: Mar. 2, 2015

(86) PCT No.: PCT/JP2015/001074
§ 371 (c)(1),
(2) Date: Sep. 9, 2016

(87) PCT Pub. No.: WO2015/136880
PCT Pub. Date: Sep. 17, 2015

(65) Prior Publication Data
US 2017/0018720 A1    Jan. 19, 2017

(30) Foreign Application Priority Data

Mar. 11, 2014 (JP) ................................ 2014-047367

(51) Int. Cl.
*H01L 51/00* (2006.01)
*C07D 471/10* (2006.01)
(Continued)

(52) U.S. Cl.
CPC ........ *H01L 51/0072* (2013.01); *C07D 403/12* (2013.01); *C07D 403/14* (2013.01);
(Continued)

(58) Field of Classification Search
CPC .. C07D 471/10; C07D 403/12; C07D 403/14; C07D 413/14; C07D 471/20;
(Continued)

(56) References Cited

U.S. PATENT DOCUMENTS

2007/0292715 A1    12/2007 Yoon et al.
2010/0019658 A1*    1/2010 Lin ...................... C07D 219/14
                                                                                    313/504
(Continued)

FOREIGN PATENT DOCUMENTS

CN        101006158 A        7/2007
JP        2008-510801 A      4/2008
(Continued)

OTHER PUBLICATIONS

Machine Translation of KR-20110109687 from KIPO, dated Aug. 1, 2018. (Year: 2018).*
(Continued)

*Primary Examiner* — Jennifer A Chriss
*Assistant Examiner* — Sean M DeGuire
(74) *Attorney, Agent, or Firm* — Locke Lord LLP; James E. Armstrong, IV; Nicholas J. DiCeglie, Jr.

(57) ABSTRACT

A compound that emits fluorescence and delayed fluorescence is provided as a material for an organic electroluminescent device of high efficiency, and an organic photoluminescent device and an organic electroluminescent device of high efficiency and high luminance are provided using this compound. The spiro compound of a general formula (1) having an azafluorene ring structure is used as a con-
(Continued)

← 7 CATHODE
← 6 ELECTRON INJECTION LAYER
← 5 ELECTRON TRANSPORT LAYER
← 4 LIGHT EMITTING LAYER
← 3 HOLE TRANSPORT LAYER
← 2 TRANSPARENT ANODE
← 1 GLASS SUBSTRATE stituent material of at least one organic layer in an organic electroluminescent device that includes a pair of electrodes, and one or more organic layers sandwiched between the pair of electrodes.

[Chemical Formula 1]

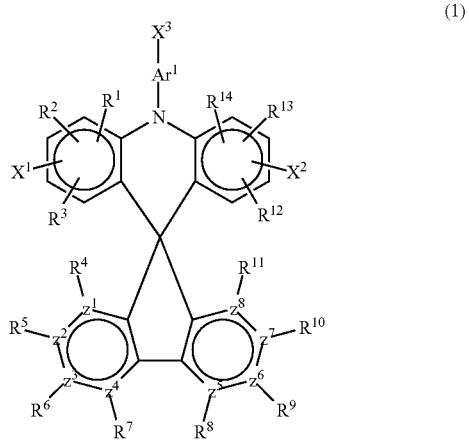

(1)

11 Claims, 3 Drawing Sheets

(51) Int. Cl.
C07D 471/20 (2006.01)
C09K 11/06 (2006.01)
C07D 403/12 (2006.01)
C07D 487/04 (2006.01)
C07D 403/14 (2006.01)
C07D 413/14 (2006.01)
C07F 9/6584 (2006.01)
C07F 11/00 (2006.01)
C09K 11/02 (2006.01)
H01L 51/50 (2006.01)

(52) U.S. Cl.
CPC ......... *C07D 413/14* (2013.01); *C07D 471/10* (2013.01); *C07D 471/20* (2013.01); *C07D 487/04* (2013.01); *C07F 9/6584* (2013.01); *C07F 9/65846* (2013.01); *C07F 11/00* (2013.01); *C09K 11/02* (2013.01); *C09K 11/06* (2013.01); *H01L 51/006* (2013.01); *H01L 51/0059* (2013.01); *H01L 51/0061* (2013.01); *H01L 51/0065* (2013.01); *H01L 51/0068* (2013.01); *H01L 51/0071* (2013.01); *H01L 51/0077* (2013.01); *C09K 2211/104* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1037* (2013.01); *C09K 2211/1044* (2013.01); *C09K 2211/1088* (2013.01); *C09K 2211/1092* (2013.01); *C09K 2211/188* (2013.01); *H01L 51/0052* (2013.01); *H01L 51/0058* (2013.01); *H01L 51/0073* (2013.01); *H01L 51/5012* (2013.01); *H01L 51/5056* (2013.01); *H01L 51/5096* (2013.01)

(58) Field of Classification Search
CPC .............. C07D 487/04; H01L 51/0072; H01L 51/0052; H01L 51/0058; H01L 51/006; H01L 51/0068; H01L 51/5012; H01L 51/5056; H01L 51/5096; C09K 2211/1044
See application file for complete search history.

(56) References Cited

U.S. PATENT DOCUMENTS

2010/0219406 A1\* 9/2010 Kahle ................ H01L 51/0061 257/40
2011/0278549 A1 11/2011 Kim et al.

FOREIGN PATENT DOCUMENTS

| JP | 2013-510848 A | | 3/2013 |
|---|---|---|---|
| KR | 10-2011-0109687 A | | 10/2011 |
| KR | 10-2011-0114229 A | | 10/2011 |
| KR | 20110109687 A | \* | 10/2011 |
| WO | 2006/033564 A1 | | 3/2006 |
| WO | WO-2014017844 A1 | \* | 1/2014 |

OTHER PUBLICATIONS

Japanese Translation of Office Action dated Mar. 22, 2017, issued for the corresponding Chinese patent application.
Hiroshi Ohkuma et al., "Thermally Activated Delayed Fluorescence from a Spiro-diazafluorene Derivative," Chem. Lett., 2014, pp. 1017-1019.
International Search Report dated Apr. 28, 2015, issued for PCT/JP2015/001074.

\* cited by examiner

← 7 CATHODE
← 6 ELECTRON INJECTION LAYER
← 5 ELECTRON TRANSPORT LAYER
← 4 LIGHT EMITTING LAYER
← 3 HOLE TRANSPORT LAYER
← 2 TRANSPARENT ANODE
← 1 GLASS SUBSTRATE

SPIRO COMPOUND HAVING AZAFLUORENE RING STRUCTURE, LIGHT-EMITTING MATERIAL, AND ORGANIC ELECTROLUMINESCENT DEVICE

TECHNICAL FIELD

The present invention relates to compounds suitable for an organic electroluminescent device, which is a preferred self-luminous device for various display devices, and to such organic electroluminescent devices. Specifically, this invention relates to spiro compounds having an azafluorene ring structure, and to organic electroluminescent devices using the compounds.

BACKGROUND ART

An organic electroluminescent device is a self-luminous device, and has been actively studied for their brighter, superior visibility, and the ability to display clearer images in comparison with liquid crystal devices.

In an attempt to improve the device luminous efficiency, there have been developed devices that use phosphorescent materials to generate phosphorescence, specifically that make use of the emission from a triplet excitation state. According to the excitation state theory, phosphorescent materials are expected to greatly improve luminous efficiency as much as about four times that of conventional fluorescence.

In 1993, M. A. Baldo et al. at Princeton University achieved 8% external quantum efficiency with a phosphorescent device using an iridium complex.

Devices that use light emission caused by thermally activated delayed fluorescence (TADF) have also been developed. In 2011, Adachi et al. at Kyushu University, National University Corporation achieved 5.3% external quantum efficiency with a device using a thermally activated delayed fluorescent material (refer to Non-Patent Document 1, for example).

In an organic electroluminescent device, carriers are injected from each of both electrodes, i.e., positive and negative electrodes to a light-emitting substance to generate a light-emitting substance in an excited state so as to emit light. It is generally said that in the case of a carrier injection type organic electroluminescent device, 25% of generated excitons are excited to an excited singlet state and the remaining 75% are excited to an excited triplet state. Accordingly, it is conceivable that utilization of light to be emitted from the excited triplet state, i.e., phosphorescence should provide higher energy use efficiency. However, in the phosphorescence, the excited triplet state has a long lifetime, and hence deactivation of energy occurs through saturation of an excited state and interactions with excitons in an excited triplet state, with the result that a high quantum yield is not obtained in many cases in general.

In view of the foregoing, an organic electroluminescent device utilizing a material which emits delayed fluorescence is conceivable. A certain kind of fluorescent substance emits fluorescence via intersystem crossing or the like leading to energy transition to an excited triplet state and the subsequent reverse intersystem crossing to an excited singlet state through triplet-triplet annihilation or thermal energy absorption. In the organic electroluminescent device, it is considered that the latter material which emits thermally activated delayed fluorescence is particularly useful. In this case, when a delayed fluorescent material is utilized in the organic electroluminescent device, excitons in an excited singlet state emit fluorescence as per normal. On the other hand, excitons in an excited triplet state absorb heat produced from a device and undergo intersystem crossing to an excited singlet to emit fluorescence. The fluorescence in this case is light emission from the excited singlet and hence is light emission at the same wavelength as fluorescence. However, the fluorescence has a longer lifetime of light to be emitted, i.e., a longer emission lifetime than those of normal fluorescence and phosphorescence by virtue of reverse intersystem crossing from an excited triplet state to an excited singlet state, and hence is observed as fluorescence delayed as compared to the normal fluorescence and phosphorescence. This can be defined as delayed fluorescence. Through the use of such thermally activated type exciton transfer mechanism, i.e., through thermal energy absorption after carrier injection, the ratio of a compound in an excited singlet state, which has usually been generated only at a ratio of 25%, can be increased to 25% or more. The use of a compound which emits intense fluorescence and delayed fluorescence even at a low temperature of less than 100° C. results in sufficient intersystem crossing from an excited triplet state to an excited singlet state by means of heat of a device, contributing to emission of delayed fluorescence. Thus, the luminous efficiency is drastically improved (refer to Patent Document 1 and Patent Document 2, for example).

Various organic electroluminescent devices using spiro compounds have been proposed, including an organic electroluminescent device with a hole blocking layer for which a compound having a spirobifluorene structure is used (refer to Patent Document 3, for example), an organic electroluminescent device with a light emitting layer for which a compound having a spiro-linked fluorene structure and diazafluorene structure is used (refer to Patent Document 4, for example), an organic electroluminescent device with a light emitting layer for which a compound having a spiro-linked fluorene structure and acridine structure is used (refer to Patent Document 5, for example), and an organic electroluminescent device with a light emitting layer for which a spiro-linked acridine structure and anthrone structure is used (refer to Patent Document 6, for example).

However, it cannot be said that there are comprehensive studies covering all compounds having a spiro structure, and the previous studies merely indicate potential use of only a handful of compounds having a spiro structure in applications as light-emitting materials of an organic electroluminescent device. Further, the related art neither discloses nor indicates producing delayed fluorescence.

CITATION LIST

Patent Documents

Patent Document 1: JP-A-2004-241374
Patent Document 2: JP-A-2006-024830
Patent Document 3: JP-T-2006-528836
Patent Document 4: WO2003/020847
Patent Document 5: WO2006/033564
Patent Document 6: US Patent Published Application No. 2012-0001537
Non-Patent Documents
Non-Patent Document 1: Appl. Phys. Let., 98, 083302 (2011)
Non-Patent Document 2: Synth. Commun., 11, 513 (1981)
Non-Patent Document 3: Appl. Phys. Let., 101, 093306 (2012)

Non-Patent Document 4: Chem. Commun., 48, 11392 (2012)
Non-Patent Document 5: NATURE 492, 235 (2012)
Non-Patent Document 6: Organic EL Symposium, the 1st Regular presentation Preprints, 19 (2005)

SUMMARY OF THE INVENTION

Problems to be Solved by the Invention

An object of the present invention is to provide a compound that emits fluorescence and delayed fluorescence as a material for an organic electroluminescent device of high efficiency, and to provide an organic photoluminescent (hereinafter referred to as "PL") device, and an organic electroluminescent device of high efficiency and high luminance using this compound.

Means for Solving the Problems

To achieve the above object, the present inventors have noted spiro compounds having an azafluorene ring structure, and designed and chemically synthesized compounds using, as indexes, a difference between excited triplet energy and excited singlet energy ($\Delta E_{ST}$), and oscillator strength (f) which are obtained by theoretical calculation. As a result of actually measuring the emission (PL) spectrums of the chemically synthesized compounds, the present inventors found new spiro compounds having an azafluorene ring structure which emit delayed fluorescence. The present inventors produced various test organic electroluminescent devices using these compounds, and the present invention was completed after thorough evaluations of device characteristics.

1) Specifically, the present invention is a spiro compound of the following general formula (1) having an azafluorene ring structure.

[Chemical Formula 1]

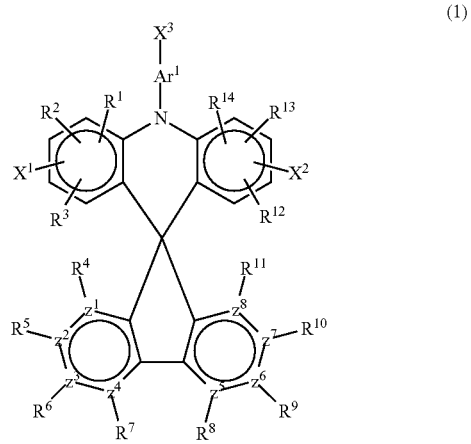

(1)

In the formula, $X^1$, $X^2$, and $X^3$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein at least one of $X^1$, $X^2$, and $X^3$ is a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group.

$Ar^1$ represents a divalent group of a substituted or unsubstituted aromatic hydrocarbon, a divalent group of a substituted or unsubstituted aromatic heterocyclic ring, or a divalent group of a substituted or unsubstituted condensed polycyclic aromatic group, $R^1$ to $R^{14}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^{14}$ may bind to each other via a single bond, substituted or unsubstituted methylene, an oxygen atom, or a sulfur atom to form a ring.

$Z^1$ to $Z^8$ are carbon atoms or nitrogen atoms, wherein at least one of $Z^1$ to $Z^8$ is a nitrogen atom, and in this case the nitrogen atom does not have the hydrogen atom or the substituent of $R^4$ to $R^{11}$.

2) The present invention is a spiro compound having an azafluorene ring structure according to 1), the compound being represented by the following general formula (1a).

[Chemical Formula 2]

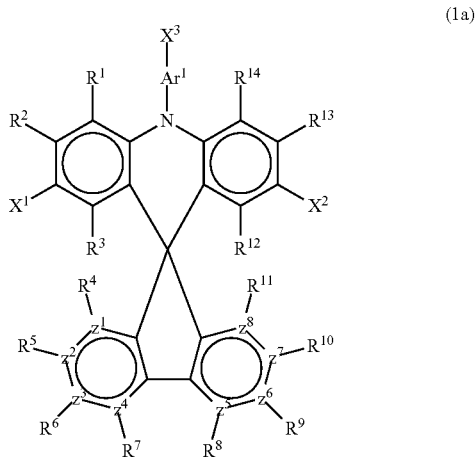

(1a)

In the formula, $X^1$, $X^2$, and $X^3$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein at least one of $X^1$, $X^2$, and $X^3$ is a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group.

$Ar^1$ represents a divalent group of a substituted or unsubstituted aromatic hydrocarbon, a divalent group of a substituted or unsubstituted aromatic heterocyclic ring, or a divalent group of a substituted or unsubstituted condensed polycyclic aromatic group, $R^1$ to $R^{14}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^{14}$ may bind to each other via a single bond, substituted or unsubstituted methylene, an oxygen atom, or a sulfur atom to form a ring.

$Z^1$ to $Z^8$ are carbon atoms or nitrogen atoms, wherein at least one of $Z^1$ to $Z^8$ is a nitrogen atom, and in this case the nitrogen atom does not have the hydrogen atom or the substituent of $R^4$ to $R^{11}$.

3) The present invention is a spiro compound having an azafluorene ring structure according to 1), the compound being represented by the following general formula (1-1).

[Chemical Formula 3]

(1-1)

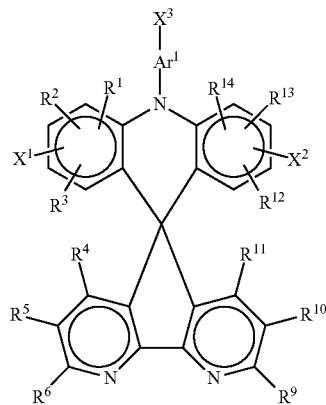

In the formula, $X^1$, $X^2$, and $X^3$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein at least one of $X^1$, $X^2$, and $X^3$ is a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group.

$Ar^1$ represents a divalent group of a substituted or unsubstituted aromatic hydrocarbon, a divalent group of a substituted or unsubstituted aromatic heterocyclic ring, or a divalent group of a substituted or unsubstituted condensed polycyclic aromatic group, $R^1$ to $R^6$, and $R^9$ to $R^{14}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^6$, and $R^9$ to $R^{14}$ may bind to each other via a single bond, substituted or unsubstituted methylene, an oxygen atom, or a sulfur atom to form a ring.

4) The present invention is a spiro compound having an azafluorene ring structure according to 1), the compound being represented by the following general formula (1a-1).

[Chemical Formula 4]

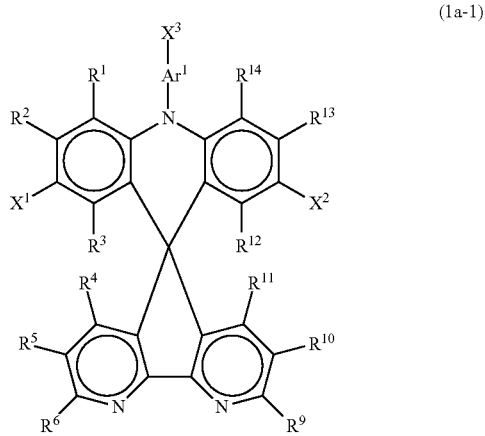

(1a-1)

In the formula, $X^1$, $X^2$, and $X^3$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein at least one of $X^1$, $X^2$, and $X^3$ is a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group.

$Ar^1$ represents a divalent group of a substituted or unsubstituted aromatic hydrocarbon, a divalent group of a substituted or unsubstituted aromatic heterocyclic ring, or a divalent group of a substituted or unsubstituted condensed polycyclic aromatic group, $R^1$ to $R^6$, and $R^9$ to $R^{14}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^6$, and $R^9$ to $R^{14}$ may bind to each other via a single bond, substituted or unsubstituted methylene, an oxygen atom, or a sulfur atom to form a ring.

5) The present invention is a spiro compound having an azafluorene ring structure according to 1), wherein $X^1$ in the general formula (1) is substituted or unsubstituted carbazolyl, substituted or unsubstituted phenoxazinyl, substituted or unsubstituted phenothiazinyl, substituted or unsubstituted acridinyl, substituted or unsubstituted phenazinyl, or a disubstituted amino group substituted with an aromatic hydrocarbon group or a condensed polycyclic aromatic group.

6) The present invention is a spiro compound having an azafluorene ring structure according to 1), wherein $X^2$ in the general formula (1) is substituted or unsubstituted carbazolyl, substituted or unsubstituted phenoxazinyl, substituted or unsubstituted phenothiazinyl, substituted or unsubstituted acridinyl, substituted or unsubstituted phenazinyl, or a disubstituted amino group substituted with an aromatic hydrocarbon group or a condensed polycyclic aromatic group.

7) The present invention is a spiro compound having an azafluorene ring structure according to 1), wherein $X^3$ in the general formula (1) is substituted or unsubstituted carbazolyl, substituted or unsubstituted phenoxazinyl, substituted or unsubstituted phenothiazinyl, substituted or unsubstituted acridinyl, substituted or unsubstituted phenazinyl, or a disubstituted amino group substituted with an aromatic hydrocarbon group or a condensed polycyclic aromatic group.

8) The present invention is a spiro compound having an azafluorene ring structure according to 1), wherein $X^1$ and $X^2$ in the general formula (1) represent substituted or unsubstituted carbazolyl, substituted or unsubstituted phenoxazinyl, substituted or unsubstituted phenothiazinyl, substituted or unsubstituted acridinyl, substituted or unsubstituted phenazinyl, or a disubstituted amino group substituted with an aromatic hydrocarbon group or a condensed polycyclic aromatic group.

9) The present invention is a spiro compound having an azafluorene ring structure according to 1), wherein $Ar^1$ in the general formula (1) is a divalent group of a substituted or unsubstituted aromatic hydrocarbon, or a divalent group of a substituted or unsubstituted condensed polycyclic aromatic group.

10) The present invention is a spiro compound having an azafluorene ring structure according to 1), wherein $X^3$ in the general formula (1) is a hydrogen atom.

11) The present invention is a spiro compound having an azafluorene ring structure according to 9) or 10), wherein $Ar^1$ in the general formula (1) is a divalent group of an unsubstituted aromatic hydrocarbon, or a divalent group of an unsubstituted condensed polycyclic aromatic group.

12) The present invention is a light-emitting material including the spiro compound having an azafluorene ring structure according to 1).

13) The present invention is a light-emitting material according to 12) that emits thermally activated delayed fluorescence.

14) The present invention is an organic electroluminescent device that includes a pair of electrodes, and one or more organic layers sandwiched between the pair of electrodes, wherein the spiro compound having an azafluorene ring structure according to 1) is used as a constituent material of at least one organic layer.

15) The present invention is an organic electroluminescent device according to 14) in which the organic layer is a light emitting layer.

16) The present invention is an organic electroluminescent device according to 15) in which the organic layer emits delayed fluorescence.

17) The present invention is an organic electroluminescent device according to 14) in which the organic layer is a hole transport layer.

18) The present invention is an organic electroluminescent device according to 14) in which the organic layer is an electron blocking layer.

Specific examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $X^1$, $X^2$, and $X^3$ in general formula (1) include methyl, ethyl, n-propyl, isopropyl, n-butyl, isobutyl, tert-butyl, n-pentyl, isopentyl, neopentyl, n-hexyl, cyclopentyl, cyclohexyl, 1-adamantyl, 2-adamantyl, vinyl, allyl, isopropenyl, and 2-butenyl.

Specific examples of the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $X^1$, $X^2$, and $X^3$ in general formula (1) include a deuterium atom, cyano, and nitro; halogen atoms such as a fluorine atom, a chlorine atom, a bromine atom, and an iodine atom; linear or branched alkyloxy of 1 to 6 carbon atoms such as methyloxy, ethyloxy, and propyloxy; alkenyl such as vinyl, and allyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; and aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, and carbolinyl. These substituents may be further substituted with the substituents exemplified above. These substituents may bind to each other via a single bond, substituted or unsubstituted methylene, an oxygen atom, or a sulfur atom to form a ring.

Specific examples of the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $X^1$, $X^2$, and $X^3$ in general formula (1) include methyloxy, ethyloxy, n-propyloxy, isopropyloxy, n-butyloxy, tert-butyloxy, n-pentyloxy, n-hexyloxy, cyclopentyloxy, cyclohexyloxy, cycloheptyloxy, cyclooctyloxy, 1-adamantyloxy, and 2-adamantyloxy.

Examples of the "substituent" in the "linear or branched alkyloxy of 1 to 6 carbon atoms having a substituent", or the "cycloalkyloxy of 5 to 10 carbon atoms having a substituent" represented by $X^1$, $X^2$, and $X^3$ in general formula (1) include the same groups exemplified for the "substituent" in the "linear or branched alkyl of 1 to 6 carbon atoms having a substituent", "cycloalkyl of 5 to 10 carbon atoms having a substituent", or "linear or branched alkenyl of 2 to 6 carbon atoms having a substituent" represented by $X^1$, $X^2$, and $X^3$ in general formula (1). The "substituent" may have the same forms exemplified above.

Specific examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $X^1$, $X^2$, and $X^3$ in general formula (1) include phenyl, biphenylyl, terphenylyl, naphthyl, anthracenyl, phenanthrenyl, fluorenyl, indenyl, pyrenyl, perylenyl, fluoranthenyl, triphenylenyl, pyridyl, pyrimidinyl, triazinyl, furyl, pyrrolyl, thienyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, acridinyl, phenazinyl, phenoxazinyl, phenoselenazinyl, phenothiazinyl, phenotellurazinyl, phenophosphazinyl, and carbolinyl.

Specific examples of the "substituent" in the "substituted aromatic hydrocarbon group", the "substituted aromatic heterocyclic group", or the "substituted condensed polycyclic aromatic group" represented by $X^1$, $X^2$, and $X^3$ in general formula include a deuterium atom, cyano, and nitro; halogen atoms such as a fluorine atom, a chlorine atom, a bromine atom, and an iodine atom; linear or branched alkyl of 1 to 6 carbon atoms such as methyl, ethyl, n-propyl, isopropyl, n-butyl, isobutyl, tert-butyl, n-pentyl, isopentyl, neopentyl, and n-hexyl; linear or branched alkyloxy of 1 to 6 carbon atoms such as methyloxy, ethyloxy, and propyloxy; alkenyl such as vinyl, and allyl; aryloxy such as phenyloxy, and tolyloxy; arylalkyloxy such as benzyloxy, and phenethyloxy; aromatic hydrocarbon groups or condensed polycyclic aromatic groups such as phenyl, biphenylyl, terphenylyl, naphthyl, anthracenyl, phenanthrenyl, fluorenyl, indenyl, pyrenyl, perylenyl, fluoranthenyl, and triphenylenyl; aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzooxazolyl, benzothiazolyl, quinoxalinyl, benzoimidazolyl, pyrazolyl, dibenzofuranyl, dibenzothienyl, phenoxazinyl, phenothiazinyl, and carbolinyl; arylvinyl such as styryl, and naphthylvinyl; acyl such as acetyl, and benzoyl; dialkylamino groups such as dimethylamino, and diethylamino; disubstituted amino groups substituted with an aromatic hydrocarbon group or a condensed polycyclic aromatic group, such as diphenylamino, and dinaphthylamino; diaralkylamino groups such as dibenzylamino, and diphenethylamino; disubstituted amino groups substituted with an aromatic heterocyclic group, such as dipyridylamino, and dithienylamino; dialkenylamino groups such as diallylamino; and disubstituted amino groups substituted with a substituent selected from alkyl, an aromatic hydrocarbon group, a condensed polycyclic aromatic group, aralkyl, an aromatic heterocyclic group, and alkenyl. These substituents may be further substituted with the substituents exemplified above. These substituents may bind to each other via a single bond, substituted or unsubstituted methylene, an oxygen atom, or a sulfur atom to form a ring.

Specific examples of the "aryloxy" in the "substituted or unsubstituted aryloxy" represented by $X^1$, $X^2$, and $X^3$ in general formula (1) include phenyloxy, biphenylyloxy, terphenylyloxy, naphthyloxy, anthracenyloxy, phenanthrenyloxy, fluorenyloxy, indenyloxy, pyrenyloxy, and perylenyloxy.

Examples of the "substituent" in the "substituted aryloxy" represented by $X^1$, $X^2$, and $X^3$ in general formula (1) include the same groups exemplified for the "substituent" in the "substituted aromatic hydrocarbon group", the "substituted aromatic heterocyclic group", or the "substituted condensed polycyclic aromatic group" represented by $X^1$, $X^2$, and $X^3$ in general formula (1). The "substituent" may have the same forms exemplified above.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" represented by $X^1$, $X^2$, and $X^3$ in general formula (1) include the same groups exemplified for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $X^1$, $X^2$, and $X^3$ in general formula (1). These groups may have a substituent. Examples of the substituent include the same groups exemplified for the "substituent" in the "substituted aromatic hydrocarbon group", the "substituted aromatic heterocyclic group", or the "substituted condensed polycyclic aromatic group" represented by $X^1$, $X^2$, and $X^3$ in the general formula (1). The "substituent" may have the same forms exemplified above.

$X^1$ and $X^2$ in general formula (1) preferably represent "a disubstituted amino group substituted with a group selected from an aromatic hydrocarbon group, an aromatic heterocyclic group, and a condensed polycyclic aromatic group, or an aromatic hydrocarbon group having an aromatic heterocyclic group as a substituent", "a substituted or unsubstituted aromatic heterocyclic group", "a substituted or unsubstituted condensed polycyclic aromatic group", or "a disubstituted amino group substituted with a group selected from an aromatic hydrocarbon group, an aromatic heterocyclic group, and a condensed polycyclic aromatic group". More preferably, $X^1$ and $X^2$ in general formula (1) represent "a substituted or unsubstituted aromatic heterocyclic group", or "a disubstituted amino group substituted with a group selected from an aromatic hydrocarbon group, an aromatic heterocyclic group, and a condensed polycyclic aromatic group". Particularly preferably, $X^1$ and $X^2$ in general formula (1) represent carbazolyl, phenoxazinyl, phenothiazinyl, acridinyl, phenazinyl, or "a disubstituted amino group substituted with an aromatic hydrocarbon group, or a condensed polycyclic aromatic group".

The substituents of these groups are preferably carbazolyl, or disubstituted amino groups substituted with an aromatic hydrocarbon group, more preferably carbazolyl, or diphenylamino groups.

$X^3$ in general formula (1) is preferably a hydrogen atom, "a disubstituted amino group substituted with a group selected from an aromatic hydrocarbon group, an aromatic heterocyclic group, and a condensed polycyclic aromatic group, or an aromatic hydrocarbon group having an aromatic heterocyclic group as a substituent", "a substituted or unsubstituted aromatic heterocyclic group", "a substituted or unsubstituted condensed polycyclic aromatic group", or "a disubstituted amino group substituted with a group selected from an aromatic hydrocarbon group, an aromatic heterocyclic group, and a condensed polycyclic aromatic group". More preferably, $X^3$ in general formula (1) is a hydrogen atom, "a substituted or unsubstituted aromatic heterocyclic group", or "a disubstituted amino group substituted with a group selected from an aromatic hydrocarbon group, an aromatic heterocyclic group, and a condensed polycyclic aromatic group". Particularly preferably, $X^3$ in general formula (1) is a hydrogen atom, carbazolyl, phenoxazinyl, phenothiazinyl, acridinyl, phenazinyl, or "a disubstituted amino group substituted with an aromatic hydrocarbon group or a condensed polycyclic aromatic group".

When these groups have a substituent, the substituent is preferably carbazolyl, or a disubstituted amino group substituted with an aromatic hydrocarbon group, more preferably carbazolyl, or a diphenylamino group.

Specific examples of the "aromatic hydrocarbon group", the "aromatic heterocyclic ring", or the "condensed polycyclic aromatic group" of the "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic group" represented by $Ar^1$ in general formula (1) include benzene, biphenyl, terphenyl, tetrakisphenyl, styrene, naphthalene, anthracene, acenaphthylene, fluorene, phenanthrene, indane, pyrene, pyridine, pyrimidine, triazine, furan, pyrrole, thiophene, quinoline, isoquinoline, benzofuran, benzothiophene, indoline, carbazole, carboline, benzooxazole, benzothiazole, quinoxaline, benzoimidazole, pyrazole, dibenzofuran, dibenzothiophene, naphthyridine, phenanthroline, and acridine.

The "divalent group of a substituted or unsubstituted aromatic hydrocarbon", the "divalent group of a substituted or unsubstituted aromatic heterocyclic ring", or the "divalent group of a substituted or unsubstituted condensed polycyclic aromatic group" represented by $Ar^1$ in general formula (1) represents a divalent group that results from removal of two hydrogen atoms from the "aromatic hydrocarbon group", the "aromatic heterocyclic ring", or the "condensed polycyclic aromatic group".

Examples of the "substituent" in the "divalent group of a substituted aromatic hydrocarbon group", the "divalent group of a substituted aromatic heterocyclic ring", or the "divalent group of a substituted condensed polycyclic aromatic group" represented by $Ar^1$ in general formula (1) include the same groups exemplified for the "substituent" in the "substituted aromatic hydrocarbon group", the "substituted aromatic heterocyclic group", or the "substituted condensed polycyclic aromatic group" represented by $X^1$, $X^2$, and $X^3$ in the general formula (1). The "substituent" may have the same forms exemplified above.

$Ar^1$ in general formula (1) is preferably "a divalent group of a substituted or unsubstituted aromatic hydrocarbon", or "a divalent group of a substituted or unsubstituted condensed polycyclic aromatic group", more preferably "a divalent group of unsubstituted aromatic hydrocarbon group", or "a divalent group of an unsubstituted condensed polycyclic aromatic group".

Examples of the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $R^1$ to $R^{14}$ in general formula (1) include the same groups exemplified for the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $X^1$, $X^2$, and $X^3$ in the general formula (1). These groups may bind to each other via a single bond, substituted or unsubstituted methylene, an oxygen atom, or a sulfur atom to form a ring.

Examples of the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $R^1$ to $R^{14}$ in general formula (1) include the same groups exemplified for the "substituent" in the "linear or branched alkyl of 1 to 6 carbon atoms having a substituent", the "cycloalkyl of 5 to 10 carbon atoms having a substituent", or the "linear or branched alkenyl of 2 to 6 carbon atoms having a substituent" represented by $X^1$, $X^2$, and $X^3$ in the general formula (1). The "substituent" may have the same forms exemplified above.

Examples of the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $R^1$ to $R^{14}$ in general formula (1) include the same groups exemplified for the "linear or branched alkyloxy of 1 to 6 carbon atoms", or the "cycloalkyloxy of 5 to 10 carbon atoms" in the "linear or branched alkyloxy of 1 to 6 carbon atoms that may have a substituent", or the "cycloalkyloxy of 5 to 10 carbon atoms that may have a substituent" represented by $X^1$, $X^2$, and $X^3$ in the general formula (1). These groups may bind to each other via a single bond, substituted or unsubstituted methylene, an oxygen atom, or a sulfur atom to form a ring.

Examples of the "substituent" in the "linear or branched alkyloxy of 1 to 6 carbon atoms having a substituent", or the "cycloalkyloxy of 5 to 10 carbon atoms having a substituent" represented by $R^1$ to $R^{14}$ in general formula (1) include the same groups exemplified for the "linear or branched alkyl of 1 to 6 carbon atoms", the "cycloalkyl of 5 to 10 carbon atoms", or the "linear or branched alkenyl of 2 to 6 carbon atoms" in the "linear or branched alkyl of 1 to 6 carbon atoms that may have a substituent", the "cycloalkyl of 5 to 10 carbon atoms that may have a substituent", or the "linear or branched alkenyl of 2 to 6 carbon atoms that may have a substituent" represented by $X^1$, $X^2$, and $X^3$ in the general formula (1). These groups may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $R^1$ to $R^{14}$ in general formula (1) include the same groups exemplified for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $X^1$, $X^2$, and $X^3$ in the general formula (1). These groups may bind to each other via a single bond, substituted or unsubstituted methylene, an oxygen atom, or a sulfur atom to form a ring.

Examples of the "substituent" in the "substituted aromatic hydrocarbon group", the "substituted aromatic heterocyclic group", or the "substituted condensed polycyclic aromatic group" represented by $R^1$ to $R^{14}$ in general formula (1) include the same groups exemplified for the "substituent" in the "substituted aromatic hydrocarbon group", the "substituted aromatic heterocyclic group", or the "substituted condensed polycyclic aromatic group" represented by $X^1$, $X^2$, and $X^3$ in the general formula (1). The "substituent" may have the same forms exemplified above.

Examples of the "aryloxy" in the "substituted or unsubstituted aryloxy" represented by $R^1$ to $R^{14}$ in general formula (1) include the same groups exemplified for the "aryloxy" in the "substituted or unsubstituted aryloxy" represented by $X^1$, $X^2$, and $X^3$ in the general formula (1). These groups may bind to each other via a single bond, substituted or unsubstituted methylene, an oxygen atom, or a sulfur atom to form a ring.

Examples of the "substituent" in the "substituted aryloxy" represented by $R^1$ to $R^{14}$ in general formula (1) include the same groups exemplified for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $X^1$, $X^2$, and $X^3$ in the general formula (1). These groups may bind to each other via a single bond, substituted or unsubstituted methylene, an oxygen atom, or a sulfur atom to form a ring.

Examples of the "aromatic hydrocarbon group", the "aromatic heterocyclic group", or the "condensed polycyclic aromatic group" in the "disubstituted amino group substituted with a group selected from an aromatic hydrocarbon group, an aromatic heterocyclic group, and a condensed polycyclic aromatic group" represented by $R^1$ to $R^{14}$ in general formula (1) include the same groups exemplified for the "aromatic hydrocarbon group", the "aromatic heterocyclic group", or the "condensed polycyclic aromatic group" in the "substituted or unsubstituted aromatic hydrocarbon group", the "substituted or unsubstituted aromatic heterocyclic group", or the "substituted or unsubstituted condensed polycyclic aromatic group" represented by $X^1$, $X^2$, and $X^3$ in the general formula (1). These groups may have a substituent. Examples of the substituent include the same groups exemplified for the "substituent" in the "substituted aromatic hydrocarbon group", the "substituted aromatic heterocyclic group", or the "substituted condensed polycyclic aromatic group" represented by $X^1$, $X^2$, and $X^3$ in the general formula (1). The "substituent" may have the same forms exemplified above.

In general formula (1), at least one of $X^1$, $X^2$, and $X^3$ (i.e., any one of $X^1$, $X^2$, and $X^3$, any two of $X^1$, $X^2$, and $X^3$, or all of $X^1$, $X^2$, and $X^3$) is a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group.

In general formula (1), it is preferable to take the form in which $X^1$ and $X^2$ represent a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group, or the form in which only $X^3$ is a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group. In a more preferred form, $X^1$ and $X^2$ represent a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group.

In general formula (1), $Z^1$ to $Z^8$ are carbon atoms or nitrogen atoms, wherein at least one of $Z^1$ to $Z^8$ is a nitrogen atom. In this case, the nitrogen atom does not have the hydrogen atom or the substituent of $R^4$ to $R^{11}$ ($R^4$ when $Z^1$ is a nitrogen atom, $R^5$ when $Z^2$ is a nitrogen atom, $R^6$ when $Z^3$ is a nitrogen atom, $R^7$ when $Z^4$ is a nitrogen atom, $R^8$ when $Z^5$ is a nitrogen atom, $R^9$ when $Z^6$ is a nitrogen atom, $R^{10}$ when $Z^7$ is a nitrogen atom, and $R^{11}$ when $Z^8$ is a nitrogen atom).

In general formula (1), it is preferable to take the form in which $Z^4$ and $Z^5$ are nitrogen atoms. (In this case, $Z^4$ and $Z^5$ do not have the hydrogen atom or the substituent of $R^7$ and $R^8$, meaning that $R^7$ and $R^8$ do not exist.)

The spiro compounds of the general formula (1) having an azafluorene ring structure of the present invention can emit delayed fluorescence and have a stable thin-film state as well as high luminous efficiency because of a small difference between excited triplet energy and excited singlet energy ($\Delta E_{ST}$), and a comparatively high oscillator strength (f) which are obtained by theoretical calculation.

The spiro compounds of the general formula (1) having an azafluorene ring structure of the present invention can be used as a constituent material of the light emitting layer of an organic electroluminescent device (hereinafter also referred to as an organic EL device). With the use of the compounds of the present invention that emit delayed fluorescence, the luminous efficiency dramatically improves.

The spiro compounds of the general formula (1) having an azafluorene ring structure of the present invention can be used as a constituent material of the hole transport layer of an organic EL device. By using the material having higher hole mobility and higher electron blocking performance with improved stability against electrons than conventional materials, the generated excitons in the light emitting layer can be confined, and the probability of hole and electron recombination can improve, making it possible to obtain high luminous efficiency, and to lower the driving voltage, and improve the durability of the organic EL device.

The Spiro compounds of the general formula (1) having an azafluorene ring structure of the present invention can also be used as a constituent material of the electron blocking layer of an organic EL device. By using the material having an excellent electron blocking ability and superior hole transportability and higher stability in the thin-film state than conventional materials, it is possible to lower the driving voltage and improve the current resistance while maintaining high luminous efficiency, thereby improving the maximum emission luminance of the organic EL device.

Effects of the Invention

The spiro compounds of the general formula (1) having an azafluorene ring structure of the present invention are useful as a light-emitting material (a dopant compound) of the light emitting layer of an organic EL device, or as a constituent material of the hole transport layer or the electron blocking layer of an organic EL device. The spiro compounds can emit delayed fluorescence, and have a stable thin-film state with excellent heat resistance. An organic EL device produced by using the spiro compounds can have high efficiency, high luminance, and low driving voltage.

MODE FOR CARRYING OUT THE INVENTION

Figure 1:
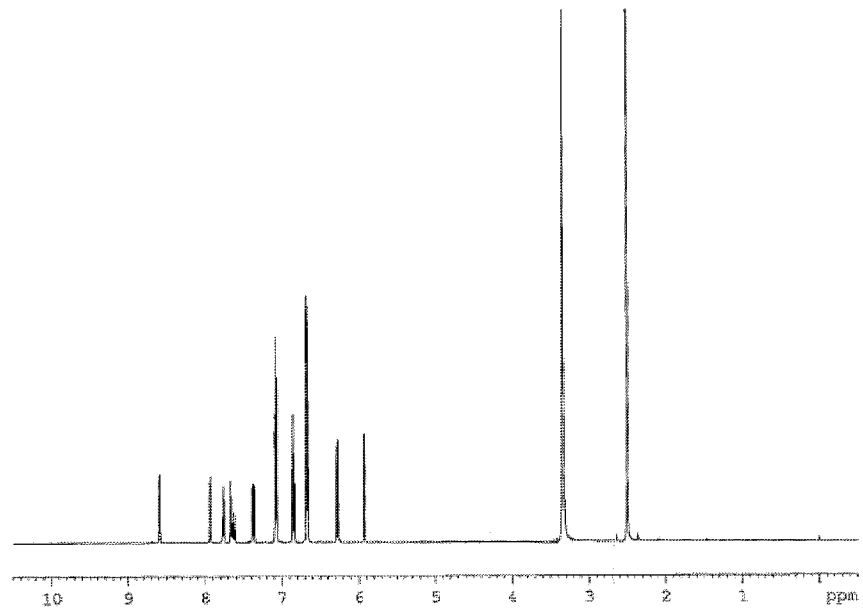
FIG. 1 is a $^1$H-NMR chart of the compound of Example 1 of the present invention (Compound 1).

The spiro compounds of general formula (1) having an azafluorene ring structure of the present invention are novel compounds, and can be synthesized, for example, as follows. A halogen-substituted triarylamine is reacted first with a Grignard reagent, and then with azafluorenone to synthesize a carbinol product. The carbinol product is then subjected to a ring-closing reaction using an acid catalyst or the like to synthesize a spiro compound having an azafluorene ring structure.

This spiro compound having an azafluorene ring structure may be brominated with a compound such as N-bromosuccinimide to synthesize a bromo-substituted product, which is then reacted with various diarylamines in Buchwald-Hartwig reaction or other condensation reactions to synthesize the spiro compound having an azafluorene ring structure of the present invention.

The spiro compound having an azafluorene ring structure of the present invention also can be synthesized by reacting the bromo-substituted product with various boronic acids or borates in a cross-coupling reaction such as Suzuki coupling (refer to Non-Patent Document 2, for example).

The following presents specific examples of preferred compounds among the spiro compounds of general formula (1) having an azafluorene ring structure. The present invention, however, is not restricted to these compounds.

[Chemical Formula 5]

(Compound 1)

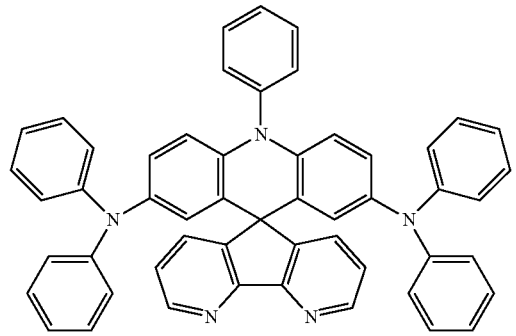

-continued
[Chemical Formula 6]
(Compound 2)
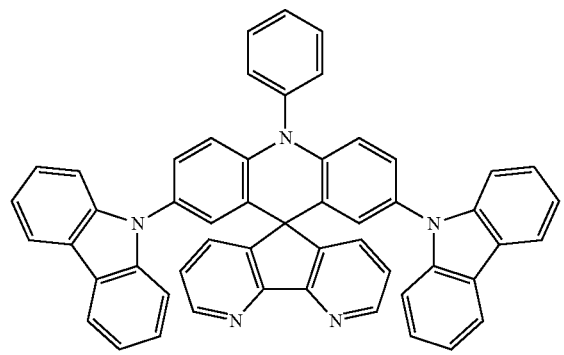
[Chemical Formula 7]
(Compound 3)
[Chemical Formula 8]
(Compound 4)
[Chemical Formula 9]
(Compound 5)
-continued
[Chemical Formula 10]
(Compound 6)
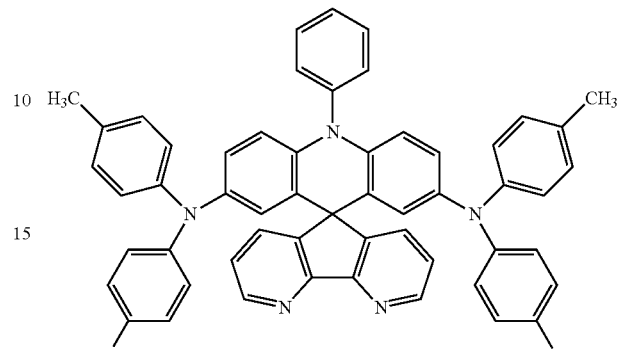
[Chemical Formula 11]
(Compound 7)
[Chemical Formula 12]
(Compound 8)
[Chemical Formula 13]
(Compound 9)

[Chemical Formula 14]
(Compound 10)
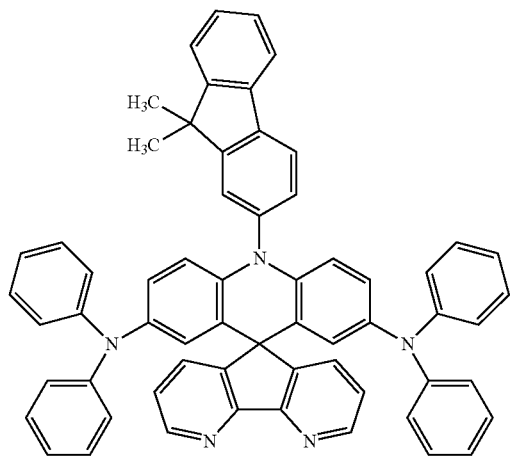
[Chemical Formula 15]
(Compound 11)
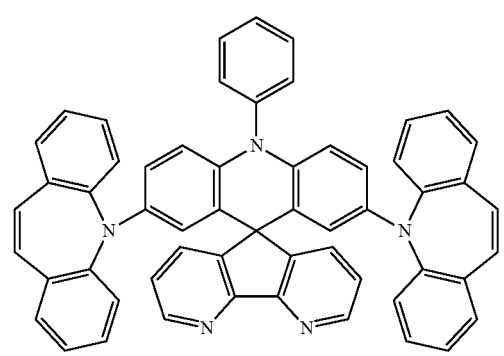
[Chemical Formula 16]
(Compound 12)
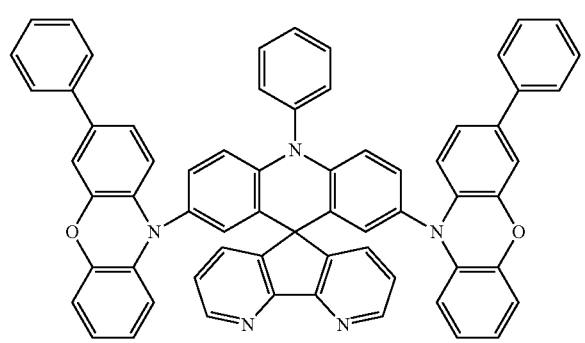
[Chemical Formula 17]
(Compound 13)
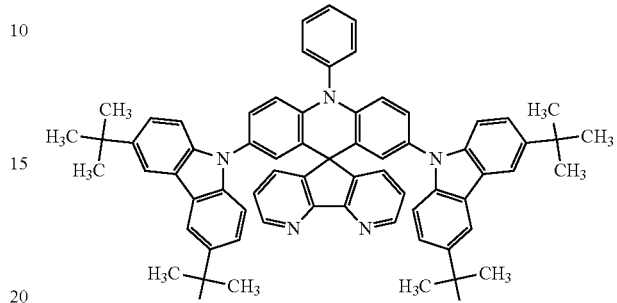
[Chemical Formula 18]
(Compound 14)
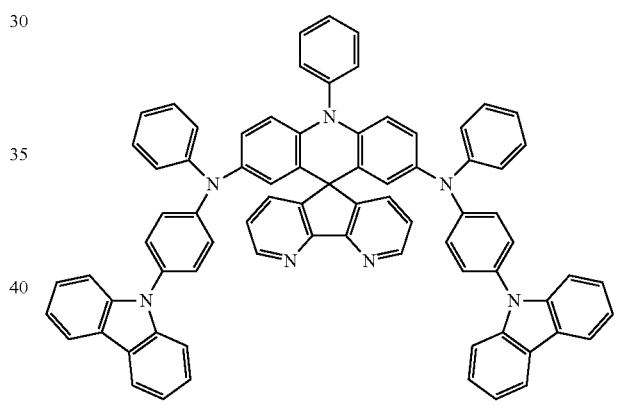
[Chemical Formula 19]
(Compound 15)
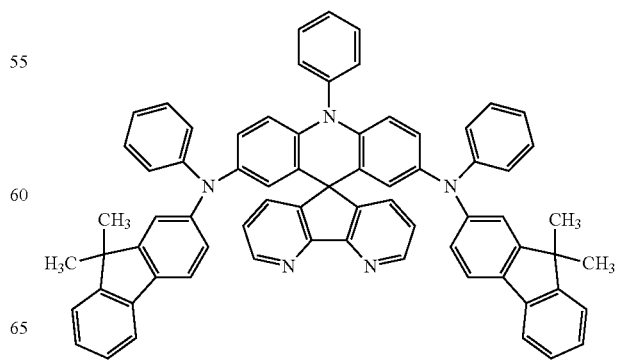

[Chemical Formula 20]

(Compound 16)

[Chemical Formula 21]

(Compound 17)

[Chemical Formula 22]

(Compound 18)

[Chemical Formula 23]

(Compound 19)

[Chemical Formula 24]

(Compound 20)

[Chemical Formula 25]

(Compound 21)

-continued
[Chemical Formula 26]
(Compound 22)
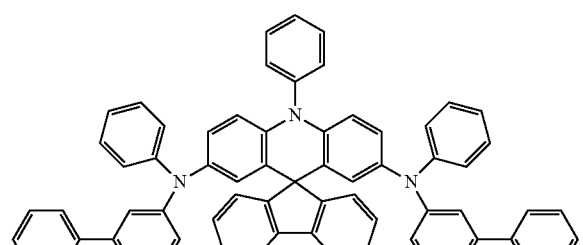
[Chemical Formula 27]
(Compound 23)
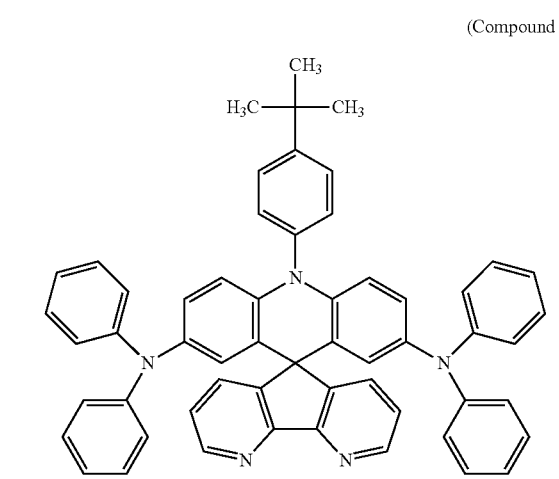
[Chemical Formula 28]
(Compound 24)
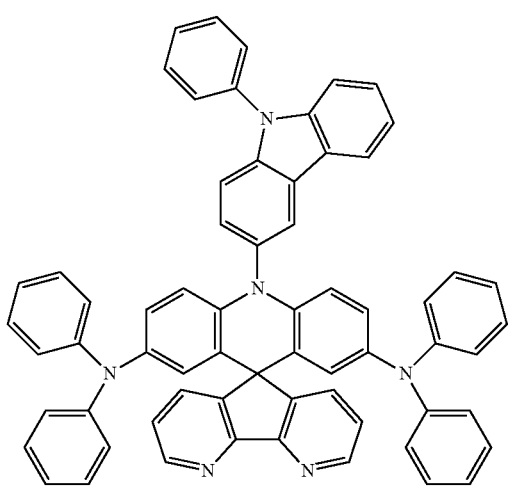
[Chemical Formula 29]
(Compound 25)
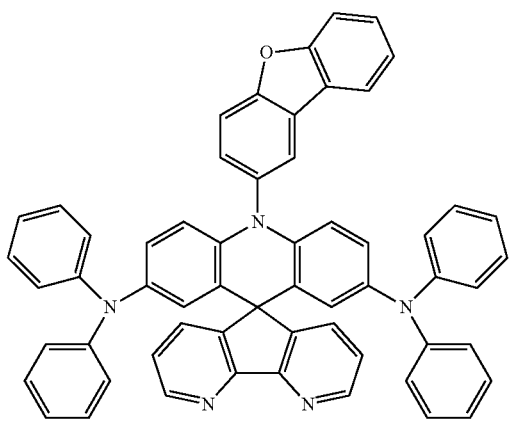
[Chemical Formula 30]
(Compound 26)
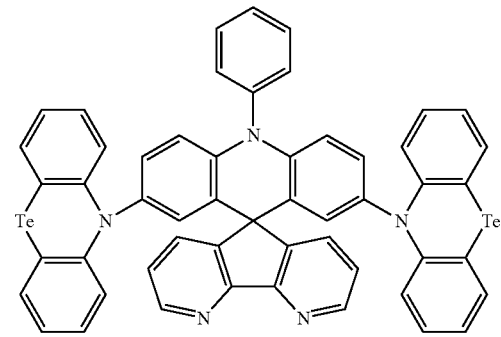
[Chemical Formula 31]
(Compound 27)
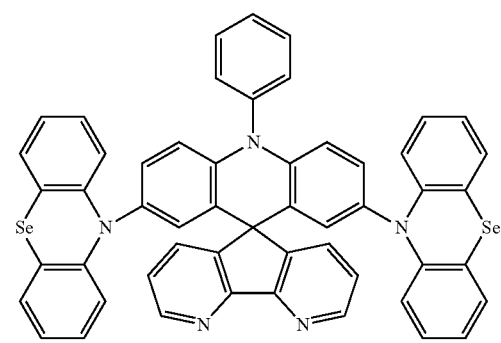

-continued
[Chemical Formula 32]
(Compound 28)
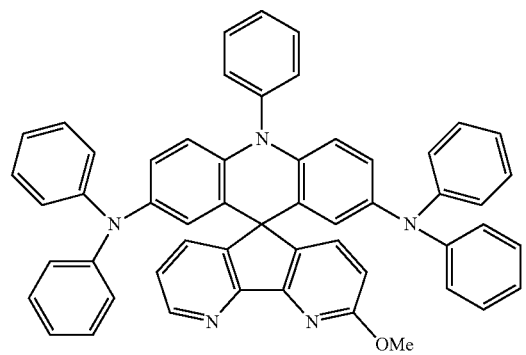
[Chemical Formula 33]
(Compound 29)
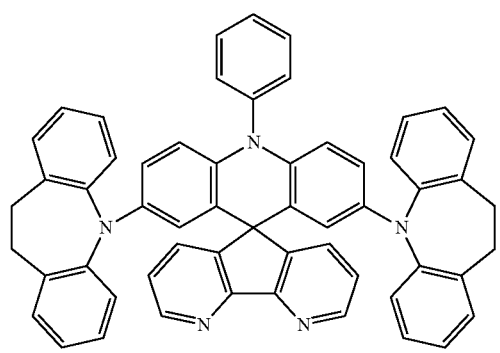
[Chemical Formula 34]
(Compound 30)
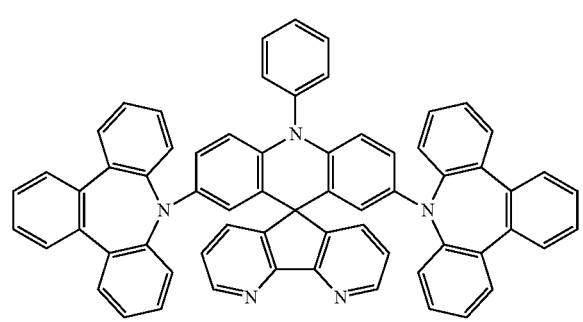
[Chemical Formula 35]
(Compound 31)
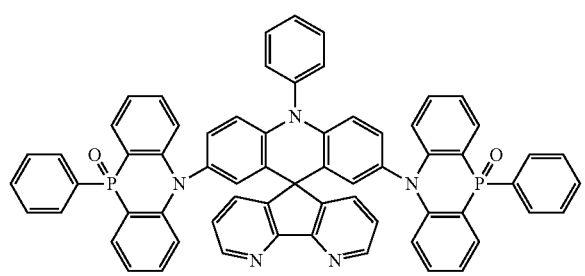
-continued
[Chemical Formula 36]
(Compound 32)
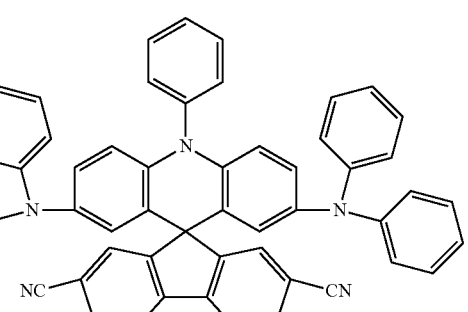
[Chemical Formula 37]
(Compound 33)
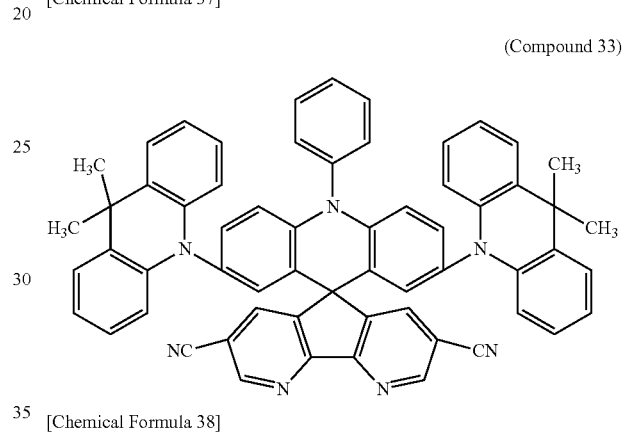
[Chemical Formula 38]
(Compound 34)
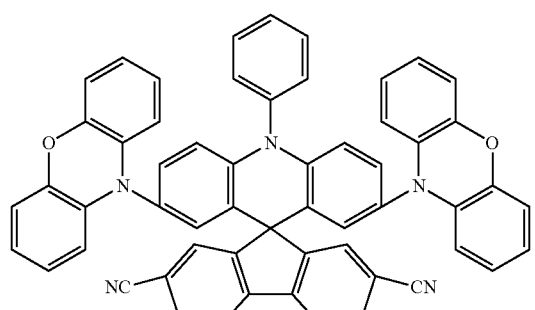
[Chemical Formula 39]
(Compound 35)
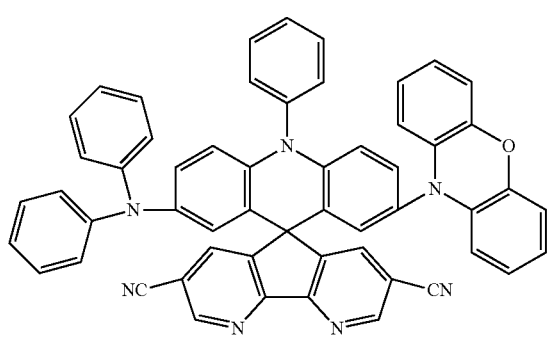

[Chemical Formula 40]
(Compound 36)
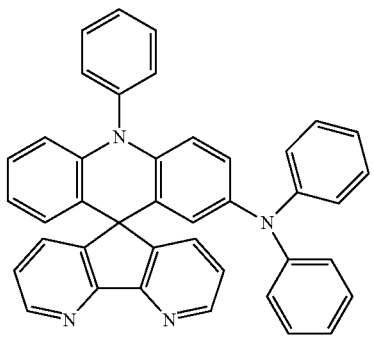
[Chemical Formula 41]
(Compound 37)
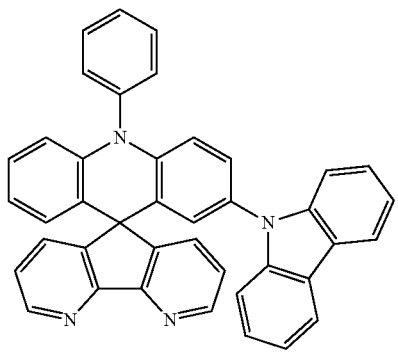
[Chemical Formula 42]
(Compound 38)
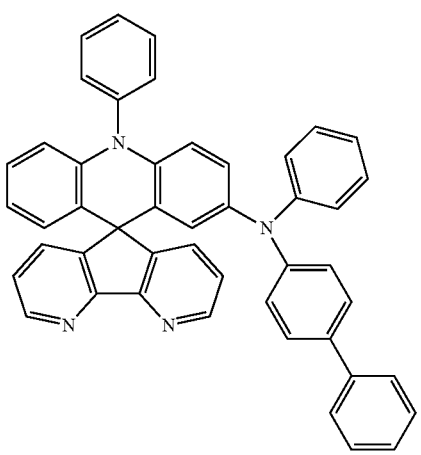
[Chemical Formula 43]
(Compound 39)
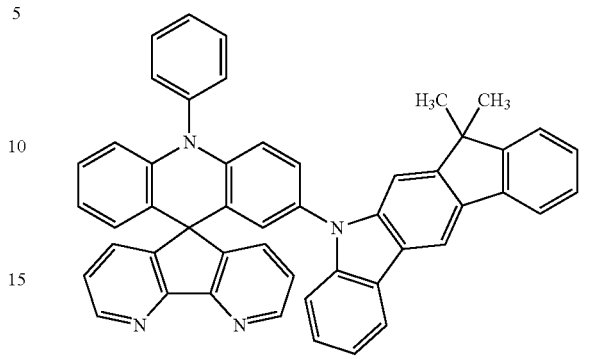
[Chemical Formula 44]
(Compound 40)
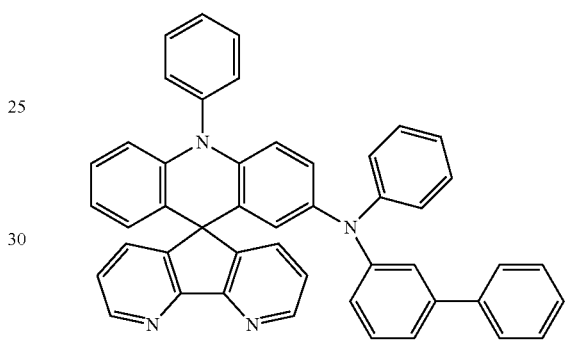
[Chemical Formula 45]
(Compound 41)
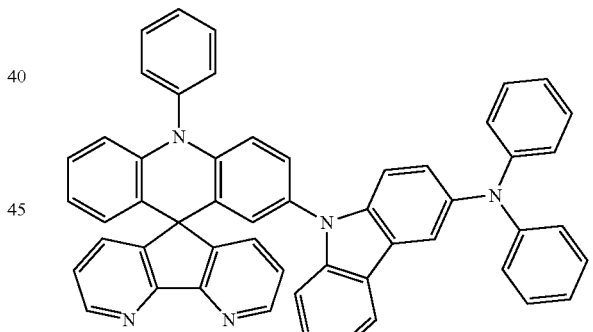
[Chemical Formula 46]
(Compound 42)
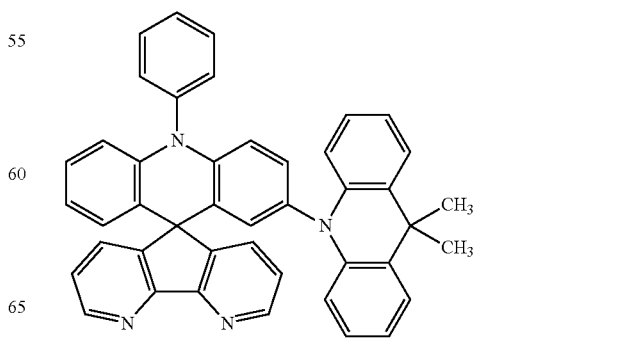

[Chemical Formula 47]
(Compound 43)
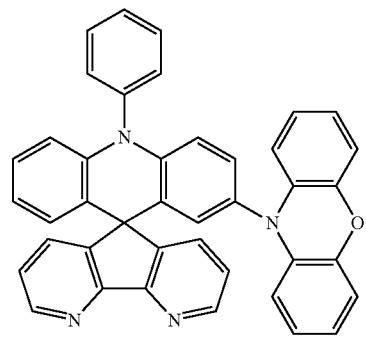
[Chemical Formula 48]
(Compound 44)
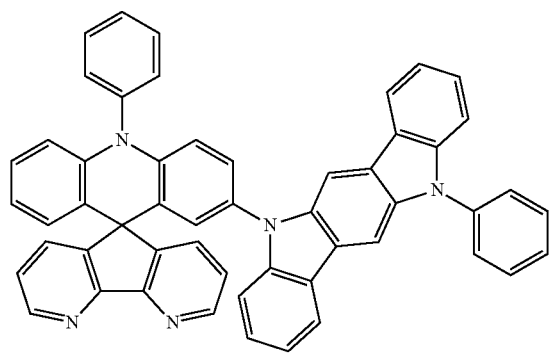
[Chemical Formula 49]
(Compound 45)
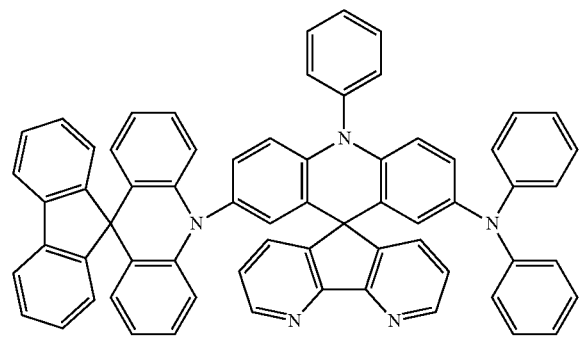
[Chemical Formula 50]
(Compound 46)
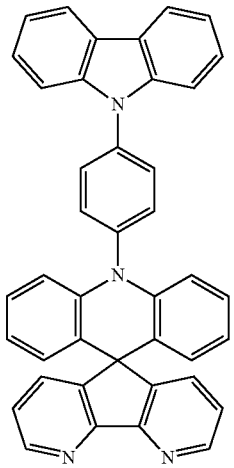
[Chemical Formula 51]
(Compound 47)
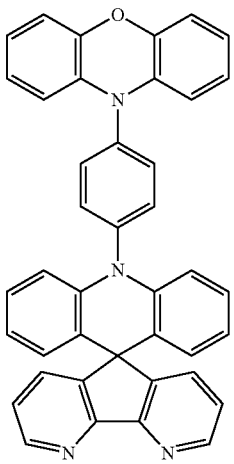
[Chemical Formula 52]
(Compound 48)
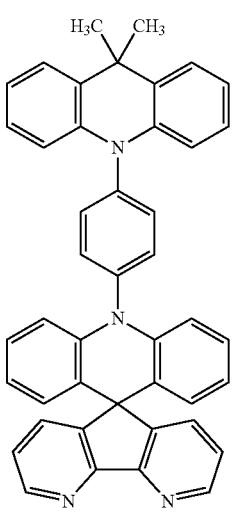

[Chemical Formula 53]
(Compound 49)
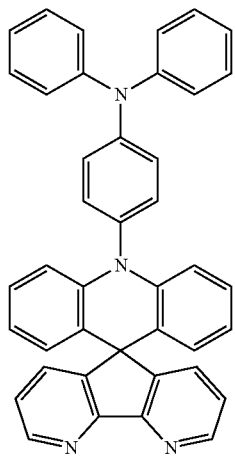
[Chemical Formula 54]
(Compound 50)
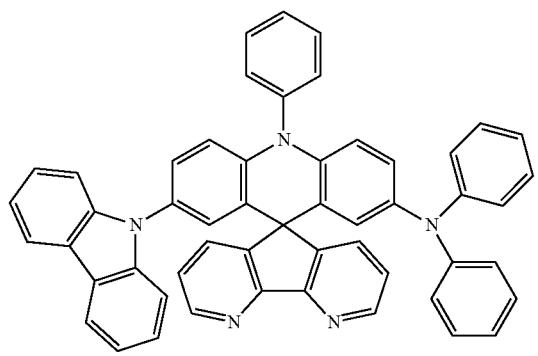
[Chemical Formula 55]
(Compound 51)
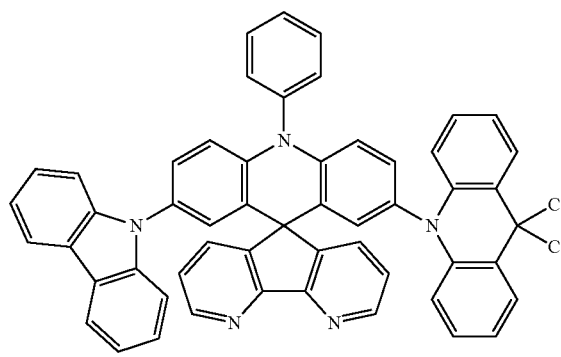
[Chemical Formula 56]
(Compound 52)
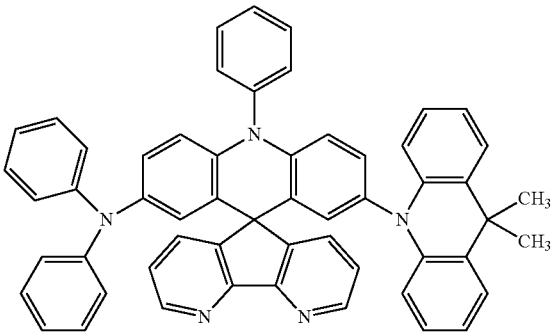
[Chemical Formula 57]
(Compound 53)
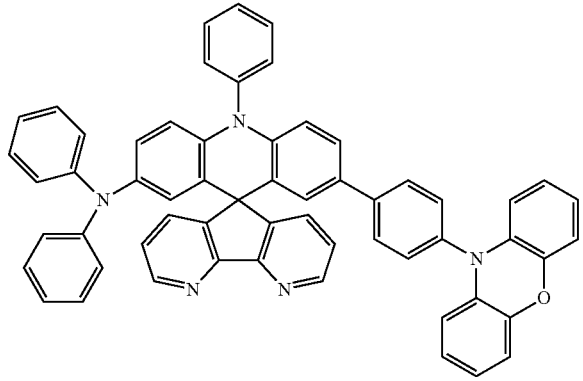
[Chemical Formula 58]
(Compound 54)
[Chemical Formula 59]
(Compound 55)
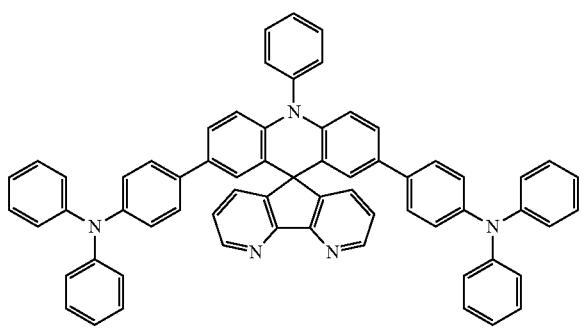

[Chemical Formula 60]
(Compound 56)
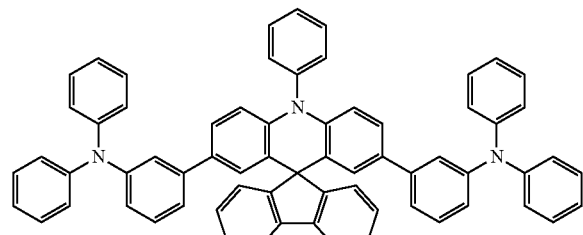
[Chemical Formula 61]
(Compound 57)
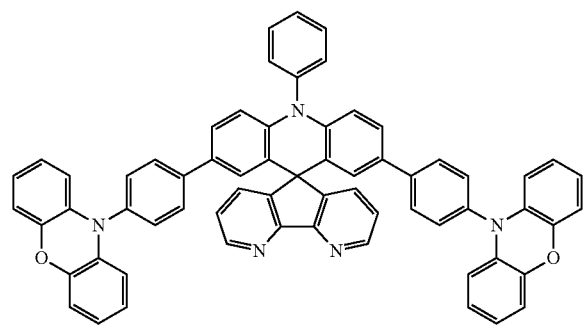
[Chemical Formula 62]
(Compound 58)
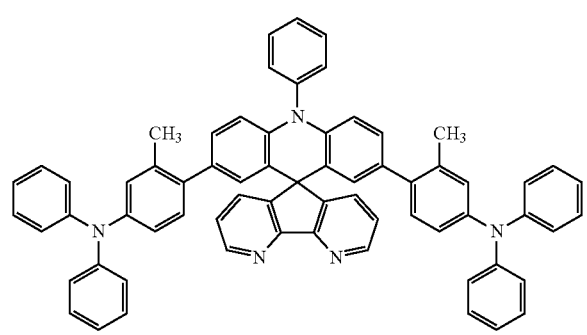
[Chemical Formula 63]
(Compound 59)
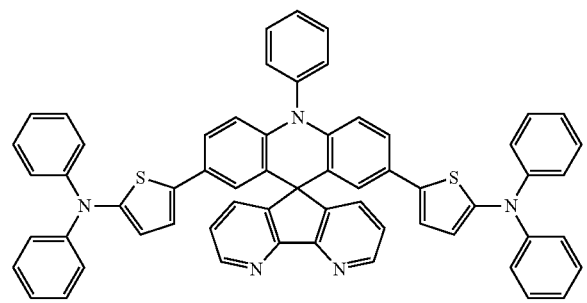
[Chemical Formula 64]
(Compound 60)
[Chemical Formula 65]
(Compound 61)
[Chemical Formula 66]
(Compound 62)
[Chemical Formula 67]
(Compound 63)

[Chemical Formula 68]
(Compound 64)
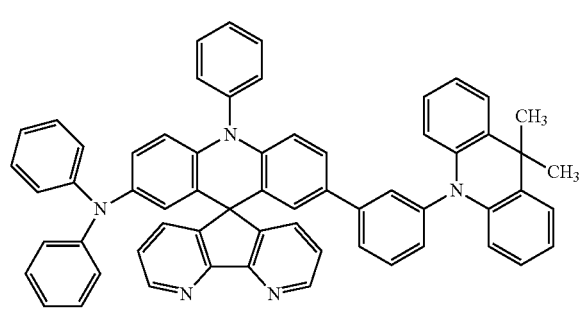
[Chemical Formula 69]
(Compound 65)
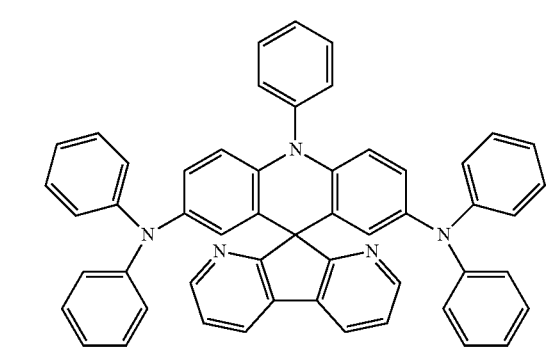
[Chemical Formula 70]
(Compound 66)
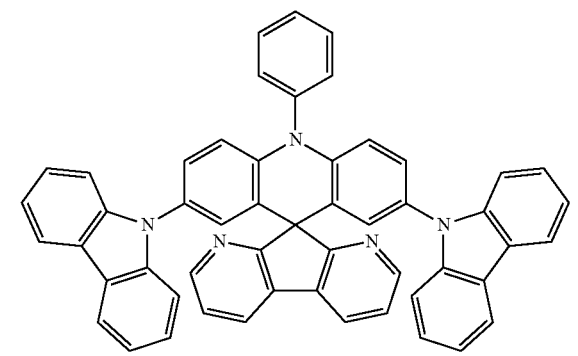
[Chemical Formula 71]
(Compound 67)
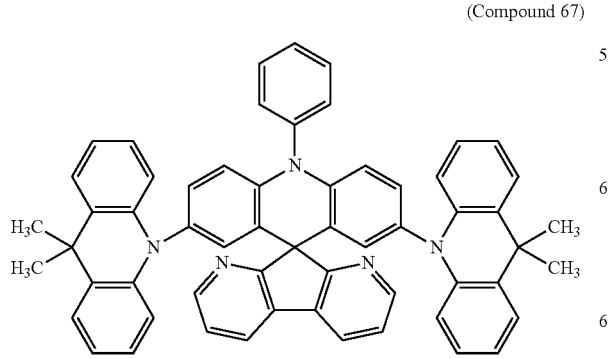
[Chemical Formula 72]
(Compound 68)
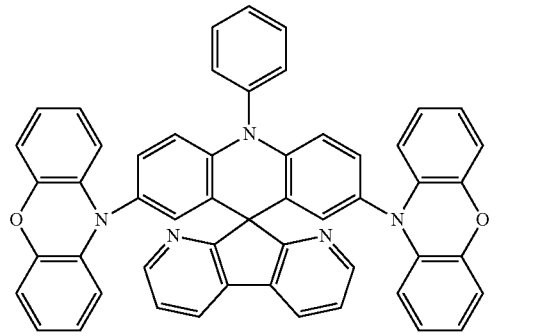
[Chemical Formula 73]
(Compound 69)
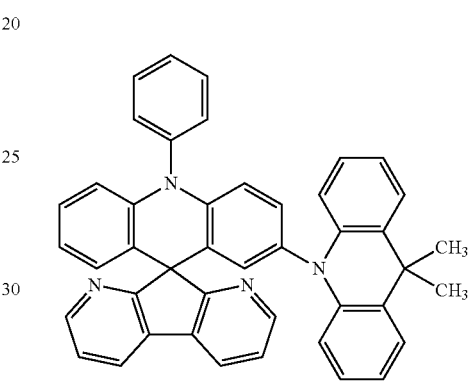
[Chemical Formula 74]
(Compound 70)
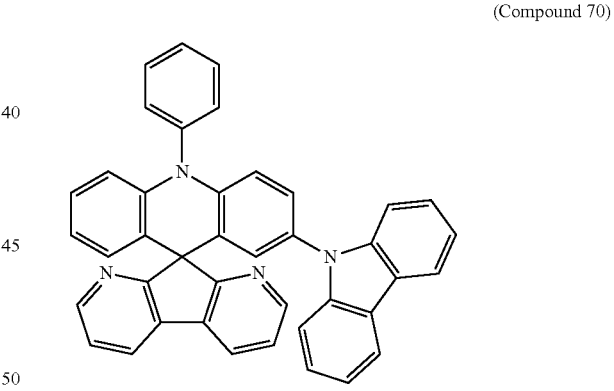
[Chemical Formula 75]
(Compound 71)
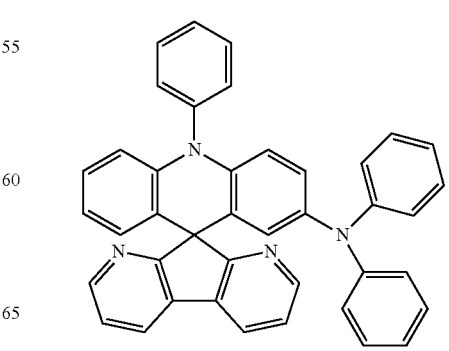

[Chemical Formula 76]
(Compound 72)
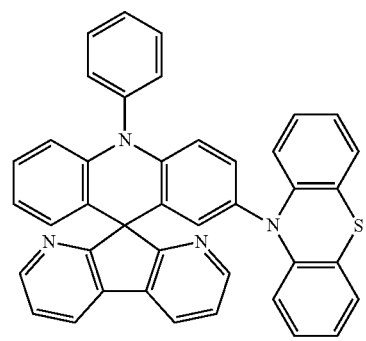
[Chemical Formula 77]
(Compound 73)
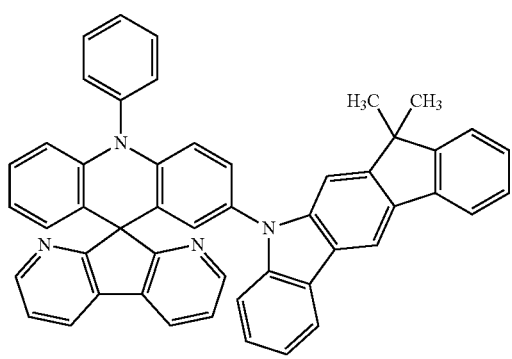
[Chemical Formula 78]
(Compound 74)
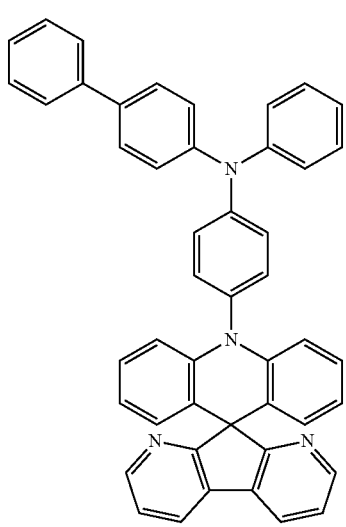
[Chemical Formula 79]
(Compound 75)
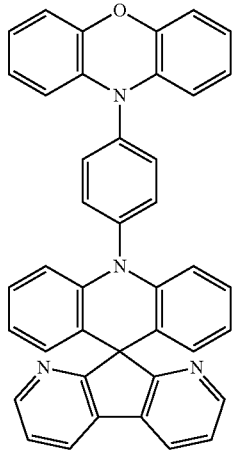
[Chemical Formula 80]
(Compound 76)
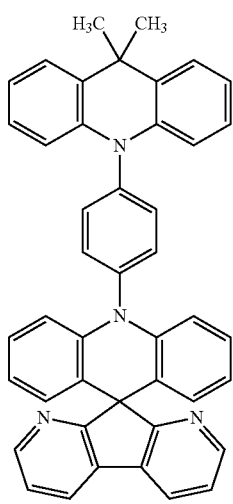
[Chemical Formula 81]
(Compound 77)
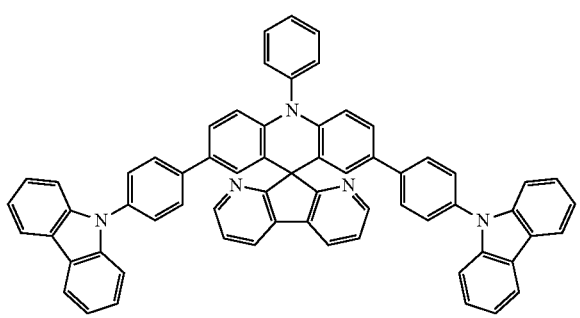

[Chemical Formula 82]
(Compound 78)
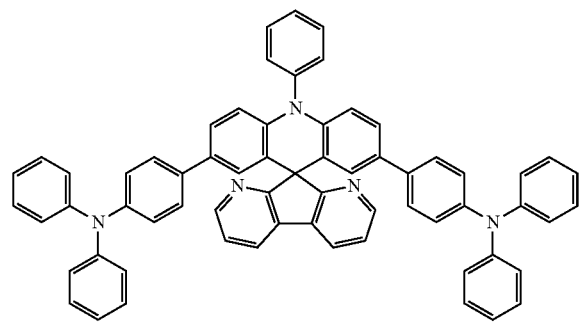
[Chemical Formula 83]
(Compound 79)
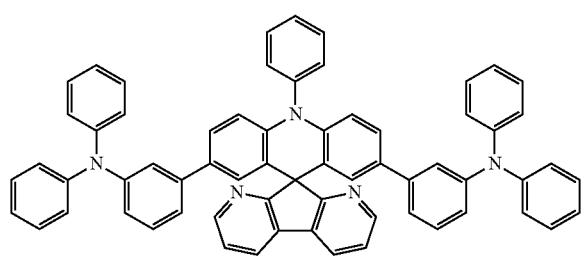
[Chemical Formula 84]
(Compound 80)
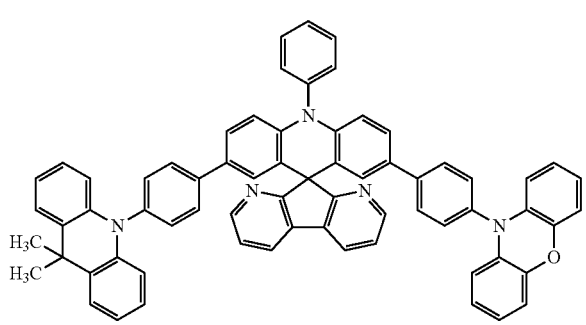
[Chemical Formula 85]
(Compound 81)
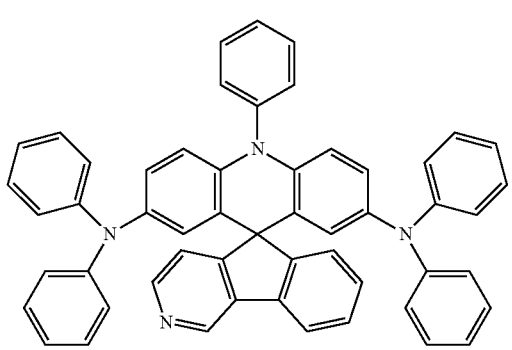
[Chemical Formula 86]
(Compound 82)
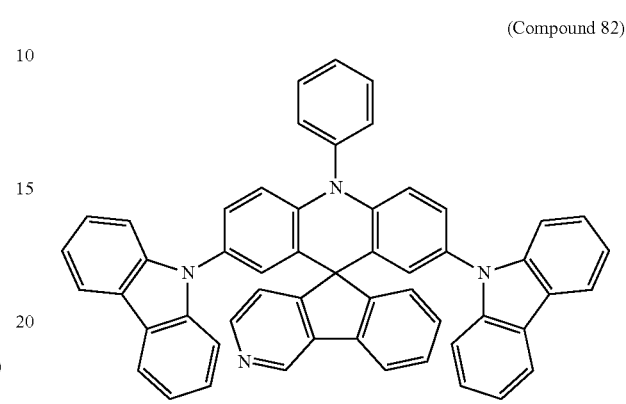
[Chemical Formula 87]
(Compound 83)
[Chemical Formula 88]
(Compound 84)
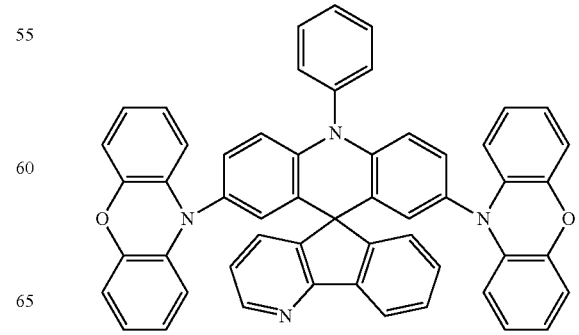

[Chemical Formula 89]
(Compound 85)
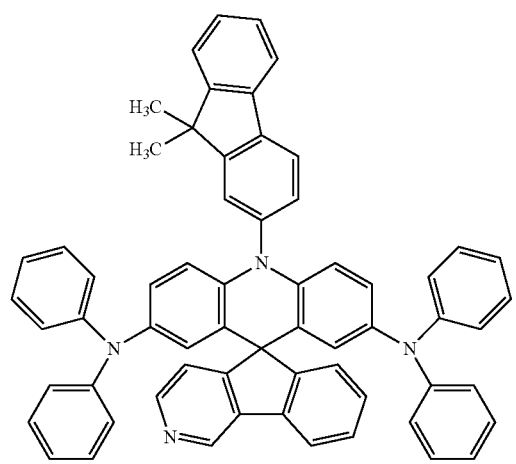
[Chemical Formula 90]
(Compound 86)
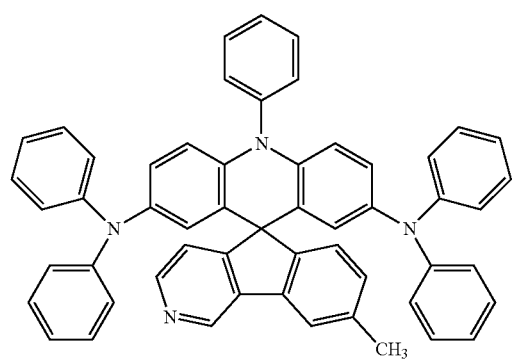
[Chemical Formula 91]
(Compound 87)
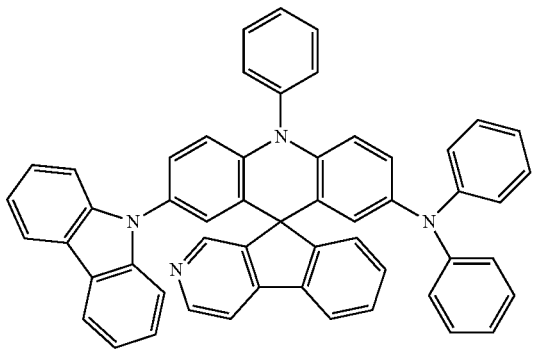
[Chemical Formula 92]
(Compound 88)
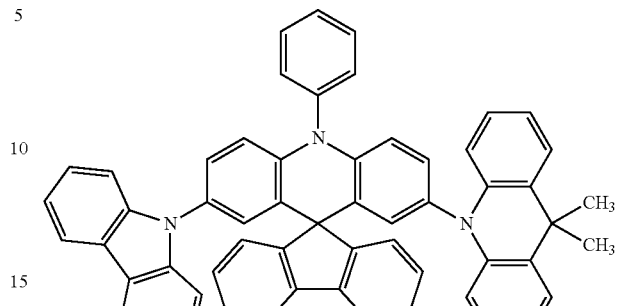
[Chemical Formula 93]
(Compound 89)
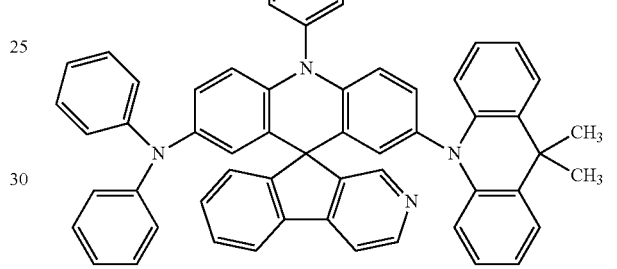
[Chemical Formula 94]
(Compound 90)
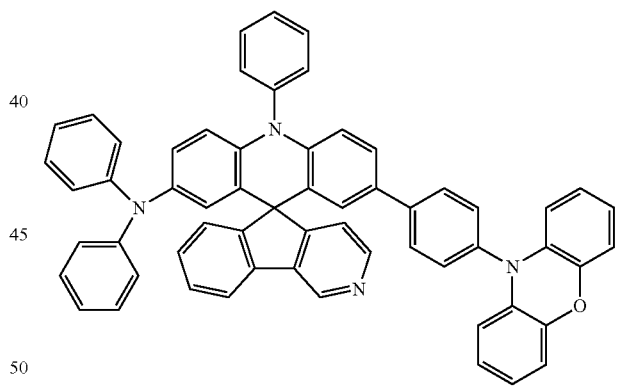
[Chemical Formula 95]
(Compound 91)
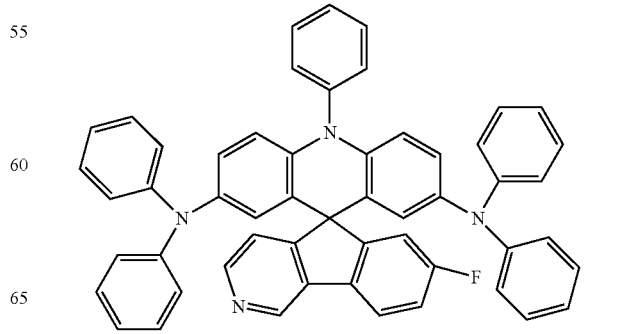

-continued

[Chemical Formula 96]

(Compound 92)

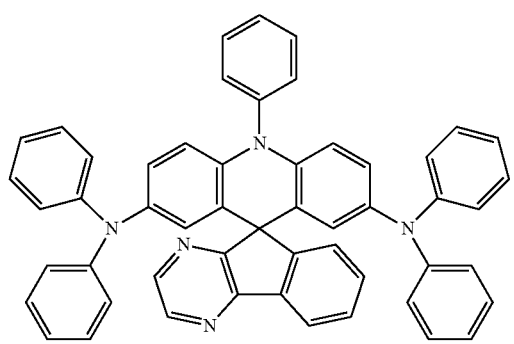

[Chemical Formula 97]

(Compound 93)

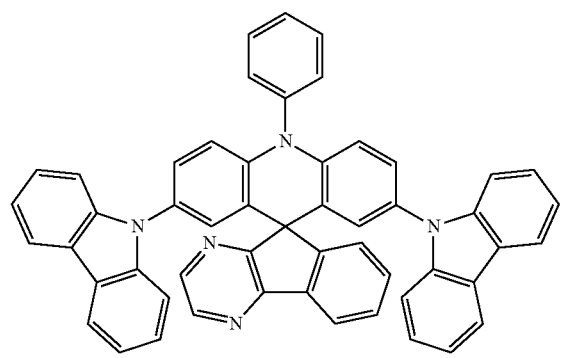

[Chemical Formula 98]

(Compound 94)

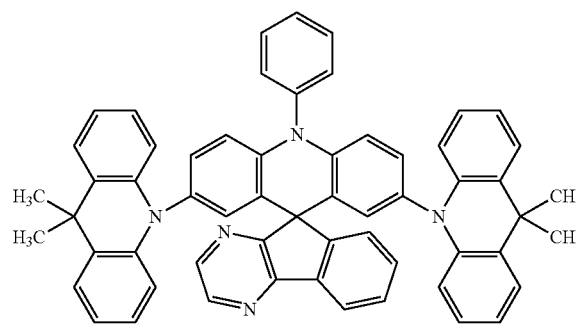

[Chemical Formula 99]

(Compound 95)

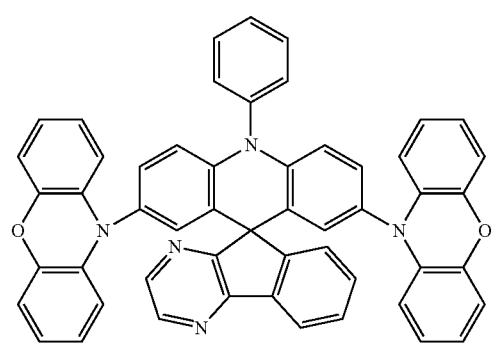

-continued

[Chemical Formula 100]

(Compound 96)

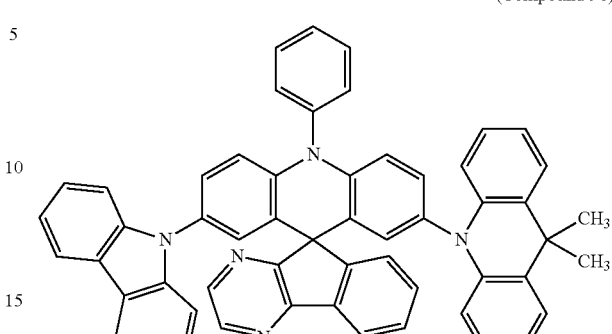

[Chemical Formula 101]

(Compound 97)

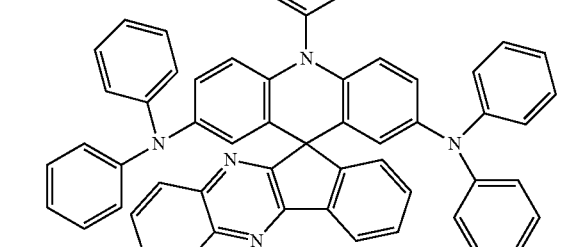

[Chemical Formula 102]

(Compound 98)

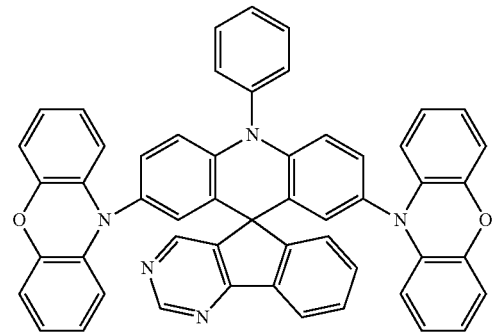

These compounds were purified by methods such as column chromatography; adsorption using, for example, a silica gel, activated carbon, or activated clay; recrystallization or crystallization using a solvent; and sublimation. The compounds were identified by an NMR analysis. A work function was measured as a material property value. The work function can be used as an index of energy level as a material for a light emitting layer.

For the measurement of work function, a 100 nm-thick thin film was fabricated on an ITO substrate, and an atmosphere photoelectron spectrometer (AC-3 produced by Riken Keiki Co., Ltd.) was used.

The organic EL device of the present invention may have a structure including an anode, a hole injection layer, a hole transport layer, an electron blocking layer, a light emitting layer, a hole blocking layer, an electron transport layer, and a cathode successively formed on a substrate, optionally with an electron injection layer between the electron transport layer and the cathode. In such a multilayer structure, some of the organic layers may be omitted. For example, the device may be configured to include an anode, a hole transport layer, a light emitting layer, an electron transport layer, an electron injection layer, and a cathode successively formed on a substrate, or to include an anode, a hole transport layer, a light emitting layer, an electron transport layer, and a cathode successively formed on a substrate.

Each of the light emitting layer, the hole transport layer, and the electron transport layer may have a laminate structure of two or more layers.

Electrode materials with high work functions such as ITO and gold are used as the anode of the organic EL device of the present invention. Examples of the material used for the hole injection layer of the organic EL device of the present invention can be naphthalenediamine derivatives; starburst-type triphenylamine derivatives; triphenylamine trimers and tetramers such as an arylamine compound having a structure in which three or more triphenylamine structures are joined within the molecule via a single bond or a divalent group that does not contain a heteroatom; accepting heterocyclic compounds such as hexacyano azatriphenylene; and coating-type polymer materials, in addition to porphyrin compounds as represented by copper phthalocyanine. These materials may be formed into a thin film by a vapor deposition method, or other known methods such as a spin coating method and an inkjet method.

Examples of the material used for the hole transport layer of the organic EL device of the present invention can be compounds containing a m-carbazolylphenyl group; benzidine derivatives such as N,N'-diphenyl-N,N'-di(m-tolyl)-benzidine (TPD), N,N'-diphenyl-N,N'-di($\alpha$-naphthyl)-benzidine (NPD), and N,N,N',N'-tetrabiphenylylbenzidine; 1,1-bis[(di-4-tolylamino)phenyl]cyclohexane (TAPC); various triphenylamine trimers and tetramers; and carbazole derivatives, in addition to the spiro compounds of general formula (1) having an azafluorene ring structure of the present invention. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer. Examples of the material used for the hole injection/transport layer can be coating-type polymer materials such as poly(3,4-ethylenedioxythiophene) (PEDOT)/poly(styrene sulfonate) (PSS). These materials may be formed into a thin-film by a vapor deposition method, or other known methods such as a spin coating method and an inkjet method.

The material used for the hole injection layer or the hole transport layer may be obtained by p-doping trisbromophenylamine hexachloroantimony into a material commonly used for these layers, or may be, for example, polymer compounds each having, as a part of the compound structure, a structure of a benzidine derivative such as TPD.

Examples of the material used for the electron blocking layer of the organic EL device of the present invention can be compounds having an electron blocking effect, including carbazole derivatives such as 4,4',4''-tri(N-carbazolyl)triphenylamine (TCTA), 9,9-bis[4-(carbazol-9-yl)phenyl]fluorene, 1,3-bis(carbazol-9-yl)benzene (mCP), and 2,2-bis(4-carbazol-9-ylphenyl)adamantane (Ad-Cz); and compounds having a triphenylsilyl group and a triarylamine structure, as represented by 9-[4-(carbazol-9-yl)phenyl]-9-[4-(triphenylsilyl)phenyl]-9H-fluorene, in addition to the spiro compounds of general formula (1) having an azafluorene ring structure of the present invention. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer. These materials may be formed into a thin film by a vapor deposition method, or other known methods such as a spin coating method and an inkjet method.

Examples of the material used for the light emitting layer of the organic EL device of the present invention can be the spiro compounds of general formula (1) having an azafluorene ring structure of the present invention; delayed fluorescence-emitting materials such as CDCB derivatives of PIC-TRZ (refer to Non-Patent Document 1, for example), CC2TA (refer to Non-Patent Document 3, for example), PXZ-TRZ (refer to Non-Patent Document 4, for example), 4CzIPN or the like (refer to Non-Patent Document 5, for example); various metal complexes including, for example, quinolinol derivative metal complexes such as tris(8-hydroxyquinoline)aluminum ($Alq_3$); anthracene derivatives; bis(styryl)benzene derivatives; pyrene derivatives; oxazole derivatives; and polyparaphenylene vinylene derivatives. Further, the light emitting layer may be made of a host material and a dopant material. In this case, examples of the host material can be the spiro compounds of general formula (1) having an azafluorene ring structure of the present invention, mCP, thiazole derivatives, benzimidazole derivatives, and polydialkyl fluorene derivatives. Examples of the dopant material can be the spiro compounds of general formula (1) having an azafluorene ring structure of the present invention, delayed fluorescence-emitting materials such as CDCB derivatives of PIC-TRZ, CC2TA, PXZ-TRZ, 4CzIPN or the like; quinacridone, coumarin, rubrene, anthracene, perylene, and derivatives thereof; benzopyran derivatives; rhodamine derivatives; and aminostyryl derivatives. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer.

Further, the light-emitting material may be phosphorescent light-emitting material. Phosphorescent materials as metal complexes of metals such as iridium and platinum may be used as the phosphorescent light-emitting material. Examples of the phosphorescent materials include green phosphorescent materials such as $Ir(ppy)_3$, blue phosphorescent materials such as Flrpic and FIr6, and red phosphorescent materials such as $Btp_2Ir(acac)$ and $Ir(piq)_3$. Here, carbazole derivatives such as 4,4'-di(N-carbazolyl)biphenyl (CBP), TCTA, and mCP may be used as the hole injecting and transporting host material. Compounds such as p-bis(triphenylsilyl)benzene (UGH2), and 2,2',2''-(1,3,5-phenylene)-tris(1-phenyl-1H-benzimidazole) (TPBI) may be used as the electron transporting host material. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer.

In order to avoid concentration quenching, the doping of the host material with the phosphorescent light-emitting material should preferably be made by co-evaporation in a range of 1 to 30 weight percent with respect to the whole light emitting layer.

These materials may be formed into a thin-film by using a vapor deposition method, or other known methods such as a spin coating method and an inkjet method.

It is also possible to produce a device of a structure that includes a light emitting layer produced with the compound of the present invention, and an adjacently laminated light emitting layer produced by using a compound of a different work function as the host material (refer to Non-Patent Document 6, for example).

The hole blocking layer of the organic EL device of the present invention may be formed by using hole blocking compounds such as various rare earth complexes, oxazole derivatives, triazole derivatives, and triazine derivatives, in addition to the metal complexes of phenanthroline derivatives such as bathocuproin (BCP), and the metal complexes of quinolinol derivatives such as aluminum(III) bis(2-methyl-8-quinolinate)-4-phenylphenolate (BAlq). These materials may also serve as the material of the electron transport layer. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer. These materials may be formed into a thin-film by using vapor deposition method, or other known methods such as a spin coating method and an inkjet method.

The electron transport layer of the organic EL device of the present invention may be formed by using various metal complexes, triazole derivatives, triazine derivatives, oxadiazole derivatives, thiadiazole derivatives, carbodiimide derivatives, quinoxaline derivatives, phenanthroline derivatives, silole derivatives, and benzimidazole derivatives such as TPBI, in addition to metal complexes of quinolinol derivatives such as Alq$_a$ and BAlq. These may be individually deposited for film forming, may be used as a single layer deposited as a mixture with other materials, or may be formed as a laminate of individually deposited layers, a laminate of mixedly deposited layers, or a laminate of an individually deposited layer and a mixedly deposited layer. These materials may be formed into a thin-film by using a vapor deposition method, or other known methods such as a spin coating method and an inkjet method.

Examples of the material used for the electron injection layer of the organic EL device of the present invention can be alkali metal salts such as lithium fluoride and cesium fluoride; alkaline earth metal salts such as magnesium fluoride; and metal oxides such as aluminum oxide. However, the electron injection layer may be omitted in the preferred selection of the electron transport layer and the cathode.

The material used for the electron injection layer or the electron transport layer may be obtained by N-doping metals such as cesium into a material commonly used for these layers.

The cathode of the organic EL device of the present invention may be made of an electrode material with a low work function such as aluminum, or an alloy of an electrode material with an even lower work function such as a magnesium-silver alloy, a magnesium-indium alloy, and an aluminum-magnesium alloy.

Specific examples of preferred materials that may be used in the organic EL device of the present invention are shown below, but the materials that may be used in the present invention are not construed as being limited to the following exemplified compounds. The compound that is shown as a material having a particular function may also be used as a material having another function. In the structural formulae of the following exemplary compounds, R and $R_2$ to $R_7$ each independently represent a hydrogen atom or a substituent, and n represents an integer of 3 to 5.

Preferred examples of a compound that may also be used as the host material of the light emitting layer are shown below.

[Chemical Formula 103]

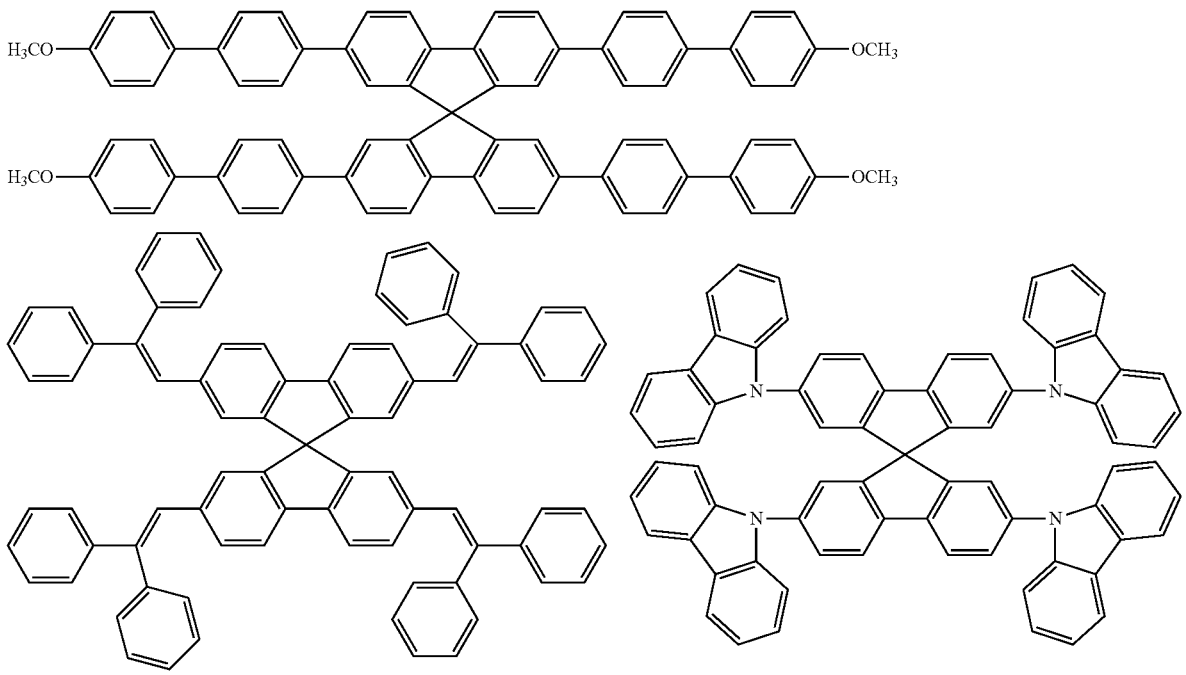

-continued
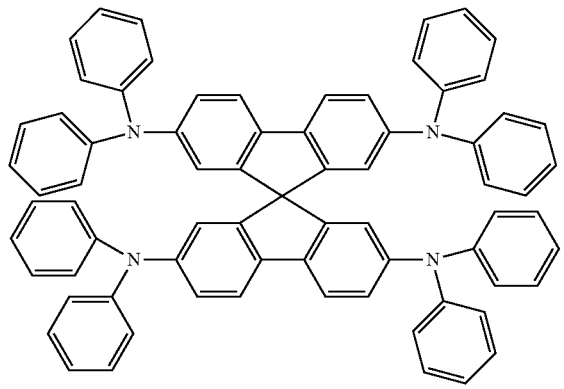
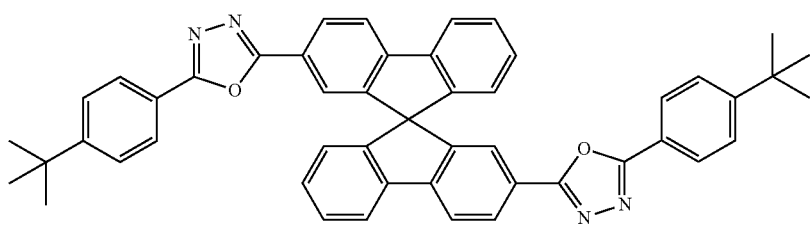
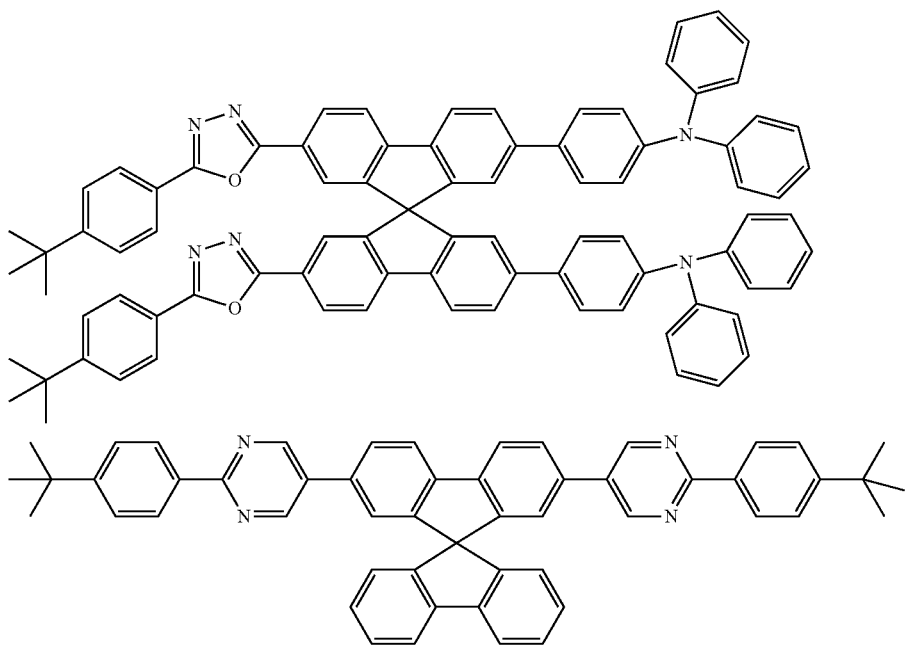
[Chemical Formula 104]
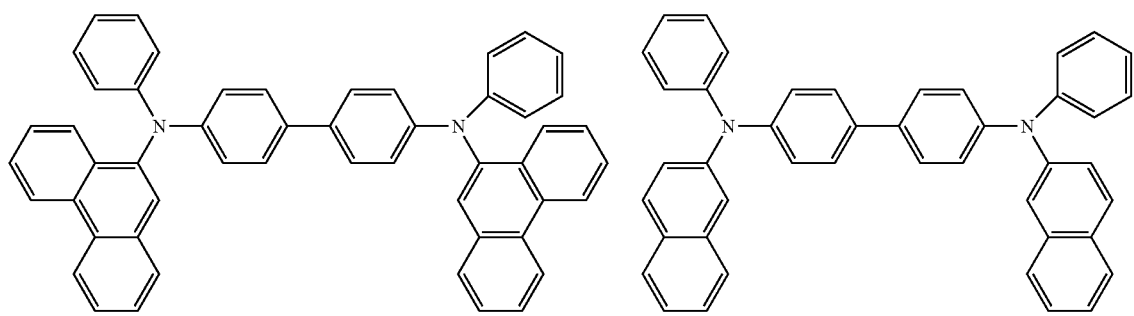

-continued
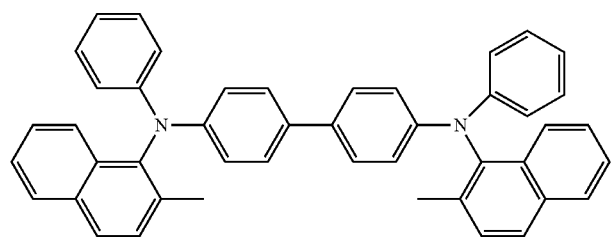
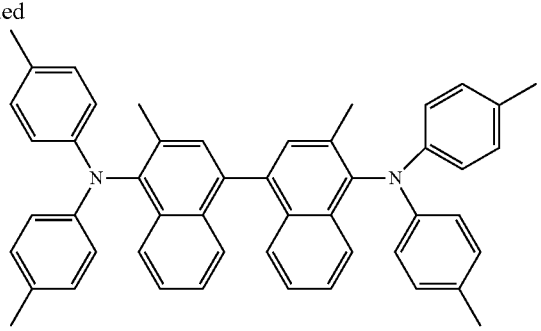
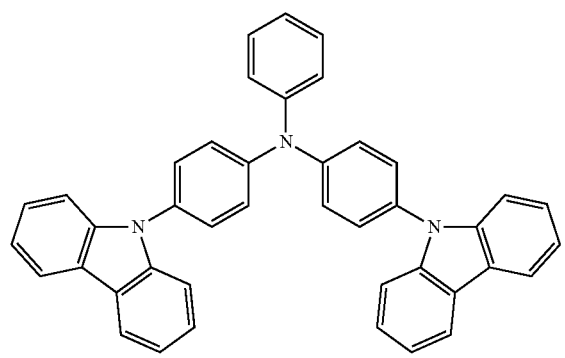
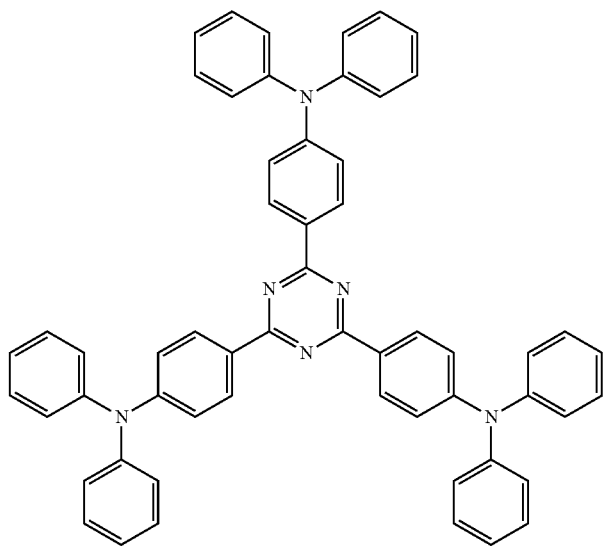
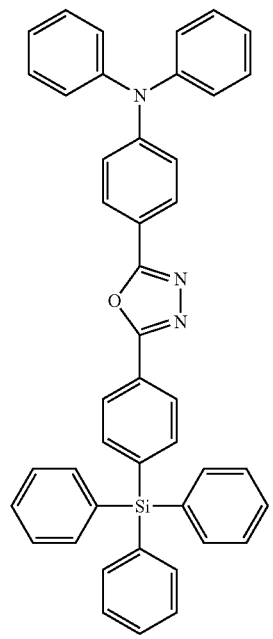
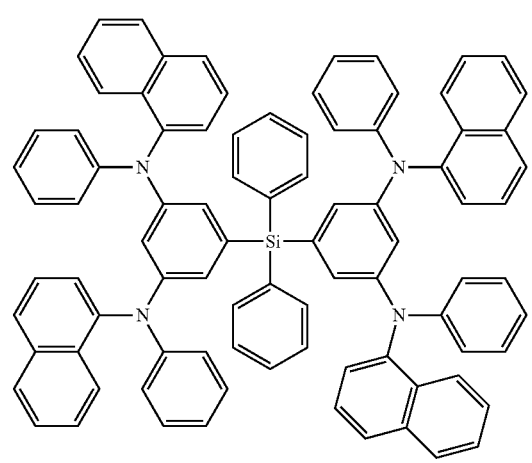
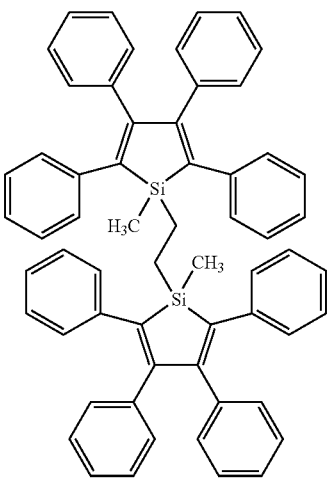

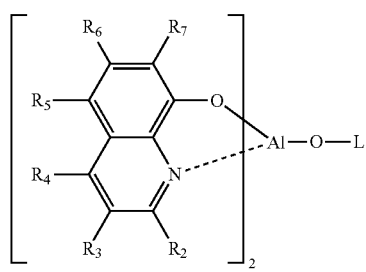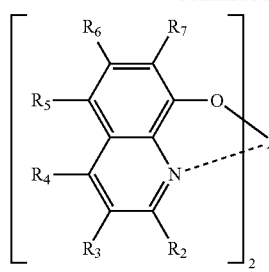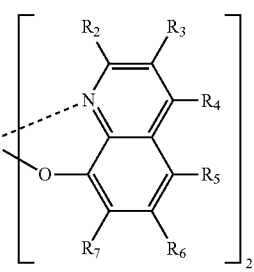
[Chemical Formula 105]
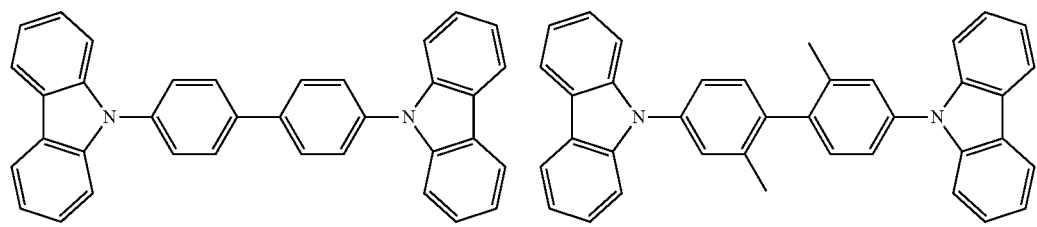
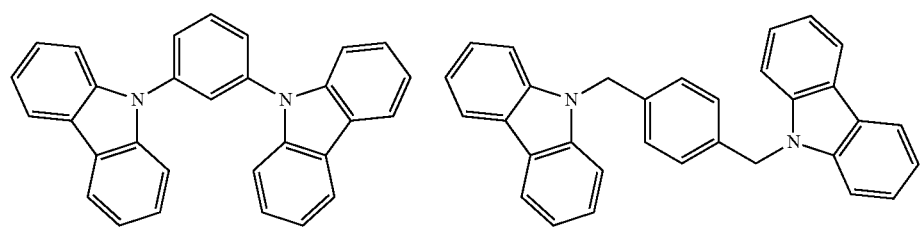
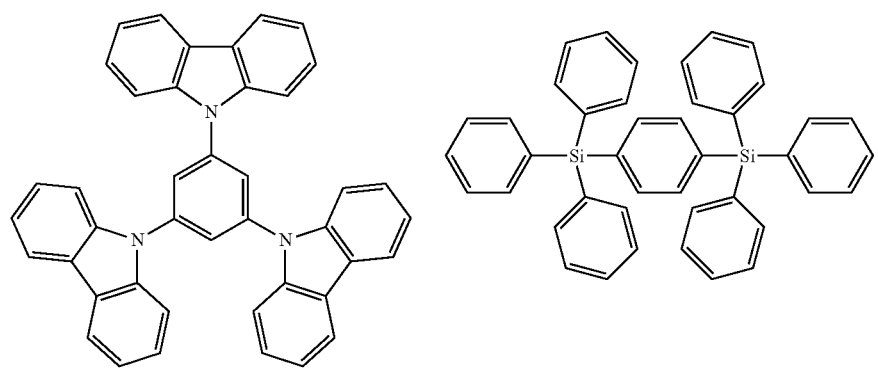
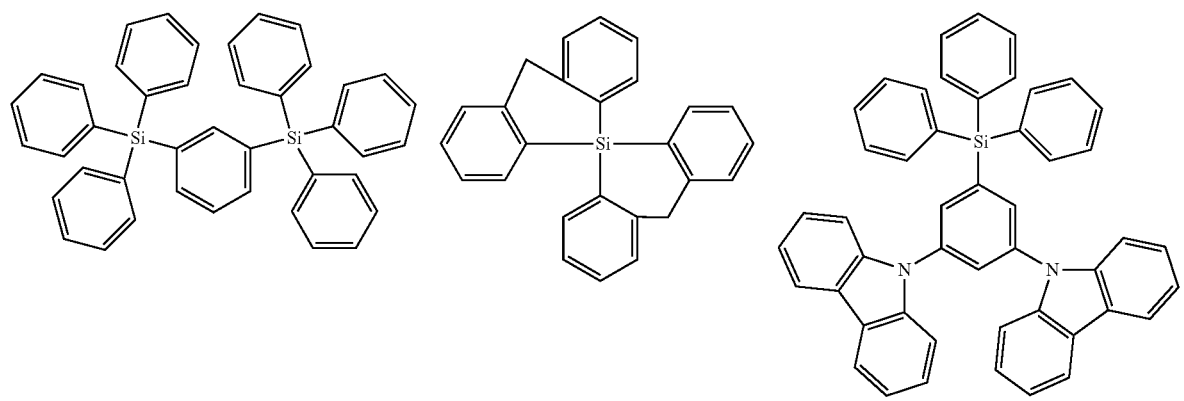

[Chemical Formula 106]
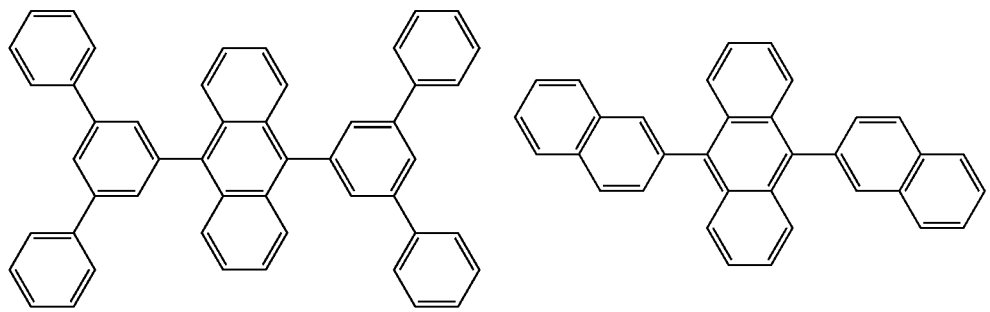

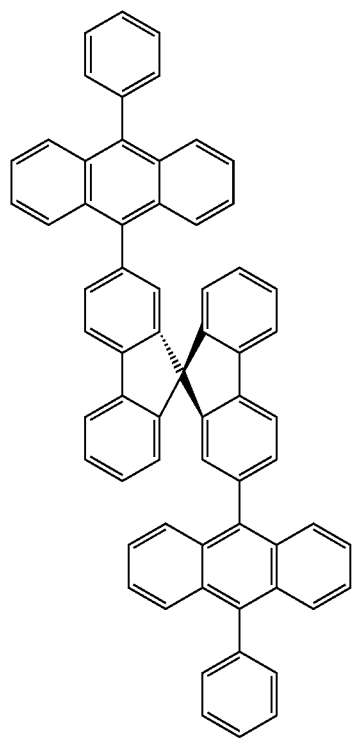
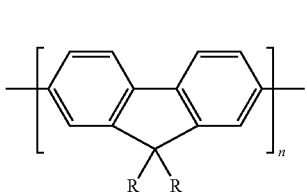
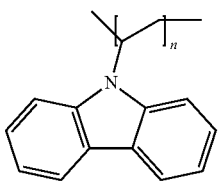
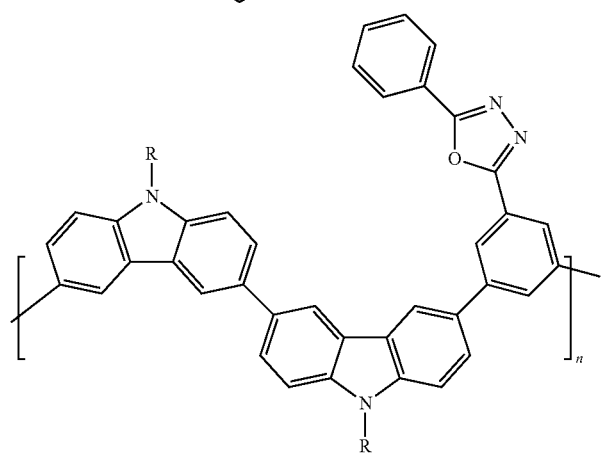
[Chemical Formula 107]
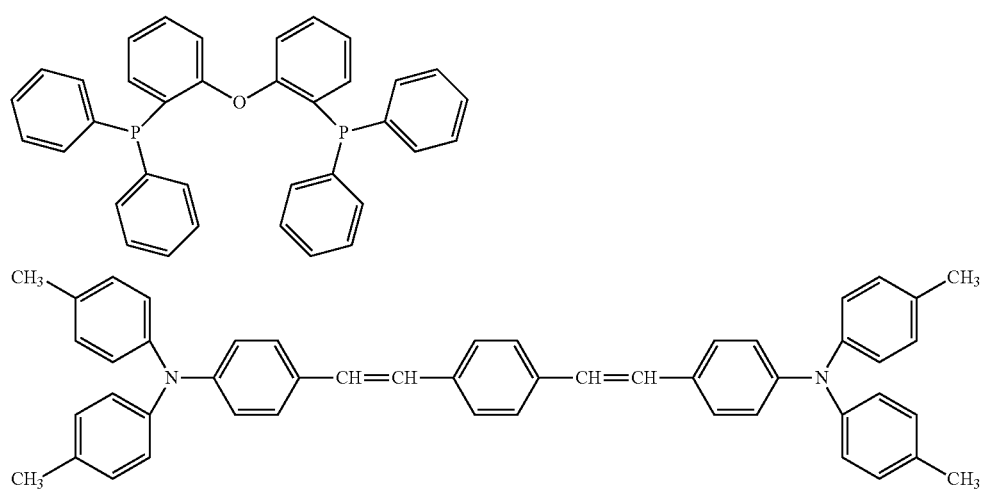

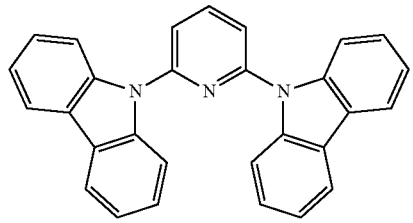 [SMILES: c1cc(-n2c3ccccc3c3ccccc32)nc(-n2c3ccccc3c3ccccc32)c1]
Preferred examples of a compound that may also be used as the material of the hole injection layer are shown below.
[Chemical Formula 108]
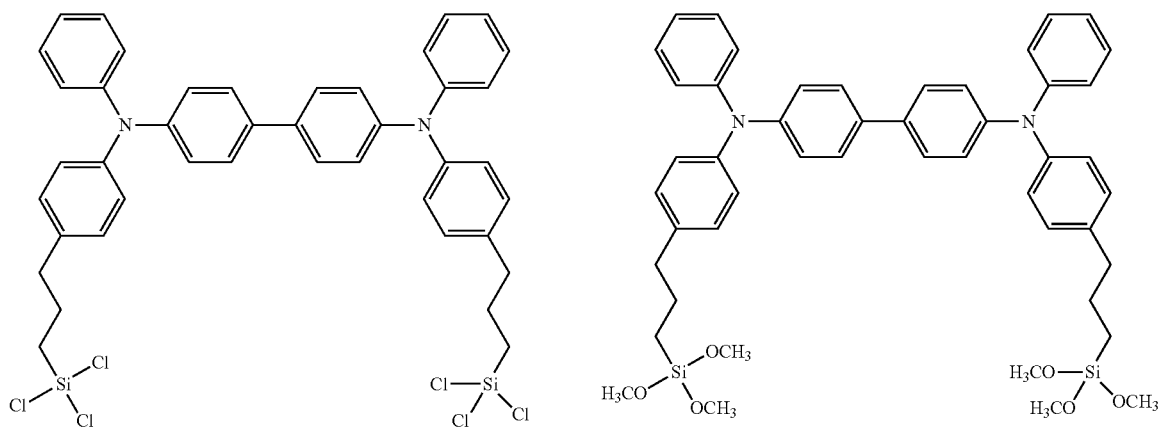
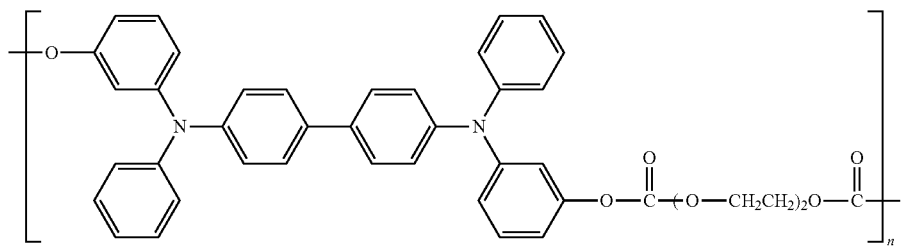
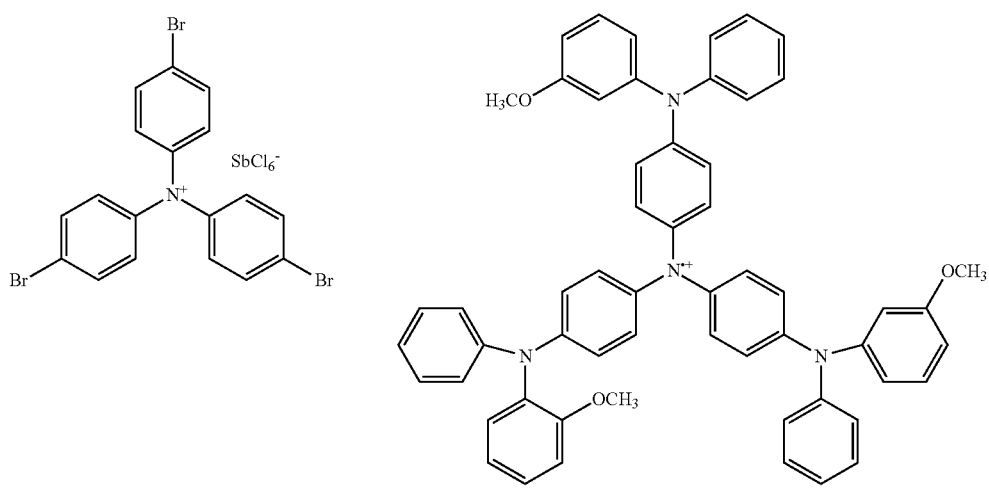

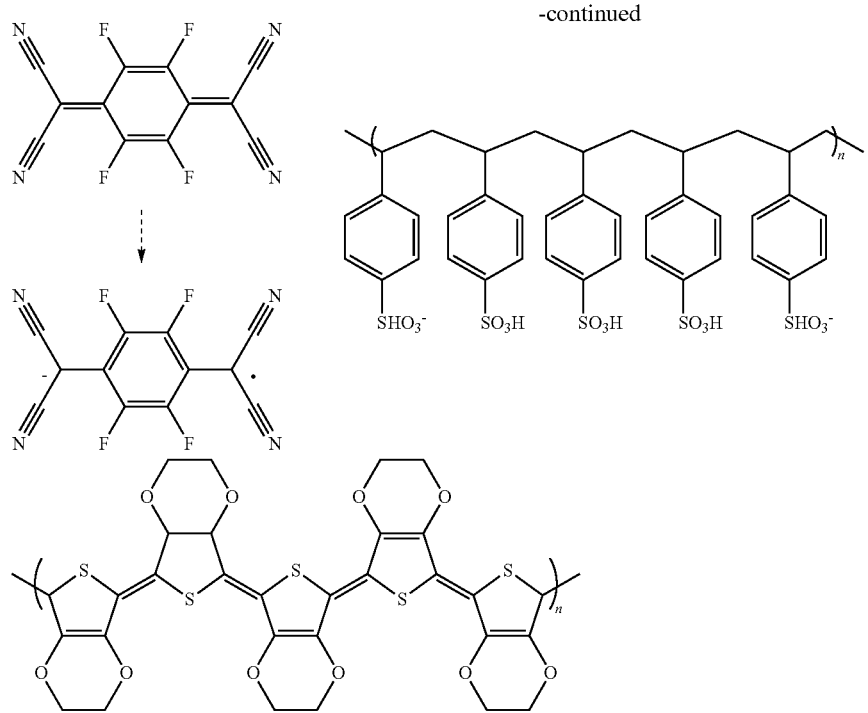
Preferred examples of a compound that may also be used as the material of the hole transport layer are shown below.
[Chemical Formula 109]
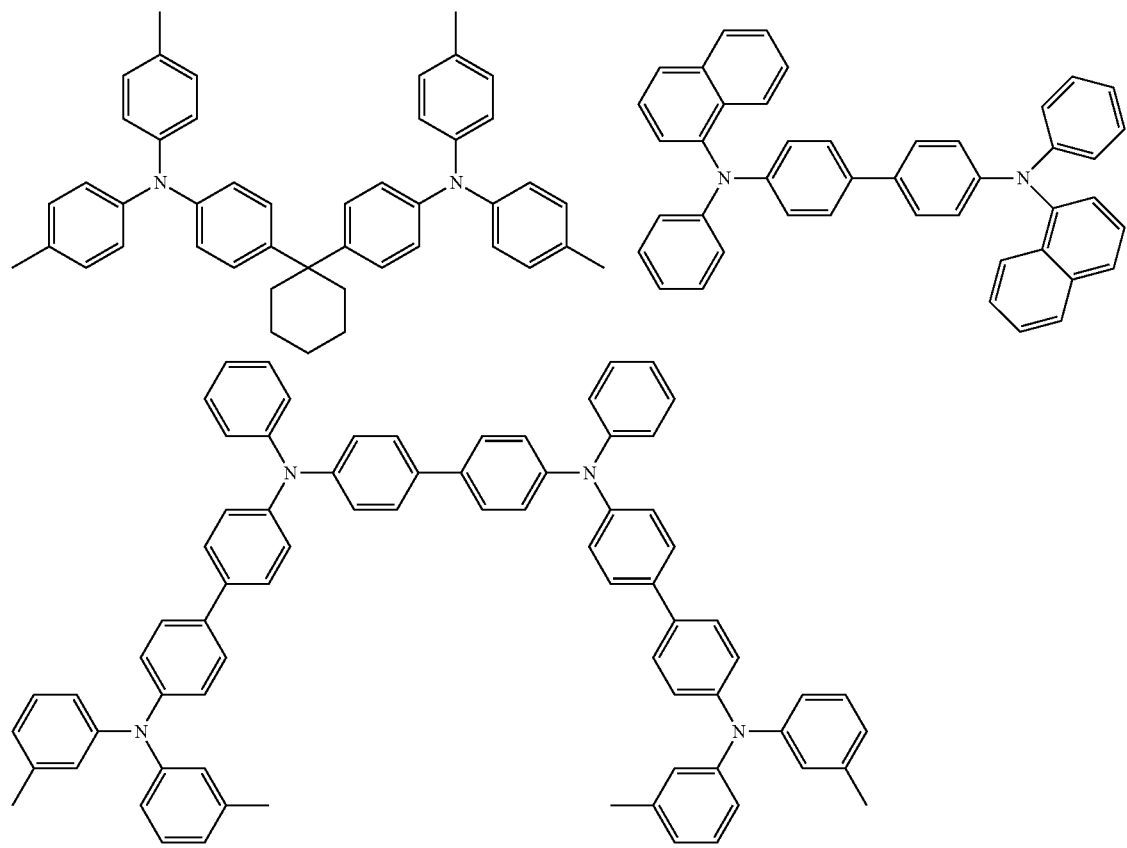

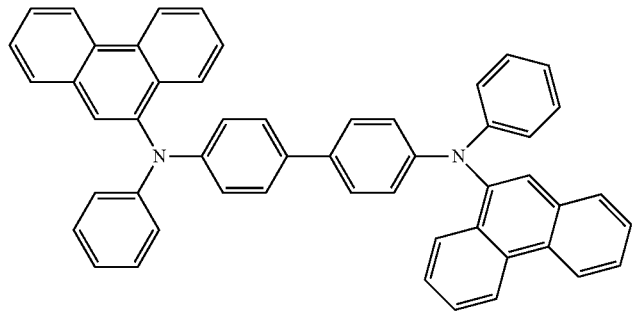
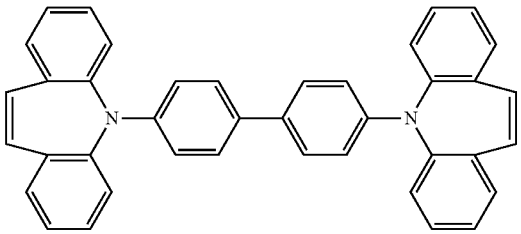
[Chemical Formula 110]
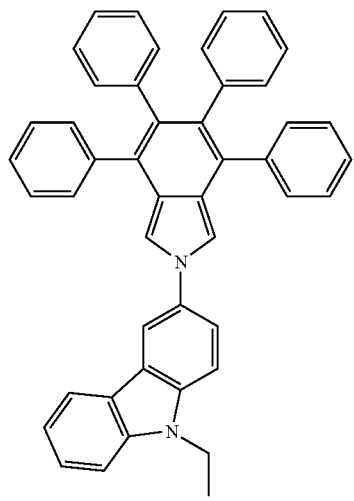
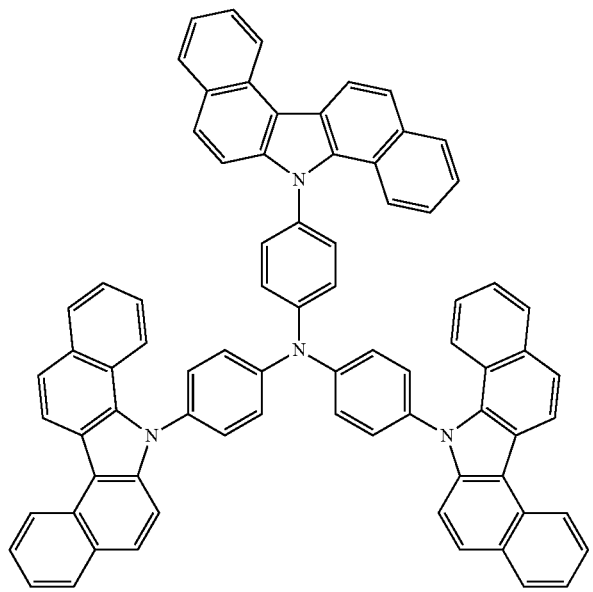
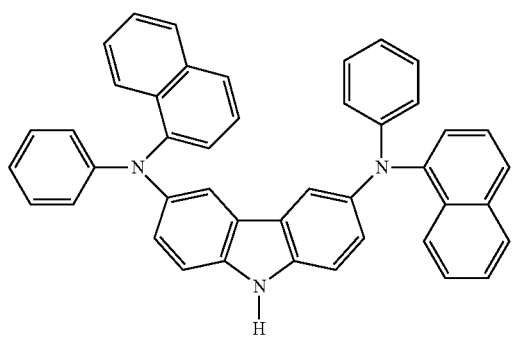

-continued
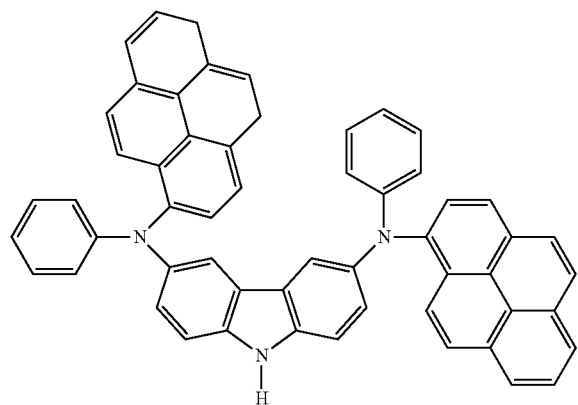
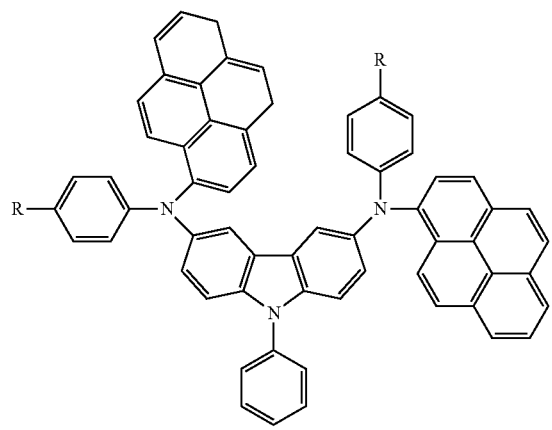
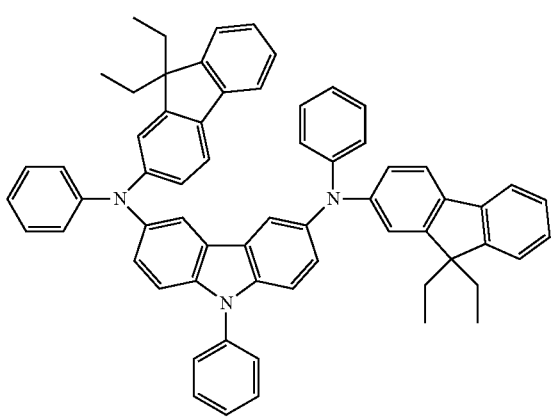
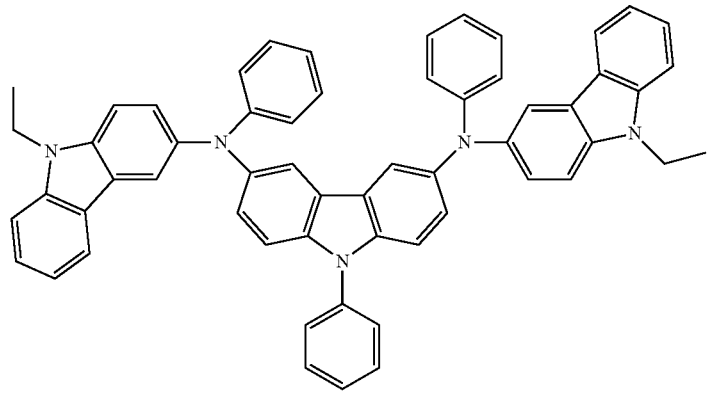
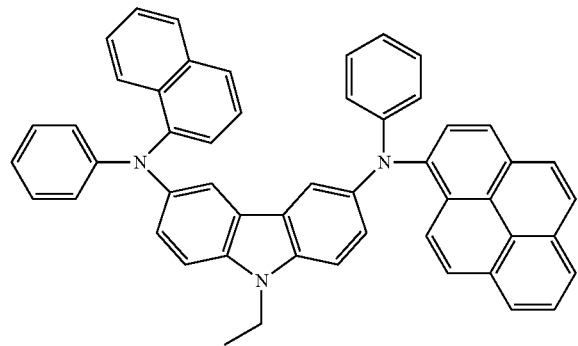

-continued
[Chemical Formula 111]
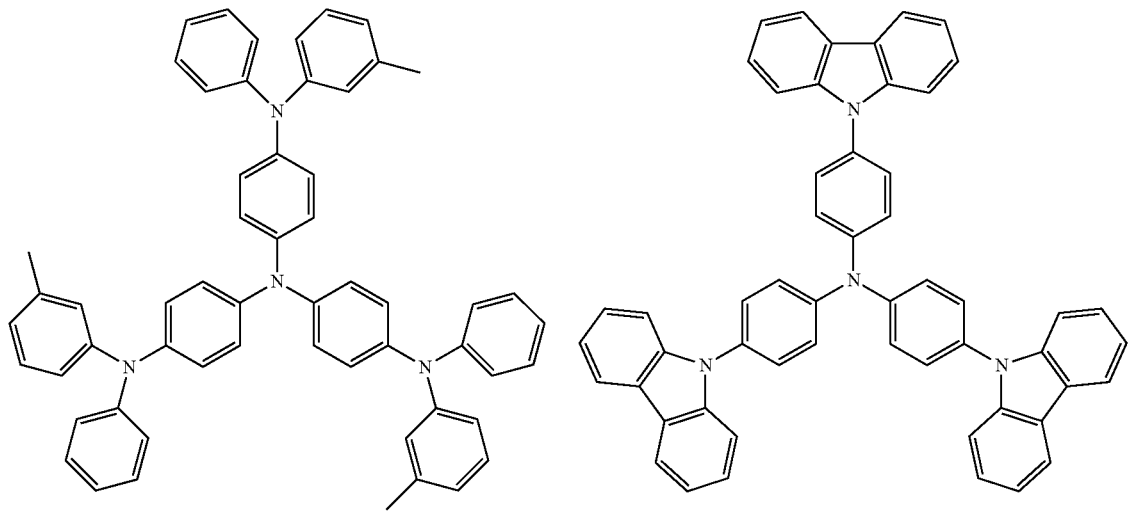
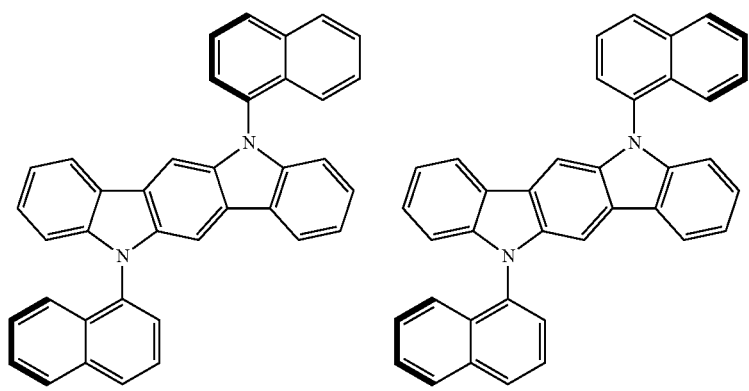
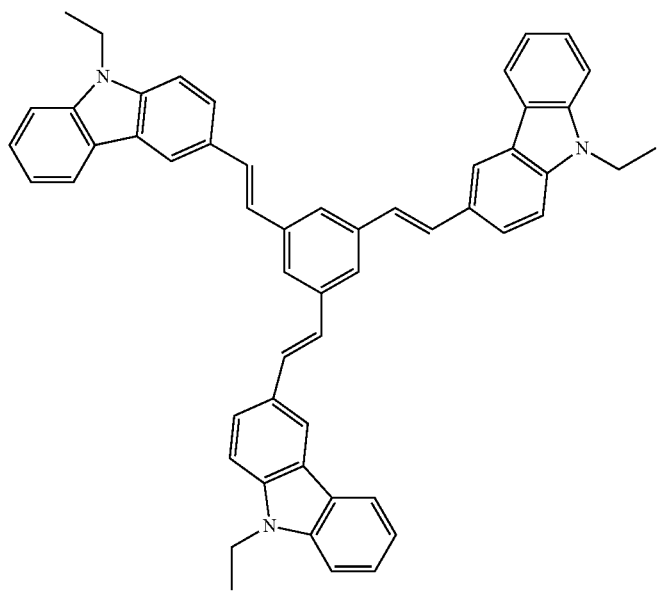

-continued
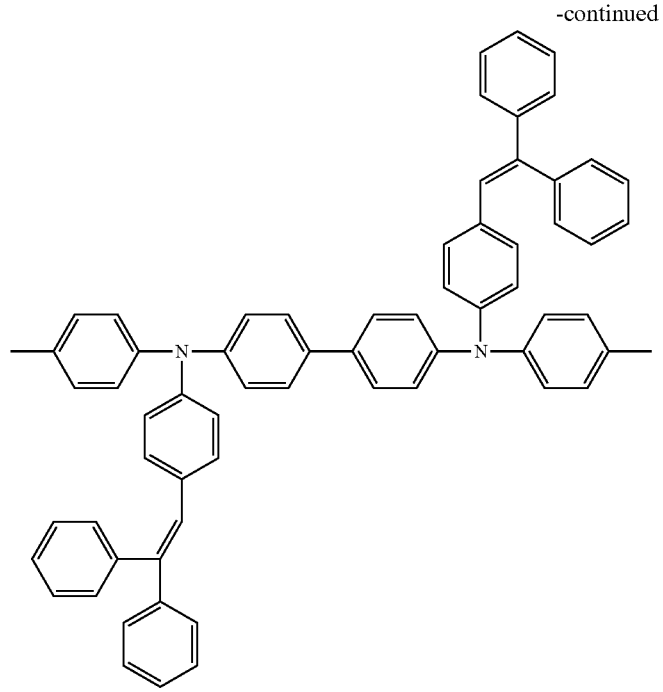
[Chemical Formula 112]
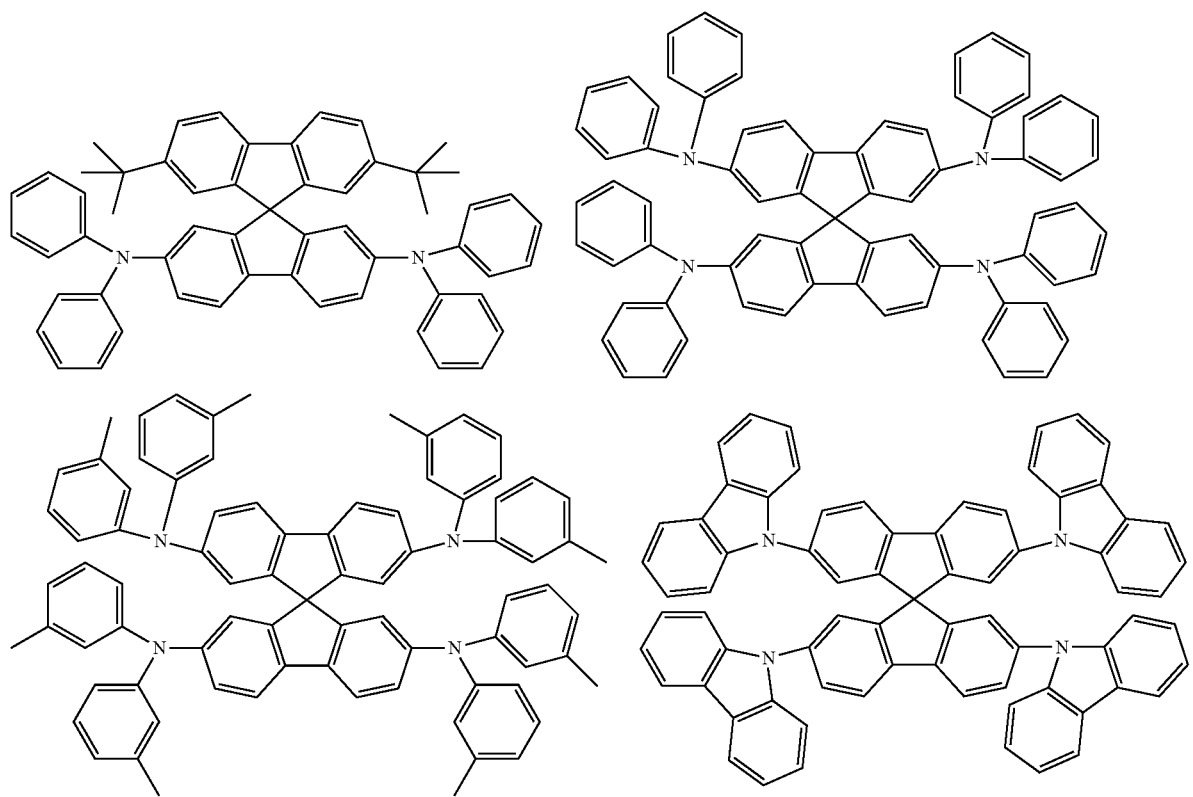
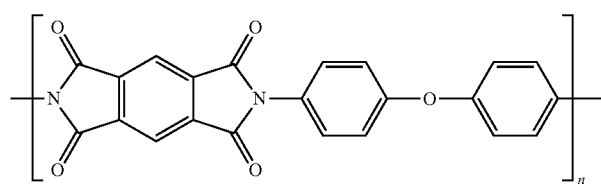

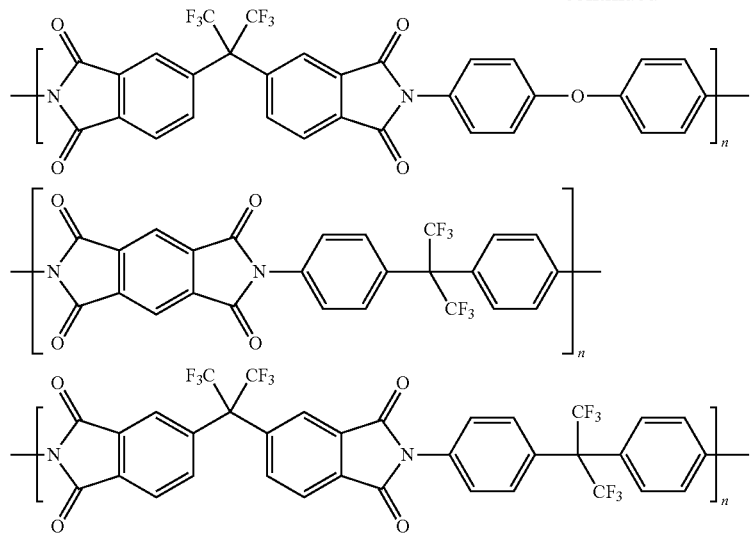
[Chemical Formula 113]
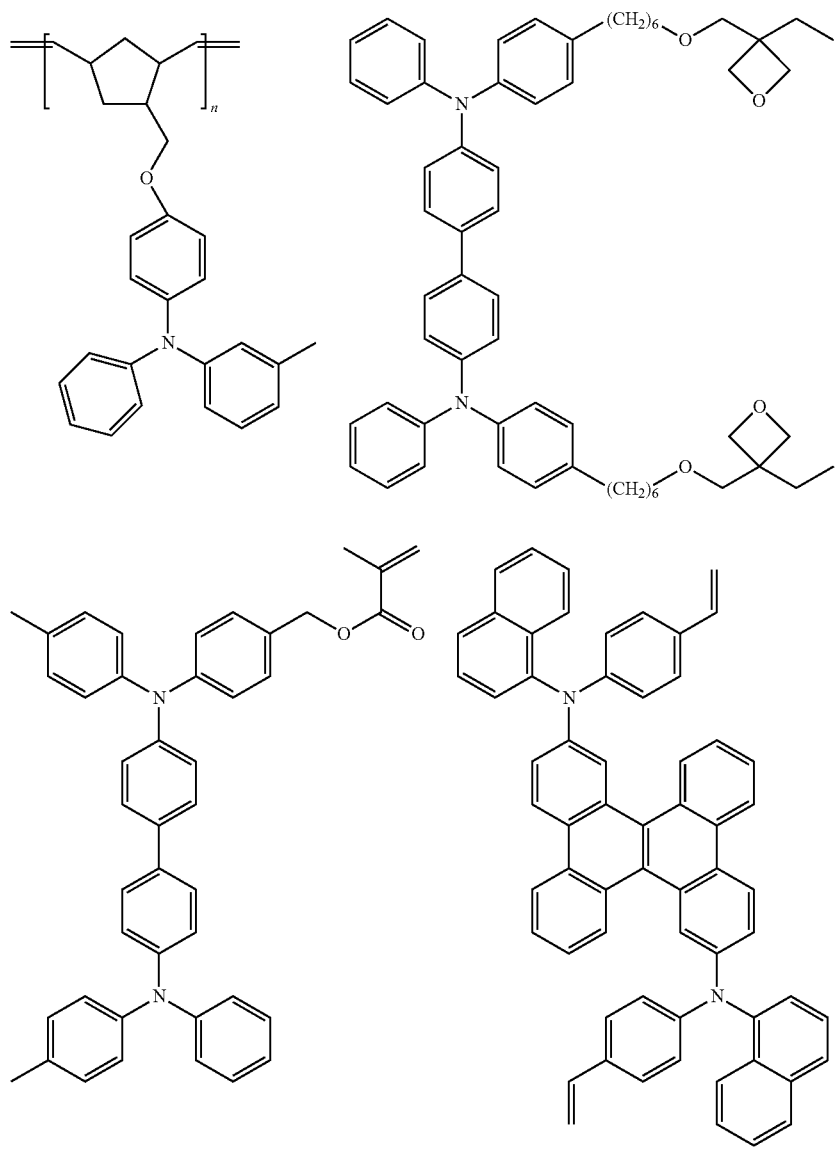

R = 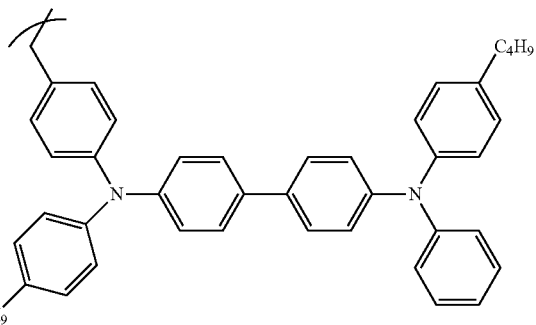
[Chemical Formula 114]
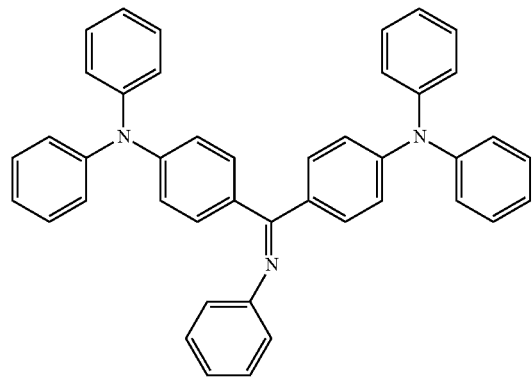
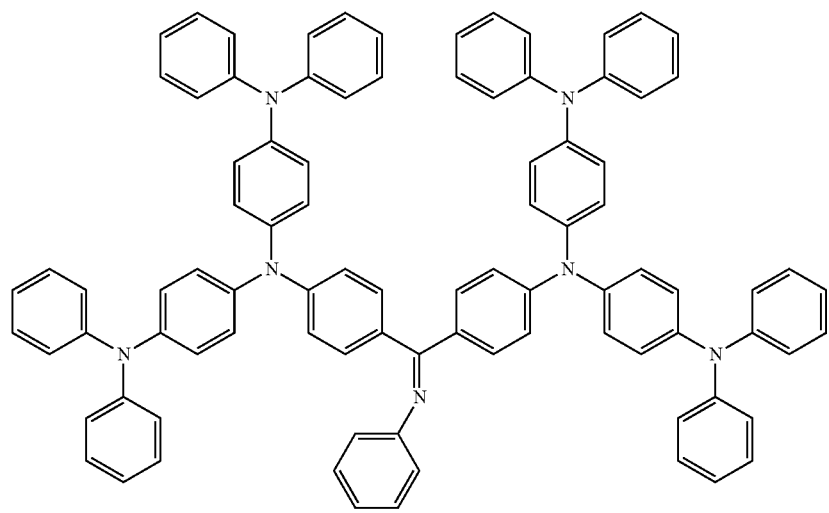

-continued
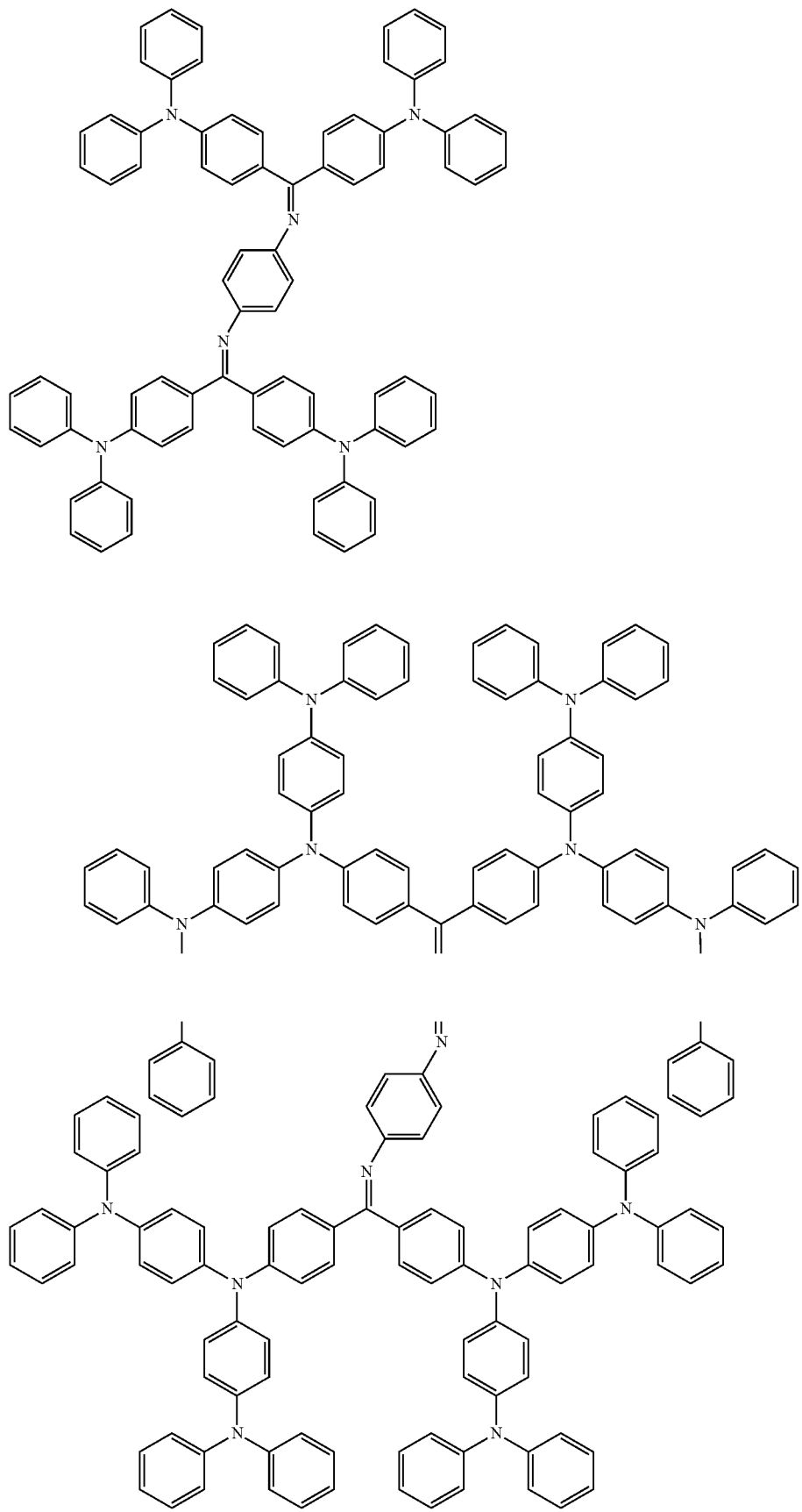

-continued
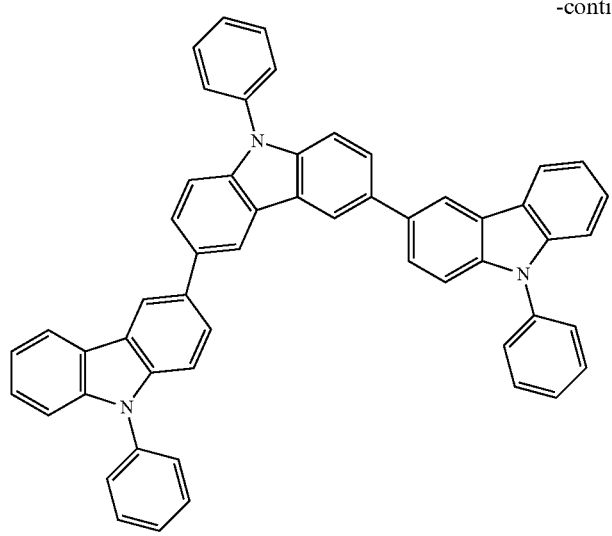
Preferred examples of a compound that may also be used as the material of the electron blocking layer are shown below.
[Chemical Formula 115]
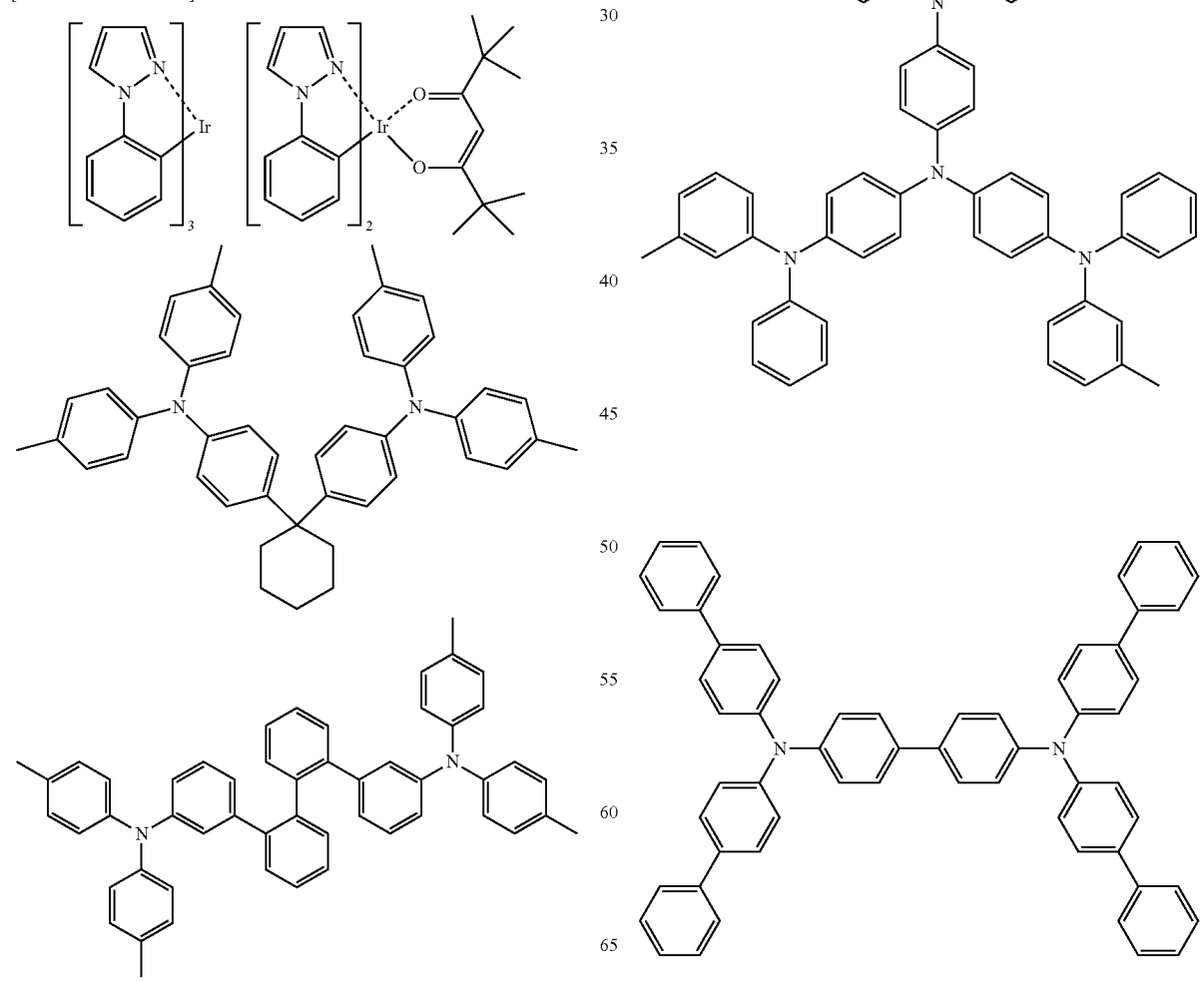

Preferred examples of a compound that may also be used as the material of the hole blocking layer are shown below.
[Chemical Formula 116]
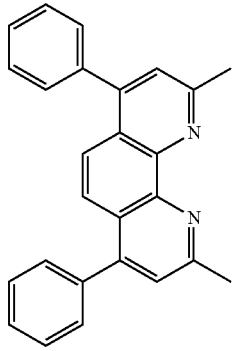
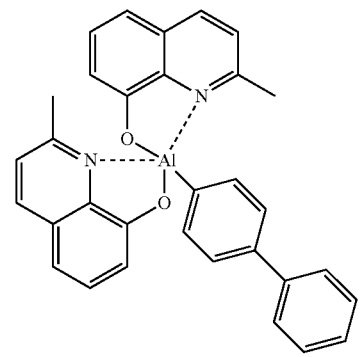
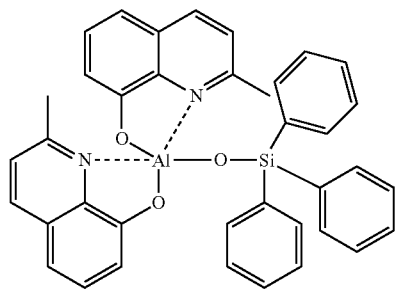
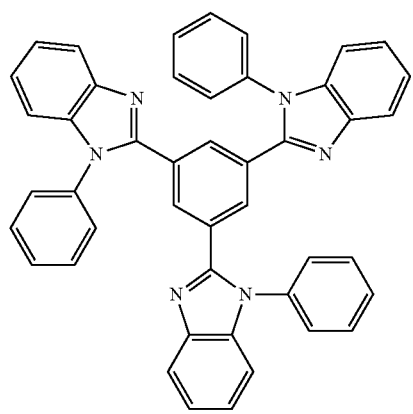
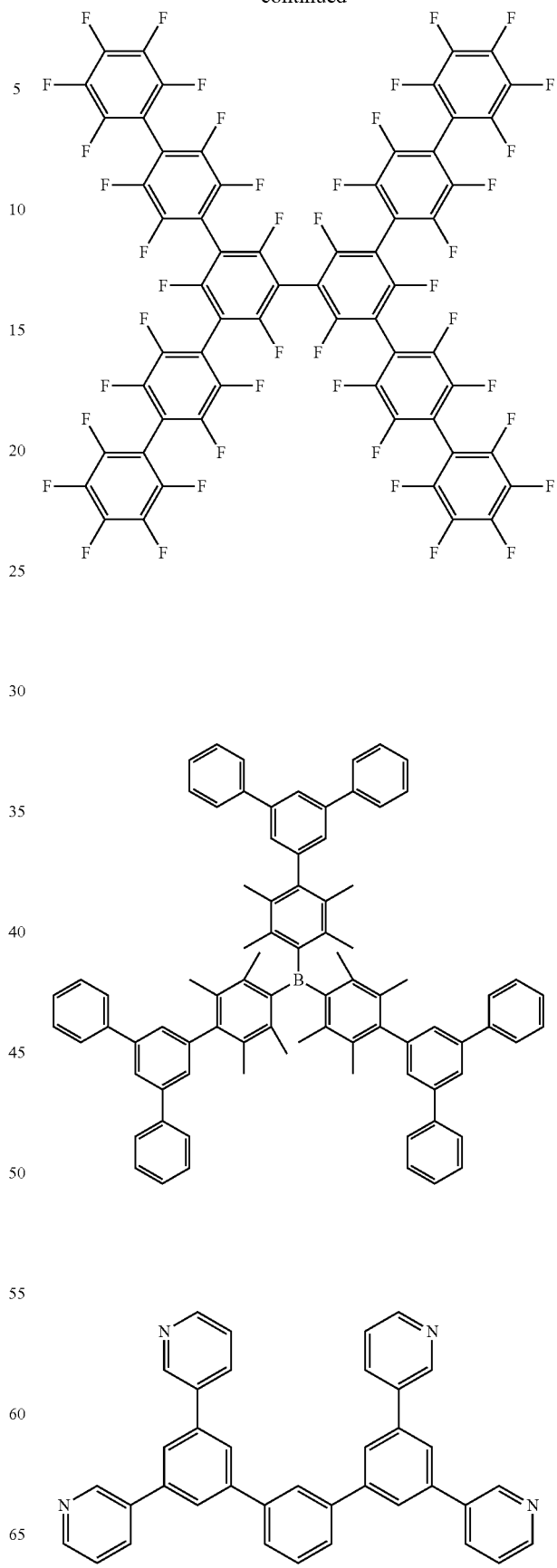

81
-continued
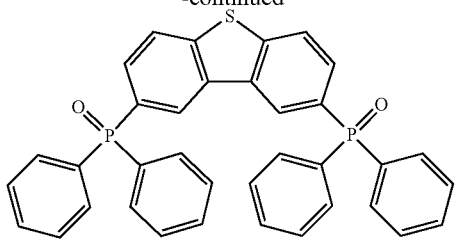
82
-continued
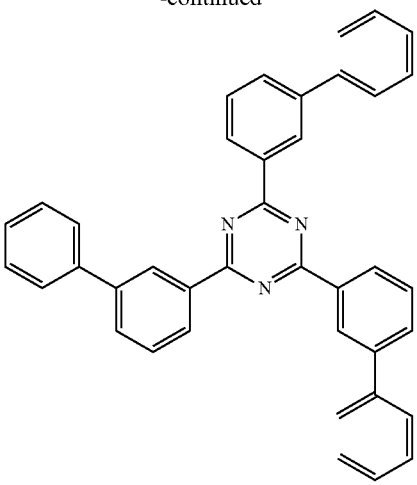
Preferred examples of a compound that may also be used as the material of the electron transport layer are shown below.
[Chemical Formula 117]
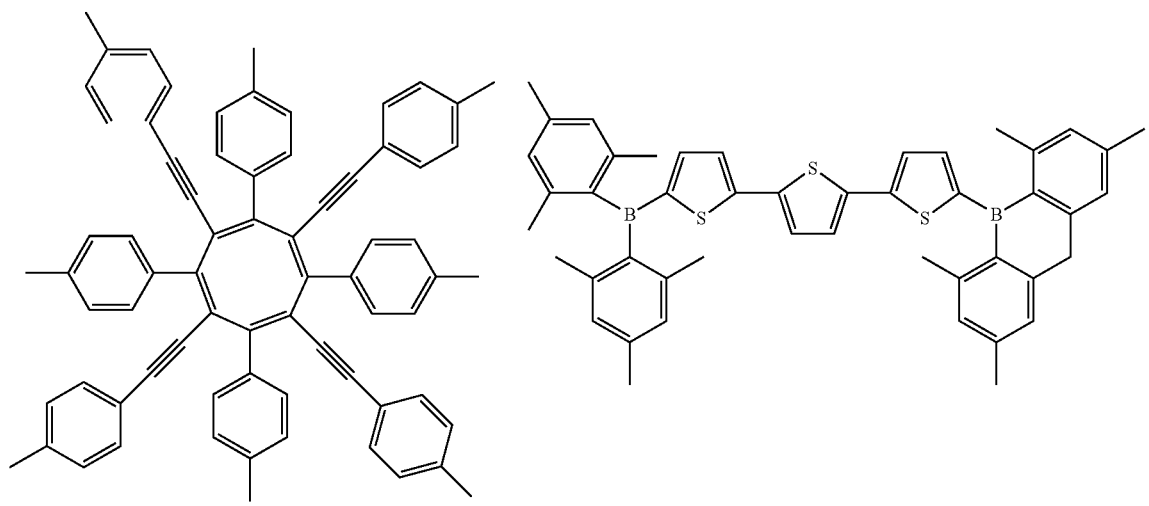
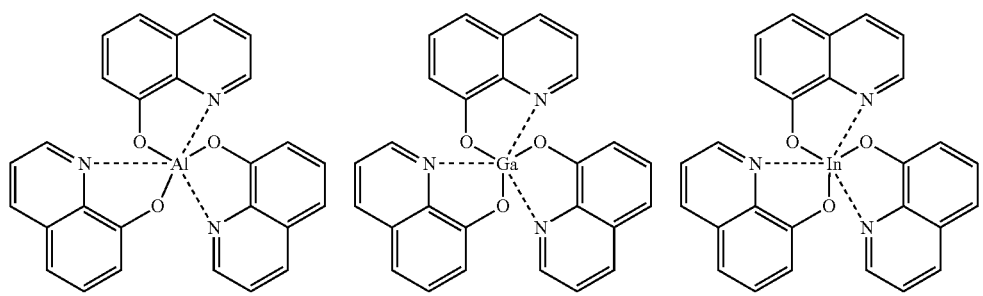

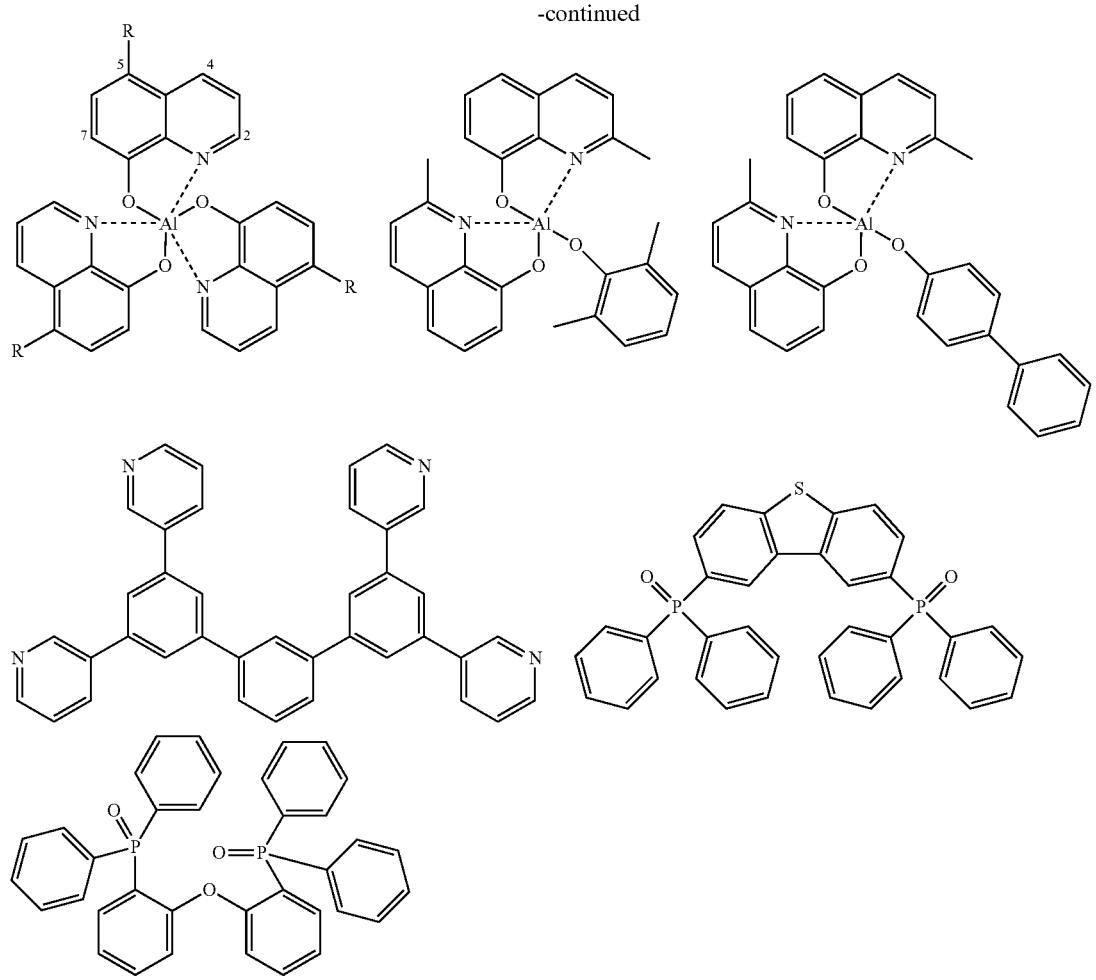
[Chemical Formula 118]
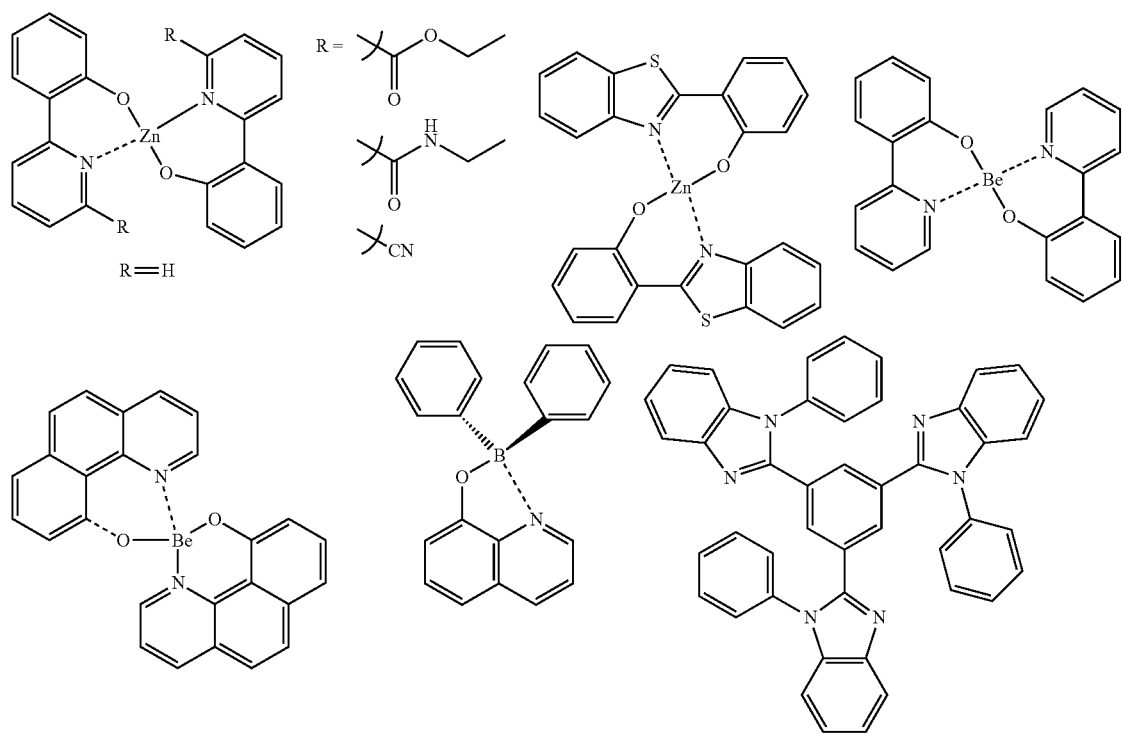

-continued
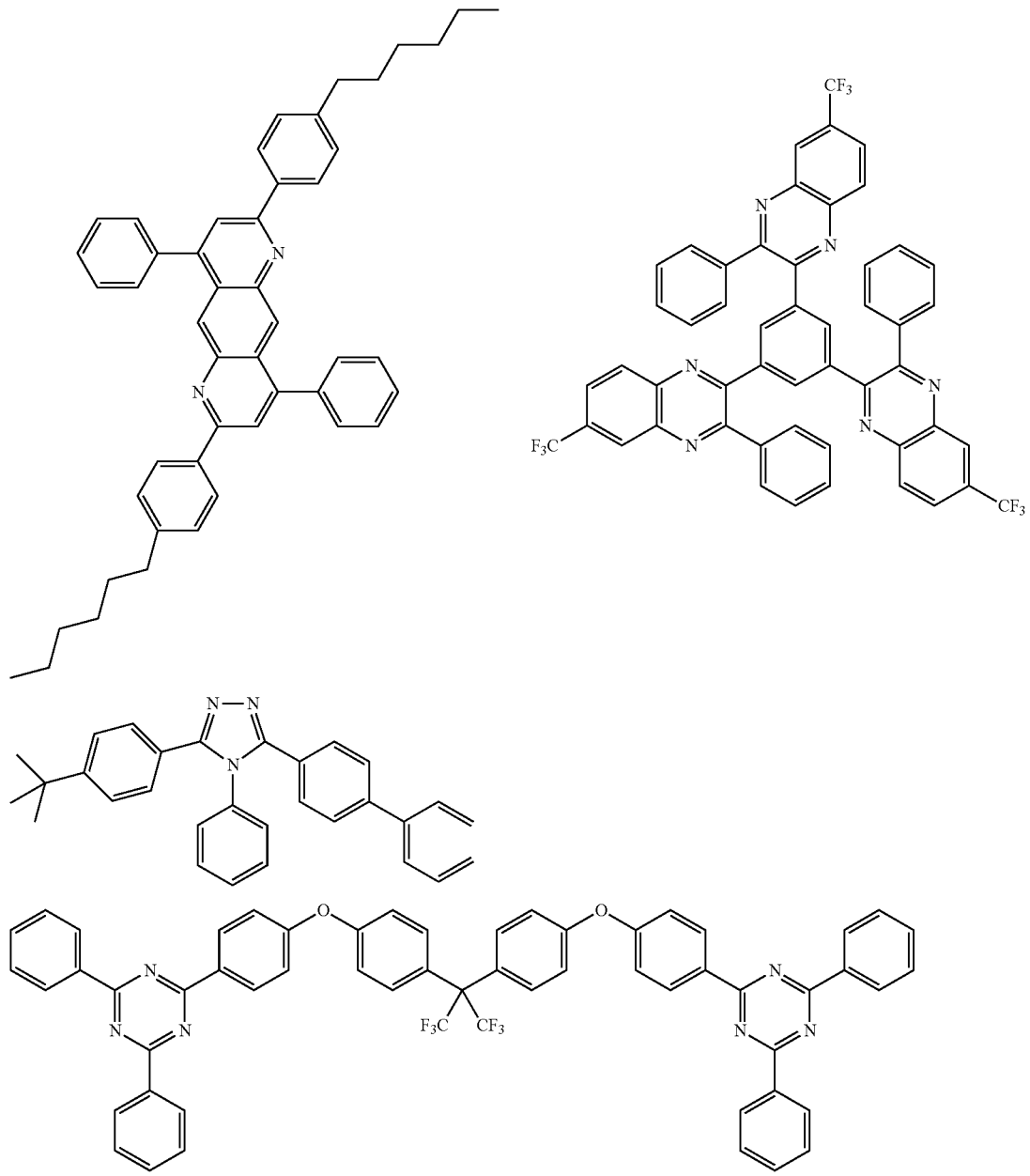
[Chemical Formula 119]
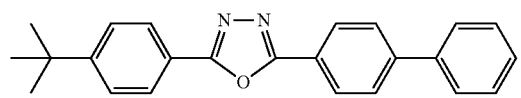
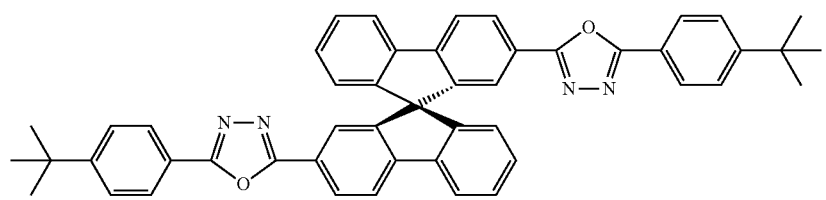

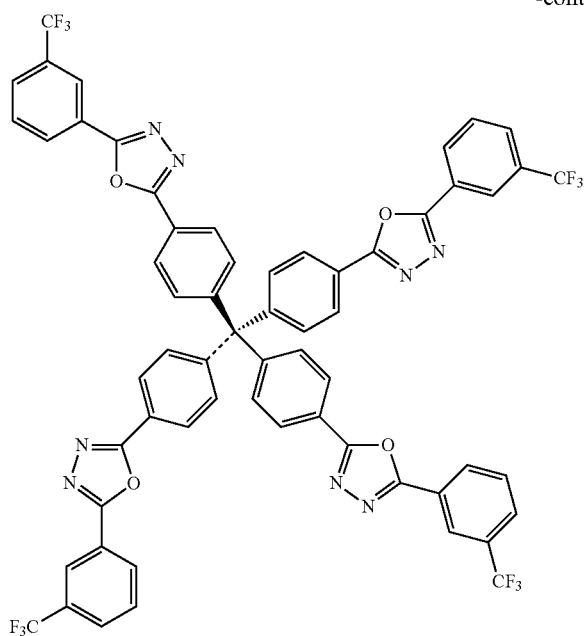
-continued
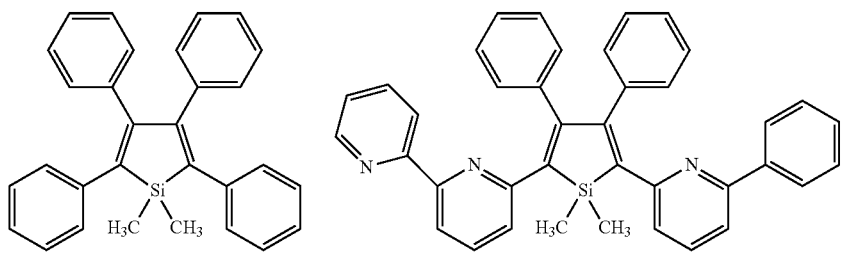
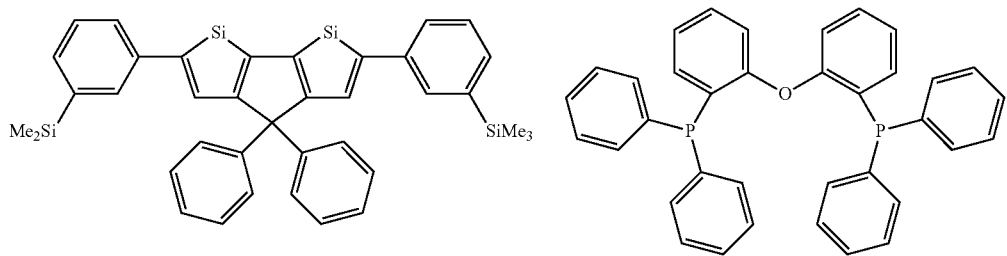
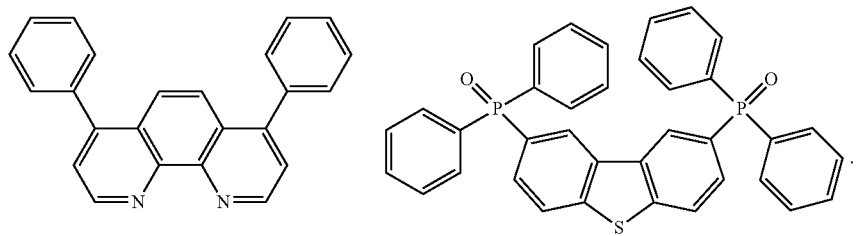 [SMILES: c1ccc(-c2ccnc3c2ccc2c(-c4ccccc4)ccnc23)cc1 ; O=P(c1ccccc1)(c1ccccc1)c1ccc2sc3ccc(P(=O)(c4ccccc4)c4ccccc4)cc3c2c1]

Preferred examples of a compound that may also be used as the material of the electron injection layer are shown below.

[Chemical Formula 120]

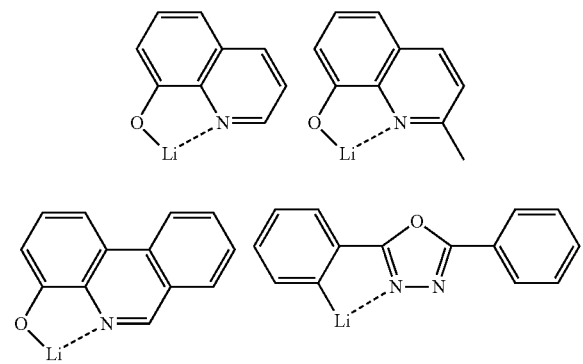

Preferred examples of a compound as a material that may be added are shown below. For example, the compound may be added as a stabilizing material.

[Chemical Formula 121]

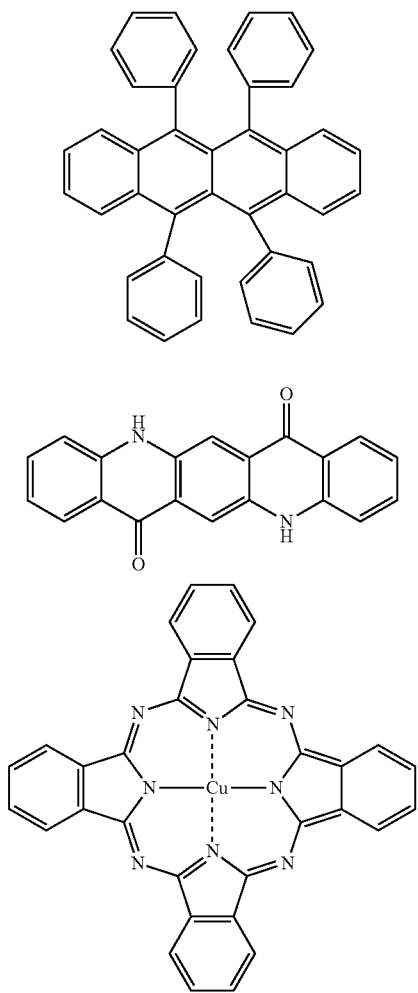

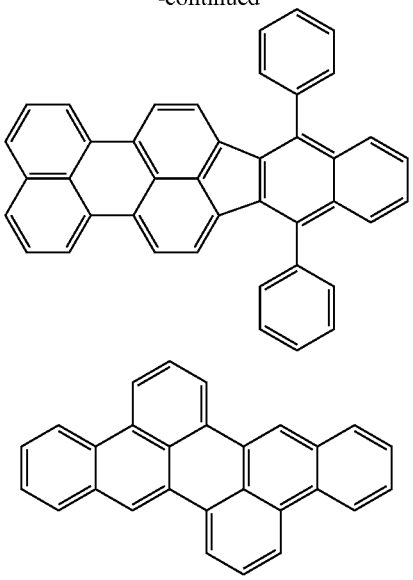

The following describes an embodiment of the present invention in more detail based on Examples. The present invention, however, is not restricted to the following Examples.

Example 1

Synthesis of 2,7-bis(Diphenylamino)-10-phenyl-10H-spiro{acridine-9,9'-(4,5-diazafluorene)} (Compound 1)

A THF solution of a 1.3 M isopropylmagnesium chloride-lithium chloride complex was added into a nitrogen-substituted reaction vessel, and cooled to −20° C. A solution containing 8.2 g of 2-iodotriphenylamine in 12 ml of THF was then dropped at −20° C., and the mixture was stirred for 30 min. Thereafter, a solution of 4,5-diazafluorenone in 70 ml of THF was dropped at −20° C., and the mixture was stirred for 2 h after raising the temperature to room temperature. After adding 100 ml of a 20% (w/v) ammonium chloride aqueous solution, the mixture was concentrated under reduced pressure, and the precipitated crude product was collected by filtration. The precipitate was then washed by being heated to reflux with methanol to obtain a white powder of 9-{2-(diphenylamino)phenyl-4,5-diazafluoren-9-ol (7.8 g; yield 83%).

7.8 g of the 9-{2-(diphenylamino)phenyl-4,5-diazafluoren-9-ol product, and 15 mL of Eaton's reagent were added into a nitrogen-substituted reaction vessel, heated, and stirred at 60° C. for 24 h. After adding 50 ml of water, a 20% (w/v) sodium hydroxide aqueous solution was added, and the precipitated crude product was collected by filtration. The precipitate was purified by column chromatography (support: NH silica gel, eluent: toluene/ethyl acetate), and through crystallization with a mixture of toluene and methanol to obtain a white powder of 10-phenyl-10H-spiro{acridine-9,9'-(4,5-diazafluorene)} (5.5 g; yield 74%).

5.0 g of the 10-phenyl-10H-spiro{acridine-9,9'-(4,5-diazafluorene)} product, and 100 mL of chloroform were added into a nitrogen-substituted reaction vessel, and 4.4 g of N-bromosuccinimide was added while stirring the mixture at room temperature. The resulting mixture was further stirred for 6 h. After adding methanol, the mixture was concentrated under reduced pressure, and washed by being heated to reflux with methanol to obtain a white powder of 2,7-dibromo-10-phenyl-10H-spiro{acridine-9,9'-(4,5-diazafluorene)} (6.5 g; yield 94%).

1.5 g of the 2,7-dibromo-10-phenyl-10H-spiro{acridine-9,9'-(4,5-diazafluorene)} product, 1.8 g of diphenylamine, 1.1 g of sodium tert-butoxide, 0.09 g of palladium acetate, 0.1 g of 2-(dicyclohexylphosphino)biphenyl, and 30 ml of o-xylene were added into a nitrogen-substituted reaction vessel, and heated to reflux for 48 h. After adding 100 ml of toluene, the mixture was heated, and stirred at 100° C. The filtrate was collected by thermal filtration, and concentrated under reduced pressure to obtain a crude product. The crude product was then purified by column chromatography (support: silica gel, eluent: toluene/ethyl acetate), and through crystallization with a mixed solvent of toluene and methanol to obtain a yellow powder of 2,7-bis(diphenylamino)-10-phenyl-10H-spiro{acridine-9,9'-(4,5-diazafluorene)} (Compound 1; 0.8 g; yield 42%).

The structure of the yellow powder product was identified by NMR. The $^1$H-NMR measurement result is shown in FIG. 1.

$^1$H-NMR (DMSO-$d_6$) detected 37 hydrogen signals, as follows. δ (ppm)=8.58 (2H), 7.92 (2H), 7.76 (2H), 7.64 (3H), 7.38 (2H), 7.08 (8H), 6.86 (4H), 6.68 (10H), 6.27 (2H), 5.92 (2H).

Example 2

Synthesis of 2,7-bis(9H-Carbazol-9-yl)-10-phenyl-10H-spiro{acridine-9,9'-(4,5-diazafluorene)} (Compound 2)

1.2 g of the 2,7-dibromo-10-phenyl-10H-spiro{acridine-9,9'-(4,5-diazafluorene)} synthesized in Example 1, 1.4 g of carbazole, 2.0 g of tripotassium phosphate, 0.4 g of copper (I) iodide, 0.1 g of 2-(dicyclohexylphosphino)biphenyl, and 24 ml of o-xylene were added into a nitrogen-substituted reaction vessel, and heated to reflux for 48 h. After adding 100 ml of toluene, the mixture was heated, and stirred at 100° C. The filtrate was collected by thermal filtration, and concentrated under reduced pressure to obtain a crude product. The crude product was purified by column chromatography (support: silica gel, eluent: toluene/ethyl acetate), and through crystallization with a mixed solvent of toluene and methanol to obtain a pale yellow powder of 2,7-bis(9H-carbazol-9-yl)-10-phenyl-10H-spiro{acridine-9,9'-(4,5-diazafluorene)} (Compound 2; 0.8 g; yield 50%).

Figure 2:
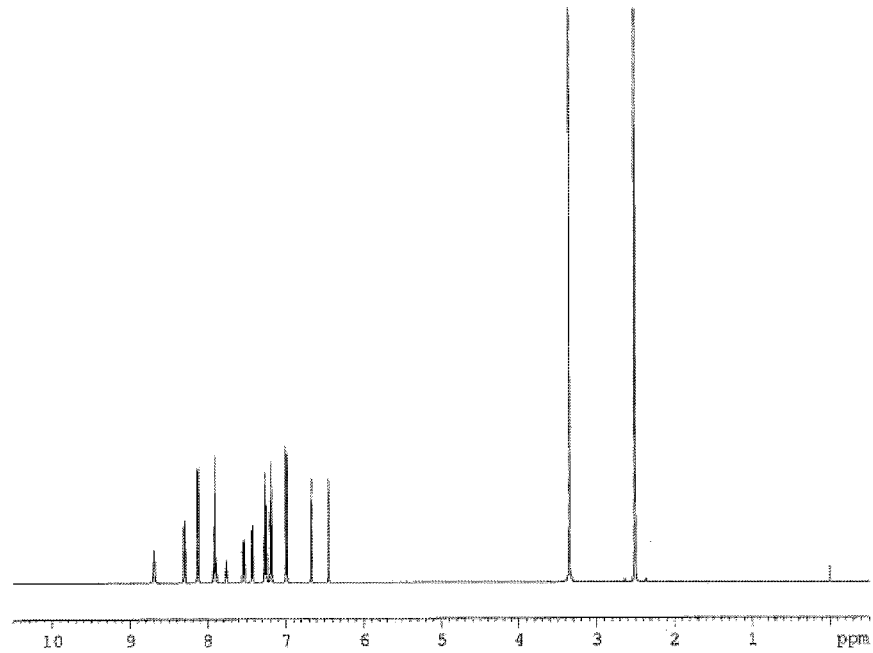
FIG. 2 is a $^1$H-NMR chart of the compound of Example 2 of the present invention (Compound 2).

The structure of the pale yellow powder product was identified by NMR. The $^1$H-NMR measurement result is shown in FIG. 2.

$^1$H-NMR (DMSO-$d_6$) detected 33 hydrogen signals, as follows. δ (ppm)=8.60 (2H), 8.32 (2H), 8.13 (4H), 7.95 (4H), 7.75 (1H), 7.58 (2H), 7.43 (2H), 7.25 (4H), 7.17 (4H), 6.98 (4H), 6.68 (2H), 6.45 (2H).

Example 3

Synthesis of 2,7-bis{9,9-Dimethylacrydan-10-yl}-10-phenyl-10H-spiro{acridine-9,9'-(4,5-diazafluorene)} (Compound 3)

1.2 g of the 2,7-dibromo-10-phenyl-10H-spiro{acridine-9,9'-(4,5-diazafluorene)} synthesized in Example 1, 1.8 g of 9,9-dimethylacrydan, 1.3 g of potassium carbonate, 0.4 g of copper(I) iodide, 0.1 g of 2-(dicyclohexylphosphino)biphenyl, and 24 ml of o-xylene were added into a nitrogen-substituted reaction vessel, and heated to reflux for 48 h. After adding 100 ml of toluene, the mixture was heated, and stirred at 100° C. The filtrate was collected by thermal filtration, and concentrated under reduced pressure to obtain a crude product. The crude product was purified by column chromatography (support: silica gel, eluent: toluene/ethyl acetate), and through crystallization with a mixed solvent of toluene and methanol to obtain a pale yellow powder of 2,7-bis{9,9-dimethylacrydan-10-yl}-10-phenyl-10H-spiro{acridine-9,9'-(4,5-diazafluorene)} (Compound 3; 0.5 g; yield 27%).

Figure 3:
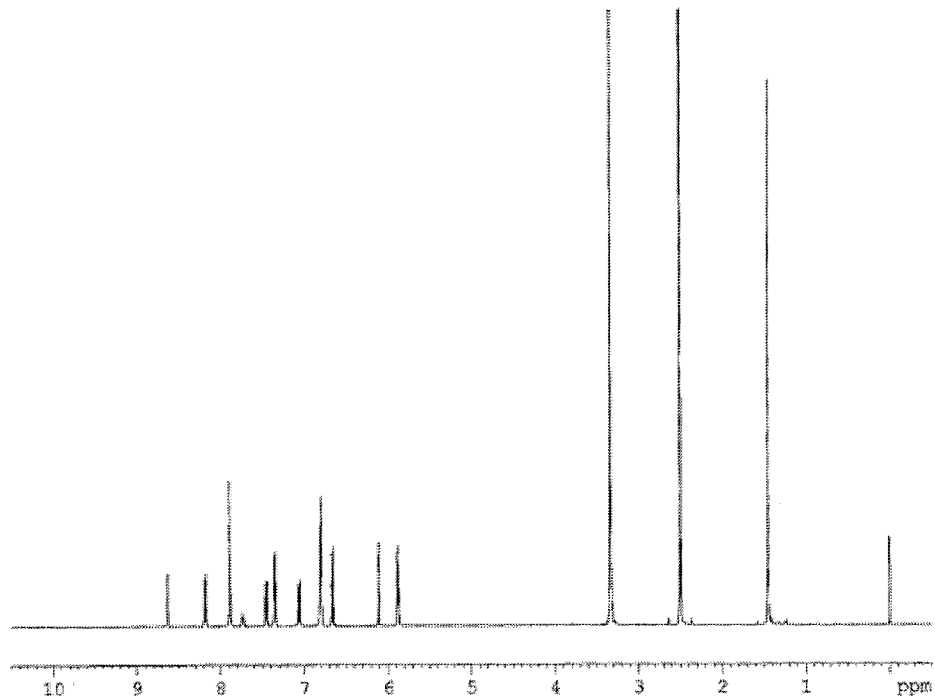
FIG. 3 is a $^1$H-NMR chart of the compound of Example 3 of the present invention (Compound 3).

The structure of the pale yellow powder product was identified by NMR. The $^1$H-NMR measurement result is shown in FIG. 3.

$^1$H-NMR (DMSO-$d_6$) detected 45 hydrogen signals, as follows. δ (ppm)=8.64 (2H), 8.17 (2H), 7.89 (4H), 7.74 (1H), 7.45 (2H), 7.36 (4H), 7.06 (2H), 6.80 (8H), 6.66 (2H), 6.11 (2H), 5.88 (4H), 3.35 (12H).

Example 4

Synthesis of 2,7-bis(10H-Phenoxazin-10-yl)-10-phenyl-10H-spiro{acridine-9,9'-(4,5-diazafluorene)} (Compound 4)

1.5 g of the 2,7-dibromo-10-phenyl-10H-spiro{acridine-9,9'-(4,5-diazafluorene)} synthesized in Example 1, 1.9 g of phenoxazine, 1.1 g of sodium tert-butoxide, 0.09 g of palladium acetate, 0.1 g of 2-(dicyclohexylphosphino)biphenyl, and 30 ml of o-xylene were added into a nitrogen-substituted reaction vessel, and heated to reflux for 48 h. After adding 100 ml of toluene, the mixture was heated, and stirred at 100° C. The filtrate was collected by thermal filtration, and concentrated under reduced pressure to obtain a crude product. The crude product was purified by column chromatography (support: silica gel, eluent: toluene/ethyl acetate), and through recrystallization with toluene to obtain a pale yellowish green powder of 2,7-bis(10H-phenoxazin-10-yl)-10-phenyl-10H-spiro{acridine-9,9'-(4,5-diazafluorene)} (Compound 4; 0.6 g; yield 30%).

Figure 4:
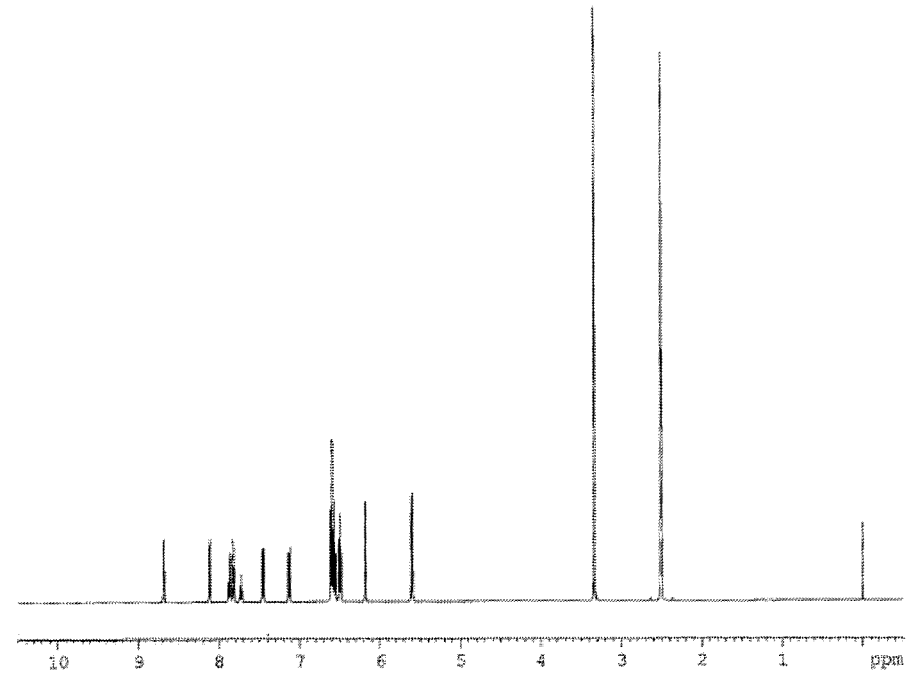
FIG. 4 is a $^1$H-NMR chart of the compound of Example 4 of the present invention (Compound 4).

The structure of the pale yellowish green powder product was identified by NMR. The $^1$H-NMR measurement result is shown in FIG. 4.

$^1$H-NMR (DMSO-$d_6$) detected 33 hydrogen signals, as follows. δ (ppm)=8.67 (2H), 8.11 (2H), 7.86 (2H), 7.81 (2H), 7.71 (1H), 7.44 (2H), 7.12 (2H), 6.62-6.55 (10H), 6.49 (4H), 6.17 (2H), 5.60 (4H).

Example 5

A 100 nm-thick vapor-deposited film was fabricated on an ITO substrate using the compounds of the present invention. The work function was measured using an atmosphere photoelectron spectrometer (AC-3 produced by Riken Keiki Co., Ltd.).

| | Work function |
|---|---|
| Compound of Example 1 of the present invention | 5.12 eV |
| Compound of Example 2 of the present invention | 5.52 eV |
| CBP | 6.00 eV |

As demonstrated above, the compounds of the present invention have preferable energy levels as a light emitting layer material, comparable to that of CBP used as a common light emission host.

Example 6

A $10^{-5}$ mol/L toluene solution was prepared for the compound of Example 1 of the present invention (Compound 1). This toluene solution was irradiated with ultraviolet light at 300 K while being aerated with nitrogen, and fluorescence having a peak wavelength of 527 nm was observed.

The time-resolved spectrum of the above toluene solution was also measured before and after the aeration with nitrogen, using a compact fluorescence lifetime spectrometer (Quantaurus-tau produced by Hamamatsu Photonics K.K.). The emission lifetime was observed as a shorter life component (fluorescence) of 0.080 μs, and a longer life component (delayed fluorescence) of 2.35 μs.

The PL quantum efficiency of the above toluene solution was also measured before and after the aeration with nitrogen, using an absolute PL quantum yields measurement system (Quantaurus-QY produced by Hamamatsu Photonics K.K.) at 300 K. The PL quantum efficiency was 4.4% before the aeration with nitrogen, and 33.5% after the aeration with nitrogen.

Example 7

A $10^{-5}$ mol/L toluene solution was prepared for the compound of Example 2 of the present invention (Compound 2) instead of the compound of Example 1 of the present invention (Compound 1) used in Example 6, and the characteristics of the toluene solution were evaluated in the same manner as in Example 6. As a result, fluorescence having a peak wavelength of 445 nm was observed. The emission lifetime was observed as a shorter life component (fluorescence) of 0.016 μs, and a longer life component (delayed fluorescence) of 15.0 μs. The PL quantum efficiency was 1.2% before the aeration with nitrogen, and 4.8% after the aeration with nitrogen.

Example 8

A $10^{-5}$ mol/L toluene solution was prepared for the compound of Example 3 of the present invention (Compound 3) instead of the compound of Example 1 of the present invention (Compound 1) used in Example 6, and the characteristics of the toluene solution were evaluated in the same manner as in Example 6. As a result, fluorescence having a peak wavelength of 489 nm was observed. The emission lifetime was observed as a shorter life component (fluorescence) of 0.054 μs, and a longer life component (delayed fluorescence) of 9.0 μs. The PL quantum efficiency was 5.8% before the aeration with nitrogen, and 13.8% after the aeration with nitrogen.

Example 9

A $10^{-5}$ mol/L toluene solution was prepared for the compound of Example 4 of the present invention (Compound 4) instead of the compound of Example 1 of the present invention (Compound 1) used in Example 6, and the characteristics of the toluene solution were evaluated in the same manner as in Example 6. As a result, fluorescence having a peak wavelength of 507 nm was observed. The emission lifetime was observed as a shorter life component (fluorescence) of 0.014 μs, and a longer life component (delayed fluorescence) of 0.122 μs. The PL quantum efficiency was 3.9% before the aeration with nitrogen, and 21.1% after the aeration with nitrogen.

Example 10

Figure 5:
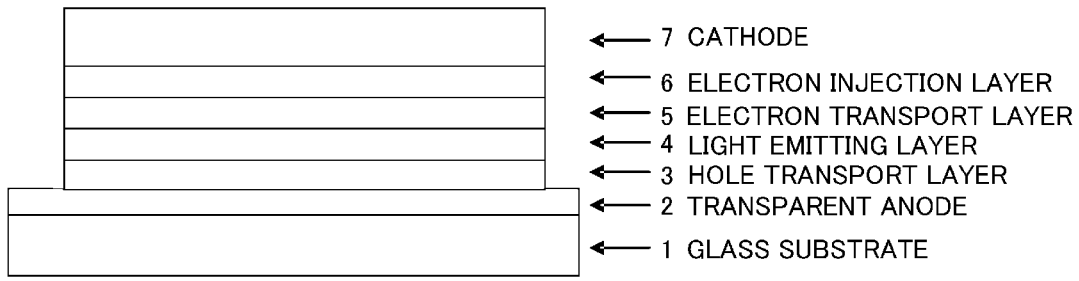
FIG. 5 is a diagram illustrating the configuration of the organic EL device of Example 10.

An organic EL device was fabricated by vapor-depositing a hole transport layer 3, a light emitting layer 4, an electron transport layer 5, an electron injection layer 6, and a cathode (aluminum electrode) 7 in this order on a glass substrate 1 on which an ITO electrode was formed as a transparent anode 2 beforehand, as shown in FIG. 5.

Specifically, the glass substrate 1 having ITO (a thickness of 100 nm) formed thereon was washed with an organic solvent, and subjected to a UV ozone treatment to wash the surface. The glass substrate with the ITO electrode was then installed in a vacuum vapor deposition apparatus, and the pressure was reduced to 0.001 Pa or less.

This was followed by formation of the hole transport layer 3 by vapor depositing NPD over the transparent anode 2 in a thickness of 35 nm at a vapor deposition rate of 2.0 Å/sec. Then, the light emitting layer 4 was formed on the hole transport layer 3 in a thickness of 15 nm by dual vapor deposition of mCP and the compound of Example 1 of the present invention (Compound 1) at a vapor deposition rate ratio of 95:5 (mCP: compound of Example 1 of the present invention (Compound 1)). The electron transport layer 5 was then formed on the light emitting layer 4 by forming TPBI in a thickness of 50 nm at a deposition rate of 2.0 Å/sec. The electron injection layer 6 was then formed on the electron transport layer 5 by forming lithium fluoride in a thickness of 0.8 nm at a deposition rate of 0.1 Å/sec. Finally, the cathode 7 was formed by vapor depositing aluminum in a thickness of 70 nm. The characteristics of the organic EL device thus fabricated were measured in the atmosphere at an ordinary temperature.

Figure 6:
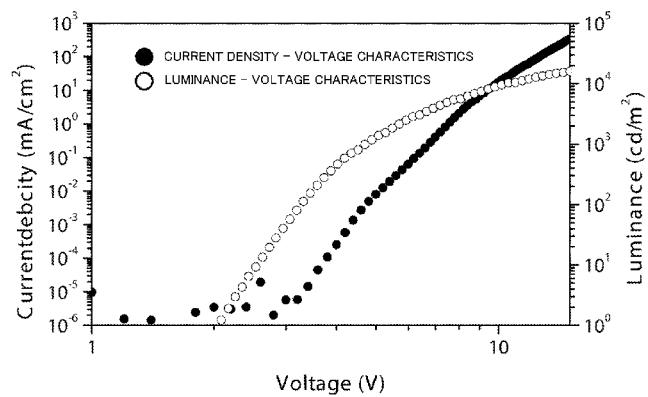
FIG. 6 is a graph representing the current density-voltage characteristics, and the luminance-voltage characteristics of the organic EL device of Example 10.
Figure 7:
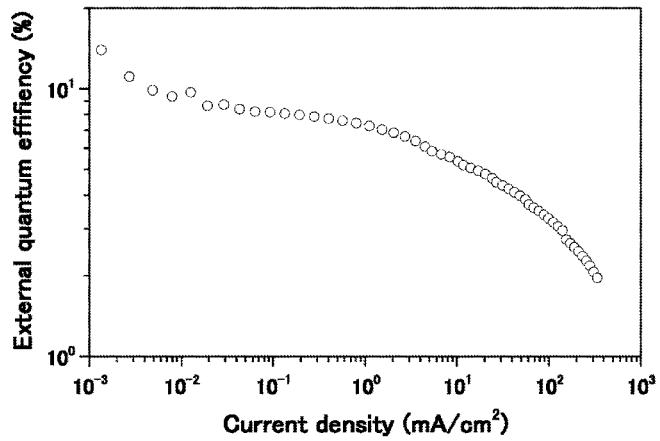
FIG. 7 is a graph representing the current density-external quantum efficiency characteristics of the organic EL device of Example 10.

The organic EL device fabricated with the compound of Example 1 of the present invention (compound 1) was measured for emission characteristics by applying DC voltage. FIG. 6 represents the current density-voltage characteristics, and the luminance-voltage characteristics. FIG. 7 represents the external quantum efficiency-current density characteristics.

The organic EL device had high emission characteristics, with a luminance of 1,393 cd/m$^2$, and a current efficiency of 13.6 cd/A upon passing current at a current density of 10 mA/cm$^2$. The external quantum efficiency was as high as 9.6%, a value that far exceeds the theoretical external quantum efficiency of 5% with a common fluorescence material.

As demonstrated above, the organic EL device using the compounds of the present invention was shown to be capable of achieving high luminous efficiency, and high external quantum efficiency.

INDUSTRIAL APPLICABILITY

The spiro compounds having an azafluorene ring structure of the present invention can emit delayed fluorescence and have desirable thin-film stability, and the spiro compounds are excellent as material of a light emitting layer, especially as a dopant material of a light emitting layer. An organic EL device produced by using the compounds can have improved luminous efficiency, and high external quantum efficiency. This makes the present invention highly useful in industry.

DESCRIPTION OF REFERENCE NUMERAL

1 Glass substrate
2 Transparent anode

3 Hole transport layer
4 Light emitting layer
5 Electron transport layer
6 Electron injection layer
7 Cathode

The invention claimed is:
1. A spiro compound of the following general formula (1-1) having an azafluorene ring structure

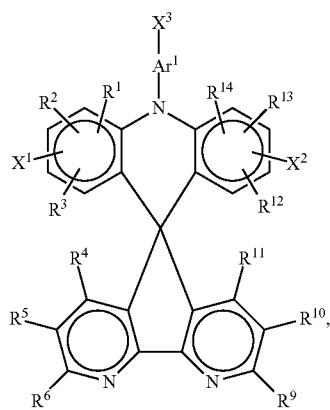

(1-1)

wherein, $X^1$ and $X^2$ in the general formula (1-1) represent a substituted or unsubstituted phenoxazinyl, substituted or unsubstituted phenothiazinyl, substituted or unsubstituted phenazinyl, or a diphenylamino group, $X^3$ represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, at least one of $X^1$, $X^2$, and $X^3$ is a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group, $Ar^1$ represents a divalent group of an unsubstituted aromatic hydrocarbon wherein the unsubstituted aromatic hydrocarbon is not fluorenyl, and $R^1$ to $R^6$, and $R^9$ to $R^{14}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^6$, and $R^9$ to $R^{14}$ may bind to each other via a single bond, substituted or unsubstituted methylene, an oxygen atom, or a sulfur atom to form a ring.

2. The spiro compound having an azafluorene ring structure according to claim 1, wherein the spiro compound is represented by the following general formula (1a-1)

[Chemical Formula 4]

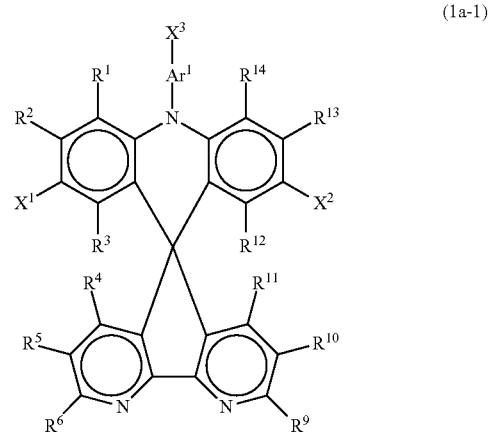

(1a-1)

wherein, $X^1$ and $X^2$ in the general formula (1a-1) represent a substituted or unsubstituted phenoxazinyl, substituted or unsubstituted phenothiazinyl, substituted or unsubstituted phenazinyl, or a diphenylamino group, $X^3$ represents a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, at least one of $X^1$, $X^2$, and $X^3$ is a substituted or unsubstituted aromatic hydrocarbon group, a substituted or unsubstituted aromatic heterocyclic group, a substituted or unsubstituted condensed polycyclic aromatic group, or a disubstituted amino group substituted with a group selected from an aromatic hydrocarbon group, an aromatic heterocyclic group, and a condensed polycyclic aromatic group, $Ar^1$ represents a divalent group of an unsubstituted aromatic hydrocarbon wherein the unsubstituted aromatic hydrocarbon is not fluorenyl, and $R^1$ to $R^6$, and $R^9$ to $R^{14}$ may be the same or different, and represent a hydrogen atom, a deuterium atom, a fluorine atom, a chlorine atom, cyano, nitro, linear or branched alkyl of 1 to 6 carbon atoms that may have a substituent, cycloalkyl of 5 to 10 carbon atoms that may have a substituent, linear or branched alkenyl of 2 to 6 carbon atoms that may have a substituent, linear or branched alkyloxy of 1 to 6 carbon atoms that may have a substituent, cycloalkyloxy of 5 to 10 carbon atoms that may have a substituent, a substituted or unsubstituted aromatic hydrocarbon group, a substituted or unsubstituted aromatic heterocyclic group, a substituted or unsubstituted condensed polycyclic aromatic group, substituted or unsubstituted aryloxy, or a disubstituted amino group substituted with a group selected from an aromatic hydrocarbon group, an aromatic heterocyclic group, and a condensed polycyclic aromatic group, wherein $R^1$ to $R^6$, and $R^9$ to $R^{14}$ may bind to each other via a single bond, substituted or unsubstituted methylene, an oxygen atom, or a sulfur atom to form a ring.

3. The spiro compound having an azafluorene ring structure according to claim 1, wherein, $X^3$ in the general formula (1-1) is substituted or unsubstituted carbazolyl, substituted or unsubstituted phenoxazinyl, substituted or unsubstituted phenothiazinyl, substituted or unsubstituted acridinyl, substituted or unsubstituted phenazinyl, or a disubstituted amino group substituted with an aromatic hydrocarbon group or a condensed polycyclic aromatic group.

4. The spiro compound having an azafluorene ring structure according to claim 1, wherein, $X^3$ in the general formula (1-1) is a hydrogen atom.

5. A light-emitting material comprising the Spiro compound having an azafluorene ring structure according to claim 1.

6. The light-emitting material according to claim 5, which emits delayed fluorescence.

7. An organic electroluminescent device comprising a pair of electrodes, and one or more organic layers sandwiched between the pair of electrodes, wherein the spiro compound having an azafluorene ring structure according to claim 1 is used as a constituent material of at least one organic layer.

8. The organic electroluminescent device according to claim 7, wherein one of the one or more organic layers is a light emitting layer.

9. The organic electroluminescent device according to claim 8, wherein one of the one or more organic layers emits delayed fluorescence.

10. The organic electroluminescent device according to claim 7, wherein one of the one or more organic layers is a hole transport layer.

11. The organic electroluminescent device according to claim 7, wherein one of the one or more organic layers is an electron blocking layer.

* * * * *